United States Patent
Ling et al.

(10) Patent No.: US 9,751,924 B2
(45) Date of Patent: *Sep. 5, 2017

(54) METHODS OF USING COMPOSITIONS COMPRISING FUSION VARIANTS OF FGF19 POLYPEPTIDES FOR REDUCING GLUCOSE LEVELS IN A SUBJECT

(71) Applicant: NGM Biopharmaceuticals, Inc., South San Francisco, CA (US)

(72) Inventors: Lei Ling, Foster City, CA (US); Darrin Anthony Lindhout, Mountain View, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/983,324

(22) Filed: Dec. 29, 2015

(65) Prior Publication Data

US 2016/0168216 A1    Jun. 16, 2016

Related U.S. Application Data

(62) Division of application No. 14/743,851, filed on Jun. 18, 2015, now Pat. No. 9,580,483, which is a division of application No. 14/616,401, filed on Feb. 6, 2015, now Pat. No. 9,089,525, which is a division of application No. 13/538,705, filed on Jun. 29, 2012, now Pat. No. 8,951,966.

(60) Provisional application No. 61/504,128, filed on Jul. 1, 2011, provisional application No. 61/515,126, filed on Aug. 4, 2011.

(51) Int. Cl.
| | |
|---|---|
| *A61K 38/18* | (2006.01) |
| *C07K 14/50* | (2006.01) |
| *G01N 33/50* | (2006.01) |
| *A61K 31/14* | (2006.01) |
| *A61K 31/155* | (2006.01) |
| *A61K 45/06* | (2006.01) |
| *A61K 31/785* | (2006.01) |
| *A61K 38/00* | (2006.01) |

(52) U.S. Cl.
CPC .............. *C07K 14/50* (2013.01); *A61K 31/14* (2013.01); *A61K 31/155* (2013.01); *A61K 31/785* (2013.01); *A61K 38/1825* (2013.01); *A61K 45/06* (2013.01); *G01N 33/5088* (2013.01); *A61K 38/00* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 6,635,468 B2 | 10/2003 | Ashkenazi |
| 6,716,626 B1 | 4/2004 | Itoh |
| 6,806,352 B2 | 10/2004 | Desnoyers |
| 6,812,339 B1 | 11/2004 | Venter |
| 6,987,121 B2 | 1/2006 | Kliewer |
| 7,115,415 B2 | 10/2006 | Goddard |
| 7,129,072 B1 | 10/2006 | Schlessinger |
| 7,208,312 B1 | 4/2007 | Desnoyers |
| 7,259,248 B2 | 8/2007 | Itoh |
| 7,288,406 B2 | 10/2007 | Bogin |
| 7,390,879 B2 | 6/2008 | Ashkenazi |
| 7,459,540 B1 | 12/2008 | Thomason |
| 7,491,697 B2 | 2/2009 | Beals |
| 7,576,190 B2 | 8/2009 | Glaesner |
| 7,582,607 B2 | 9/2009 | Frye |
| 7,622,445 B2 | 11/2009 | Frye |
| 7,655,627 B2 | 2/2010 | Frye |
| 7,667,008 B2 | 2/2010 | Thomason |
| 7,705,195 B2 | 4/2010 | French |
| 7,723,297 B2 | 5/2010 | Itoh |
| 7,947,866 B2 | 5/2011 | Sparks |
| 8,012,931 B2 | 9/2011 | Cujec |
| 8,034,770 B2 | 10/2011 | Belouski |
| 8,188,040 B2 | 5/2012 | Belouski |
| 8,324,160 B2 | 12/2012 | Li |
| 8,361,963 B2 | 1/2013 | Belouski |
| 8,383,365 B2 | 2/2013 | Cujec |
| 8,410,051 B2 | 4/2013 | Belouski |
| 8,420,088 B2 | 4/2013 | Glass |
| 8,481,031 B2 | 7/2013 | Glass |

(Continued)

FOREIGN PATENT DOCUMENTS

| | | |
|---|---|---|
| DE | 10100588 | 7/2002 |
| DE | 10100587 | 11/2002 |
| EP | 2163626 | 3/2010 |
| JP | 2002112772 | 4/2002 |
| JP | 2009039117 | 2/2009 |
| JP | 2013194049 | 9/2013 |
| NZ | 602702 | 3/2014 |
| WO | WO 00/60085 | 10/2000 |
| WO | WO 01/18209 | 3/2001 |
| WO | WO 01/49740 | 7/2001 |

(Continued)

OTHER PUBLICATIONS

Camilleri et al., "Measurement of Serum 7α-hydroxy-4-cholesten-3-one (or 7αC4), a Surrogate Test for Bile Acid Malabsorption in Health, Ileal Disease and Irritable Bowel Syndrome using Liquid Chromatography-Tandom Mass Spectrometry," Neurogastroenterol Motil. 21(7):734-e43 (2009).

(Continued)

*Primary Examiner* — Christine J Saoud
(74) *Attorney, Agent, or Firm* — Jones Day

(57) ABSTRACT

The invention relates to methods for and uses in reducing glucose levels in subjects in need thereof with variants and fusions of fibroblast growth factor 19 (FGF19) proteins and peptide sequences (and peptidomimetics).

113 Claims, 31 Drawing Sheets

(56) References Cited

U.S. PATENT DOCUMENTS

| | | |
|---|---|---|
| 8,535,912 B2 | 9/2013 | Sonoda |
| 8,541,369 B2 | 9/2013 | Dickinson |
| 8,580,936 B2 | 11/2013 | Williams |
| 8,618,053 B2 | 12/2013 | Belouski |
| 8,642,546 B2 | 2/2014 | Belouski |
| 8,673,860 B2 | 3/2014 | Schellenberger |
| 8,741,841 B2 | 6/2014 | Darling |
| 8,795,985 B2 | 8/2014 | Belouski |
| 8,802,697 B2 | 8/2014 | Bifulco |
| 8,809,499 B2 | 8/2014 | Fan |
| 8,835,385 B2 | 9/2014 | Belouski |
| 8,883,726 B2 | 11/2014 | Dickinson |
| 8,889,426 B2 | 11/2014 | Mohammadi |
| 8,889,621 B2 | 11/2014 | Mohammadi |
| 8,927,492 B2 | 1/2015 | Darling |
| 8,932,589 B2 | 1/2015 | Glass |
| 8,951,966 B2 | 2/2015 | Ling |
| 8,962,557 B2 | 2/2015 | Blaber |
| 8,975,223 B2 | 3/2015 | Vignati |
| 8,993,727 B2 | 3/2015 | Walker |
| 8,999,929 B2 | 4/2015 | Mohammadi |
| 9,006,400 B2 | 4/2015 | Boettcher |
| 9,089,525 B1 | 7/2015 | Ling |
| 9,273,107 B2 | 3/2016 | Ling |
| 9,290,557 B2 | 3/2016 | Ling |
| 9,580,483 B2 | 2/2017 | Ling |
| 2002/0012961 A1 | 1/2002 | Botstein |
| 2002/0042367 A1 | 4/2002 | Stewart |
| 2002/0082205 A1 | 6/2002 | Itoh |
| 2002/0151496 A1 | 10/2002 | Bringmann |
| 2002/0155543 A1 | 10/2002 | Adams |
| 2003/0045489 A1 | 3/2003 | Murphy |
| 2003/0065140 A1 | 4/2003 | Vernet |
| 2003/0105302 A1 | 6/2003 | Itoh |
| 2003/0113718 A1 | 6/2003 | Ashkenazi |
| 2003/0119112 A1 | 6/2003 | Baker |
| 2003/0125521 A1 | 7/2003 | Baker |
| 2003/0166051 A1 | 9/2003 | Desnoyers |
| 2003/0170822 A1 | 9/2003 | Itoh |
| 2003/0180890 A1 | 9/2003 | Conklin |
| 2003/0185846 A1 | 10/2003 | Ashkenazi |
| 2003/0220246 A1 | 11/2003 | Conklin |
| 2004/0014658 A1 | 1/2004 | Bogin |
| 2004/0126852 A1 | 7/2004 | Stewart |
| 2004/0146908 A1 | 7/2004 | Adams |
| 2004/0185494 A1 | 9/2004 | Itoh |
| 2005/0026243 A1 | 2/2005 | Stewart |
| 2005/0026832 A1 | 2/2005 | Adams |
| 2005/0107475 A1 | 5/2005 | Jones |
| 2005/0153305 A1 | 7/2005 | Vernet |
| 2005/0181375 A1 | 8/2005 | Aziz |
| 2005/0196842 A1 | 9/2005 | Botstein |
| 2006/0160181 A1 | 7/2006 | Luethy |
| 2006/0172386 A1 | 8/2006 | Itoh |
| 2006/0246540 A1 | 11/2006 | Ashkenazi |
| 2006/0275794 A1 | 12/2006 | Carrino |
| 2006/0281679 A1 | 12/2006 | Itoh |
| 2007/0037165 A1 | 2/2007 | Venter |
| 2007/0042395 A1 | 2/2007 | Botstein |
| 2007/0077626 A1 | 4/2007 | Botstein |
| 2007/0238657 A1 | 10/2007 | Itoh |
| 2007/0253966 A1 | 11/2007 | Glaesner |
| 2008/0057076 A1 | 3/2008 | Bringmann |
| 2008/0124759 A1 | 5/2008 | Conklin |
| 2009/0081658 A1 | 3/2009 | Belouchi |
| 2009/0098603 A1 | 4/2009 | Botstein |
| 2009/0196876 A1 | 8/2009 | Sparks |
| 2009/0226459 A1 | 9/2009 | Powers |
| 2009/0312265 A1 | 12/2009 | Schmidtchen |
| 2010/0215657 A1 | 8/2010 | Glass |
| 2010/0239554 A1 | 9/2010 | Schellenberger |
| 2010/0323954 A1 | 12/2010 | Li |
| 2011/0015345 A1 | 1/2011 | Pinkstaff |
| 2011/0053787 A1 | 3/2011 | Brulliard |
| 2011/0104152 A1 | 5/2011 | Sonoda |
| 2011/0107439 A1 | 5/2011 | De Wit |
| 2011/0135657 A1 | 6/2011 | Hu |
| 2011/0150903 A1 | 6/2011 | Baurin |
| 2011/0195077 A1 | 8/2011 | Glass |
| 2011/0195895 A1 | 8/2011 | Walker |
| 2011/0207912 A1 | 8/2011 | Botstein |
| 2011/0306129 A1 | 12/2011 | Nistor |
| 2011/0312881 A1 | 12/2011 | Silverman |
| 2012/0003216 A1 | 1/2012 | Belouski |
| 2012/0064544 A1 | 3/2012 | Econs |
| 2013/0004492 A1 | 1/2013 | Marshall |
| 2013/0023474 A1 | 1/2013 | Ling |
| 2013/0116171 A1 | 5/2013 | Jonker |
| 2013/0122004 A1 | 5/2013 | Glass |
| 2013/0143796 A1 | 6/2013 | Li |
| 2013/0172275 A1 | 7/2013 | Mohammadi |
| 2013/0183294 A1 | 7/2013 | Pai |
| 2013/0183319 A1 | 7/2013 | Bange |
| 2013/0184211 A1 | 7/2013 | Mohammadi |
| 2013/0231277 A1 | 9/2013 | Mohammadi |
| 2013/0324458 A1 | 12/2013 | Glass |
| 2013/0324701 A1 | 12/2013 | Williams |
| 2013/0331317 A1 | 12/2013 | Mohammadi |
| 2013/0331325 A1 | 12/2013 | Mohammadi |
| 2014/0094406 A1 | 4/2014 | Mohammadi |
| 2014/0148388 A1 | 5/2014 | Sonoda |
| 2014/0155316 A1 | 6/2014 | Mohammadi |
| 2014/0189893 A1 | 7/2014 | Li |
| 2014/0194352 A1 | 7/2014 | Ling |
| 2014/0243260 A1 | 8/2014 | Mohammadi |
| 2014/0243266 A1 | 8/2014 | Ling |
| 2015/0079065 A1 | 3/2015 | Wolf |
| 2015/0111821 A1 | 4/2015 | Suh |
| 2015/0284442 A1 | 10/2015 | Ling |
| 2015/0291677 A1 | 10/2015 | Ling |
| 2016/0045565 A1 | 2/2016 | Ling |
| 2016/0166642 A1 | 6/2016 | Ling |
| 2016/0168215 A1 | 6/2016 | Ling |
| 2016/0168216 A1 | 6/2016 | Ling |
| 2016/0168217 A1 | 6/2016 | Ling |
| 2016/0168218 A1 | 6/2016 | Ling |
| 2016/0168219 A1 | 6/2016 | Ling |
| 2016/0168220 A1 | 6/2016 | Ling |
| 2016/0168221 A1 | 6/2016 | Ling |
| 2016/0168222 A1 | 6/2016 | Ling |
| 2016/0200788 A1 | 7/2016 | Ling |
| 2016/0252497 A1 | 9/2016 | Ling |

FOREIGN PATENT DOCUMENTS

| | | |
|---|---|---|
| WO | WO 01/49849 | 7/2001 |
| WO | WO 01/61007 | 8/2001 |
| WO | WO 02/36732 | 5/2002 |
| WO | WO 02/41911 | 5/2002 |
| WO | WO 02/055693 | 7/2002 |
| WO | WO 03/080803 | 10/2003 |
| WO | WO 2004/026228 | 4/2004 |
| WO | WO 2004/063355 | 7/2004 |
| WO | WO 2006/004076 | 1/2006 |
| WO | WO 2006/048291 | 5/2006 |
| WO | WO 2006/049854 | 5/2006 |
| WO | WO 2008/021196 | 2/2008 |
| WO | WO 2008/030273 | 3/2008 |
| WO | WO 2009/076478 | 6/2009 |
| WO | WO 2009/090553 | 7/2009 |
| WO | WO 2009/095372 | 8/2009 |
| WO | WO 2009/116861 | 9/2009 |
| WO | WO 2010/004204 | 1/2010 |
| WO | WO 2010/006214 | 1/2010 |
| WO | WO 2010/042747 | 4/2010 |
| WO | WO 2010/065439 | 6/2010 |
| WO | WO 2010/080976 | 7/2010 |
| WO | WO 2010/083051 | 7/2010 |
| WO | WO 2010/129600 | 11/2010 |
| WO | WO 2010/139741 | 12/2010 |
| WO | WO 2010/142665 | 12/2010 |
| WO | WO 2010/148142 | 12/2010 |
| WO | WO 2011/047267 | 4/2011 |
| WO | WO 2011/071783 | 6/2011 |

(56) References Cited

FOREIGN PATENT DOCUMENTS

| WO | WO 2011/084808 | 7/2011 |
|---|---|---|
| WO | WO 2011/089203 | 7/2011 |
| WO | WO 2011/092234 | 8/2011 |
| WO | WO 2011/130417 | 10/2011 |
| WO | WO 2011/130729 | 10/2011 |
| WO | WO 2011/154349 | 12/2011 |
| WO | WO 2012/010553 | 1/2012 |
| WO | WO 2012/031603 | 3/2012 |
| WO | WO 2012/062078 | 5/2012 |
| WO | WO 2012/066075 | 5/2012 |
| WO | WO 2012/086809 | 6/2012 |
| WO | WO 2012/138919 | 10/2012 |
| WO | WO 2012/140650 | 10/2012 |
| WO | WO 2012/154263 | 11/2012 |
| WO | WO 2012/158704 | 11/2012 |
| WO | WO 2012/170438 | 12/2012 |
| WO | WO 2012/170704 | 12/2012 |
| WO | WO 2012/177481 | 12/2012 |
| WO | WO 2013/006486 | 1/2013 |
| WO | WO 2013/010780 | 1/2013 |
| WO | WO 2013/027191 | 2/2013 |
| WO | WO 2013033452 | 3/2013 |
| WO | WO 2013/049234 | 4/2013 |
| WO | WO 2013/109856 | 7/2013 |
| WO | WO 2013/131091 | 9/2013 |
| WO | WO 2013/151671 | 10/2013 |
| WO | WO 2013/173158 | 11/2013 |
| WO | WO 2013/184958 | 12/2013 |
| WO | WO 2013/184960 | 12/2013 |
| WO | WO 2013/184962 | 12/2013 |
| WO | WO 2013/188182 | 12/2013 |
| WO | WO 2014/031420 | 2/2014 |
| WO | WO 2014/037373 | 3/2014 |
| WO | WO 2014/085365 | 6/2014 |
| WO | WO 2014/105939 | 7/2014 |
| WO | WO 2014/130659 | 8/2014 |
| WO | WO 2014/149699 | 9/2014 |
| WO | WO 2014/152090 | 9/2014 |
| WO | WO 2015/065897 | 5/2015 |
| WO | WO 2015/112886 | 7/2015 |
| WO | WO 2015/183890 | 12/2015 |
| WO | WO 2015/195509 | 12/2015 |
| WO | WO/2016/065106 | 4/2016 |
| WO | WO/2016/073855 | 5/2016 |

OTHER PUBLICATIONS

Chen et al., "Soluble FGFR4 extracellular domain inhibits FGF19-induced activation of FGFR4 signaling and prevents nonalcoholic fatty liver disease," Biochem. Biophys. Res. Comm. 409:651-656 (2009).

Claudel et al., "Role of Nuclear Receptors for Ble Acid Metabolism, Bile Secretion, Cholestasis, and Gallstone Disease," Biochim. Biophys. Acta 1812:867-878 (2011).

Ďurovcováet al., "Plasma Concentration of Fibroblast Growth Factors 21 and 19 in Patients with Cushing's Syndrome," Physiol. Res. 59:415-422 (2010).

Foltz et al., "Treating Diabetes and Obesity with an FGF21-Mimetic Antibody Activating the βKlotho/FGFR1c Receptor Complex," Sci. Transl. Med. 4:162ra153; pp. 1-10 (2012).

Foltz et al., "Supplementary Materials for: Treating Diabetes and Obesity with an FGF21-Mimetic Antibody Activating the βKlotho/FGFR 1c Receptor Complex," Sci. Transl. Med. 4:162ra153; pp. 1-13 (2012).

French et al., "Targeting FGFR4 Inhibits Hepatocellular Carcinoma in Preclinical Mouse Models," PLoS One 7(5):e36713 (2012).

Ge et al., "Characterization of a FGF19 Variant with Altered Receptor Specificity Revealed a Central Role for FGFR 1c in the Regulation of Glucose Metabolism," PLoS One 7(3):e33603 (2012).

Harmer et al., "The Crystal Structure of Fibroblast Growth Factor (FGF) 19 Reveals Novel Features of the FGF Family and Offers a Structural Basis for Its Unusual Receptor Affinity," Biochemistry 43:629-640 (2004).

Hofmann et al., "Chronic diarrhea due to excessive bile acid synthesis and not defective ileal transport: A new syndrome of defective FGF19 release," Clin Gastroenterol Hepatol. 7(11): 1151-1154 (2009).

Inagaki et al., "Fibroblast Growth Factor 15 Functions as an Enterohepatic Signal to Regulate Bile Acid Homeostasis," Cell Metabolism 2:217-225 (2005).

Kir et al., "Roles of FGF19 in Liver Metabolism," Cold Spring Harb. Symp. Quant. Biol. 76:139-144 (2011).

Kurosu et al., "Tissue-specific Expression fo βKlotho and Fibroblast Growth Factor (FGF) Receptor Isoforms Determines Metabolic Activity of FGF19 and FGF21," J. Biol. Chem. 282(37):26687-26695 (2007).

Kurosu et al., "Supplemental Data for: Tissue-specific Expression fo βKlotho and Fibroblast Growth Factor (FGF) Receptor Isoforms Determines Metabolic Activity of FGF19 and FGF21," J. Biol. Chem. (2007) (available at: http://www.jbc.org/content/suppl/2007/07/11/M704165200.DC1/Kurosu Suppl_Data.pdf (last visited Jul. 23, 2014).

Ling et al., "Identification of Gut Factors that Mimic the Metabolic Benefits Seen After Gastric Bypass Surgery," American Diabetes Association, 72nd Scientific Sessions, Jun. 8-12, 2012, Philadelphia, PA, http://www.abstactsonline.com.

Ling et al., NGM Biopharmaceuticals, Identification of Gut Factors that Mimic the Metabolic Benefits of Gastric Bypass Surgery, p. 1, Jun. 8-12, (2012) Abstract.

Luo et al., "A nontumorigenic variant of FGF19 treats cholestatic liver diseases," Sci Transl Med 6, 247ra100 (2014).

Micanovic et al., "Different roles of N—and C-termini in the functional activity of FGF21," J. Cell. Physiol. 219:227-234 (2009).

Miyata et al., "Involvement of Multiple Elements in FXR-mediated Transcriptional Activation of FGF19," J. Steroid Biochm. Mol. Biol. 132:41-47 (2012).

Nicholes et al., "A Mouse Model of Hepatocellular Carcinoma: Ectompic Expression of Fibroblast Growth Factor in Skeletal Muscle of Transgenic Mice," Toxicological Sciences. 126(2):446-456 (2012).

Ogawa et al., "BetaKlotho is Required for Metabolic Activity of Fibroblast Growth Factor 21," Proc. Natl. Acad. Sci. USA. 104:7432-7437 (2007).

Pai et al., "Antibody-Mediated Inhibition of Fibroblast Growth Factor 19 Results in Increased Bile Acids Synthesis and Ileal Malabsorption of Bile Acids in Cynomolgus Monkeys," Toxicological Sciences. 3:E18 (2012).

Pattni et al., "Fibroblast Growth Factor 19 and 7α-Hydroxy-4-Cholesten-3-one in the Diagnosis of Patients With Possible Bile Acid Diarrhea,"Clinical and Translational Gastroenterology. 26:312-324 (2012).

Potthoff et al., "Endocrine Fibroblast Growth Factors 15/19 and 21: From Feast to Famine," Genes Dev. 26:312-324 (2012).

Rose et al., "Molecular Control of Systemic Bile Acid Homeostasis by the Liver Glucocorticoid Receptor," Cell Metabolism 14:123-130 (2011).

Ryan et al., "FXR is a Molecular Target for the Effects of Vertical Sleeve Gastroectomy," Nature 509(7499):183-188 (2014); epub ahead of print Mar. 26, 2014.

Schaap, "Role of Fibroblast Growth Factor 19 in the Control of Glucose Homeostasis," Curr. Opin. Clin. Nutr. Metab. Care 15(4):386-391 (2012).

Walters, "A variant of FGF19 for treatment of disorders of cholestasis and bile acid metabolism," Ann. Transl. Med. 3(S1):S7 (2015).

Wu et al., "C-terminal Tail of FGF19 Determines Its Specificity toward Klotho C-receptors," J. Biol. Chem. 283(48):33304-33309 (2008).

Wu et al., "Role of FGF19 Induced FGFR4 Activation in the Regulation of Glucose Homeostasis, " Aging 1(12):1023-1027 (2009).

(56) References Cited

OTHER PUBLICATIONS

Wu et al., "Selective Activation of FGFR4 by an FGF19 Variant Does Not Improve Glucose Metabolism in ob/ob Mice," Proc. Natl. Acad. Sci. USA 106(34):14379-14384 (2009).
Wu et al., "FGF19-induced Hepatocyte Proliferation is Mediated Through FGFR4 Activation," J. Biol. Chem. 285(8):5165-5170 (2010).
Wu et al., "Separating Mitogenic and Metabolic Activities of Fibroblast Growth Factor 19 (FGF19)," Proc. Natl. Acad. Sci. USA 107(32):14158-14163 (2010).
Wu et al., "Therapeutic Utilities of Fibroblast Growth Factor 19," Expert Opin. Ther. Targets 15(11):1307-1316 (2011).
Wu et al., "FGF19 Regulates Cell Proliferation, Glucose and Bile Acid Metabolism via FGFR4-Dependent and Independent Pathways," PLoS One 6(3):e17868 (2011).
Xie et al., "FGF-19, A Novel Fibroblast Growth Factor with Unique Specificity for FGFR4," Cytokine 11(10):729-735 (1999).
Beenken et al, "The FGF family: biology, pathophysiology and therapy," Nat. Rev. Drug Discov., 8:235-253 (2009).
Bromberg et al., "Stat3 as an oncogene," Cell, 98:295-303 (1999).
Calvisi et al., "Ubiquitous activation of Ras and Jak/Stat pathways in human HCC," Gastroenterol., 130:1117-1128 (2006).
Chen et al., "Sorafenib overcomes Trail resistance of hepatocellular carcinoma cells through the inhibition of STAT3," Clin. Cancer Res,16:5189-5199 (2010).
Desnoyers et al., "Targeting FGF19 inhibits tumor growth in colon cancer xenograft and FGF19 transgenic hepatocellular carcinoma models," Oncogene 27:85-97 (2008).
Hasegawa, "The expansion of Prominin-1-positive epithelial-mesenchymal cells within periportal fibrosis of rotavirusinduced biliary atresia," Hepatol. 58:802A (2013).
He et al., "NF-κb and STAT3—key players in liver inflammation and cancer," Cell Res., 21:159-168 (2011).
He et al., "Hepatocyte IKKbeta/NF-kappaB inhibits tumor promotion and progression by preventing oxidative stress-driven STAT3 activation," Cancer Cell, 17: 286-297 (2010).
He et al., "Identification of liver cancer progenitors whose malignant progression depends on autocrine IL-6 signaling," Cell, 155:384-396 (2013).
Holt et al., "Definition of a novel growth factor-dependent signal cascade for the suppression of bile acid biosynthesis," Genes Dev., 17:1581-1591 (2003).
Ikeda et al., "Leptin receptor somatic mutations are frequent in HCV-infected cirrhotic liver and associated with hepatocellular carcinoma," Gastroenterol., 146:222-232 (2014).
Kakumu et al., "Interleukin 6 production by peripheral blood mononuclear cells in patients with chronic hepatitis B virus infection and primary biliary cirrhosis," Gastroenterologia Japonica, 28:18-24 (1993).
Karras et al., "STAT3 regulates the growth and immunoglobulin production of BCL(1) B cell lymphoma through control of cell cycle progression," Cellular immunol., 202:124-135 (2000).
Kenakin et al., "Signalling bias in new drug discovery detection, quantification and therapeutic impact," Nat. Rev. Drug Discov., 12:205-521 (2013).
Lin et al., "The STAT3 inhibitor NSC 74859 is effective in hepatocellular cancers with disrupted TGF-beta signaling," Oncogene, 28:961-972 (2009).
Sawey et al., "Identification of a Therapeutic Strategy Targeting Amplified FGF19 in Liver Cancer by Oncogenomic Screening," Cancer Cell, 19, 347-358 (2011).
Schaap et al., "High expression of the bile salt-homeostatic hormone fibroblast growth factor 19 in the liver of patients with extrahepatic cholestasis," Hepatol., 49:1228-1235 (2009).
Tartaglia et al., "Identification and expression cloning of a leptin receptor, OB-R," Cell, 83:1263-1271 (1995).
Tomlinson et al., "Transgenic Mice Expressing Human Fibroblast Growth Factor-19 Display Increased Metabolic Rate and Decreased Adiposity," Endocrinology 143(5):1741-47 (2002).
Wang et al., "Leptin in hepatocellular carcinoma," World J. Gastroenterol., 16:5801-5809 (2010).
Zhang et al., "Adenovirus-adeno-associated virus hybrid for large-scale recombinant adeno-associated virus production," Hum. Gene Ther., 20:922-929 (2009).
Aranha et al., "Bile acid levels are increased in the liver of patients with steatohepatitis," Eur. J. Gastroenterol. Hepatol. 20(6): 519-525 (2008).
Beuers et al., "Medical treatment of primary sclerosing cholangitis: a role for novel bile acids and other (post—) transcriptional modulators?", Clin. Rev. Allergy lmmunol., 36(1):52-61 (2009).
Chazouilleres, "Primary sclerosing cholangitis and bile acids," Clinics and Research in Hepatology and Gastroenterology 36:S21-S25 (2012).
Lindor, "Ursodeoxycholic acid for the treatment of primary biliary cirrhosis," New Engl J Med, 11(357; 15) 1524-1529 (2007).
Pusl et al., "Intrahepatic cholestasis of pregnancy," Orphanet Journal of Rare Diseases 2:26 (2007).
Rossi et al., "P1313 Ngm282, a Novel Specific Inhibitor of Cyp7a1-Mediated Bile Acid Synthesis, is Safe and Well Tolerated with Predictable Pharmacokinetics in Healthy Human Subjects," Journal of Hepatology, 60 (1): S533 (2014).
Zhou et al., "Separating Tumorigenicity from Bile Acid Regulatory Activity for Endocrine Hormone FGF19," Cancer Research, 74 (12): 3306-3316 (2014).
Zhou et al., "Engineered fibroblast growth factor 19 reduces liver injury and resolves sclerosing cholangitis in Mdr2-deficient mice," Hepatology, 63 (3): 914-929 (2016).

```
SEQUENCE LISTING

<160> NUMBER OF SEQ ID NOS: 192

<210> SEQ ID NO 1
<211> LENGTH: 194
<212> TYPE: PRT
<213> ORGANISM: Homo sapiens

<400> SEQUENCE: 1

Arg Pro Leu Ala Phe Ser Asp Ala Ser Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
                100                 105                 110
```

```
Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 2
<211> LENGTH: 194
<212> TYPE: PRT
<213> ORGANISM: Homo sapiens

<400> SEQUENCE: 2

Arg Pro Leu Ala Phe Ser Asp Ser Ser Pro Leu Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser His Phe Leu
        130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 3
<211> LENGTH: 194
<212> TYPE: PRT
<213> ORGANISM: Homo sapiens

<400> SEQUENCE: 3

Arg Pro Leu Ala Phe Ser Asp Ala Gly Pro His Val Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45
```

-continued

Ala Arg Gly Gln Ser Ala His Ser Leu Leu Glu Ile Lys Ala Val Ala
            50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Leu Glu Asp Gly Tyr Asn Val Tyr
                100                 105                 110

Arg Ser Glu Lys His Arg Leu Pro Val Ser Leu Ser Ser Ala Lys Gln
                115                 120                 125

Arg Gln Leu Tyr Lys Asn Arg Gly Phe Leu Pro Leu Ser His Phe Leu
            130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 4
<211> LENGTH: 194
<212> TYPE: PRT
<213> ORGANISM: Homo sapiens

<400> SEQUENCE: 4

Arg Pro Leu Ala Phe Ser Asp Ala Gly Pro His Val His Tyr Ala Trp
 1               5                  10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
            50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
                100                 105                 110

Arg Ser Glu Lys His Arg Leu Pro Val Ser Leu Ser Ser Ala Lys Gln
                115                 120                 125

Arg Gln Leu Tyr Lys Asn Arg Gly Phe Leu Pro Leu Ser His Phe Leu
            130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys

<210> SEQ ID NO 5
<211> LENGTH: 191

<212> TYPE: PRT
<213> ORGANISM: Homo sapiens

<400> SEQUENCE: 5

```
Arg His Pro Ile Pro Asp Ser Ser Pro Leu Leu Gln Phe Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 6
<211> LENGTH: 187
<212> TYPE: PRT
<213> ORGANISM: Homo sapiens

<400> SEQUENCE: 6

```
Arg Asp Ser Ser Pro Leu Leu Gln Phe Gly Gly Gln Val Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
    50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160
```

```
Ser Pro Leu Glu Thr Asp Ser Met Asp Pro Phe Gly Leu Val Thr Gly
            165                 170                 175

Leu Glu Ala Val Arg Ser Pro Ser Phe Glu Lys
        180                 185

<210> SEQ ID NO 7
<211> LENGTH: 192
<212> TYPE: PRT
<213> ORGANISM: Homo sapiens

<400> SEQUENCE: 7

Arg Pro Leu Ala Phe Ser Asp Ser Ser Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 8
<211> LENGTH: 191
<212> TYPE: PRT
<213> ORGANISM: Homo sapiens

<400> SEQUENCE: 8

Arg His Pro Ile Pro Asp Ser Ser Pro Leu Leu Gln Trp Gly Asp Pro
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110
```

```
Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190
```

<210> SEQ ID NO 9
<211> LENGTH: 193
<212> TYPE: PRT
<213> ORGANISM: Homo sapiens

<400> SEQUENCE: 9

```
Arg His Pro Ile Pro Asp Ser Ser Pro Leu Leu Gln Phe Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys
```

<210> SEQ ID NO 10
<211> LENGTH: 193
<212> TYPE: PRT
<213> ORGANISM: Homo sapiens

<400> SEQUENCE: 10

```
Arg His Pro Ile Pro Asp Ser Ser Pro His Val His Tyr Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
```

```
                    50                  55                  60
Arg Thr Val Ala Ile Lys Gly Val His Ser Val Arg Tyr Leu Cys Met
 65                  70                  75                  80

Gly Ala Asp Gly Lys Met Gln Gly Leu Leu Gln Tyr Ser Glu Glu Asp
                 85                  90                  95

Cys Ala Phe Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 11
<211> LENGTH: 192
<212> TYPE: PRT
<213> ORGANISM: Homo sapiens

<400> SEQUENCE: 11

Arg Pro Leu Ala Phe Ser Asp Ala Gly Pro Leu Leu Gln Trp Gly Asp
 1               5                  10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
                35                  40                  45

Gly Gln Ser Ala His Ser Leu Leu Glu Ile Lys Ala Val Ala Leu Arg
         50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 12
<211> LENGTH: 194
<212> TYPE: PRT
<213> ORGANISM: Homo sapiens

<400> SEQUENCE: 12
```

Arg Pro Leu Ala Phe Ser Asp Ala Gly Pro Leu Leu Gln Phe Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 13
<211> LENGTH: 192
<212> TYPE: PRT
<213> ORGANISM: Homo sapiens

<400> SEQUENCE: 13

Arg Pro Leu Ala Phe Ser Asp Ala Gly Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

```
Gly Leu Val Thr Gly Leu Glu Ala Val Arg Ser Pro Ser Phe Glu Lys
            180                 185                 190

<210> SEQ ID NO 14
<211> LENGTH: 191
<212> TYPE: PRT
<213> ORGANISM: Homo sapiens

<400> SEQUENCE: 14

Arg His Pro Ile Pro Asp Ser Ser Pro His Val His Tyr Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 15
<211> LENGTH: 192
<212> TYPE: PRT
<213> ORGANISM: Homo sapiens

<400> SEQUENCE: 15

Arg Pro Leu Ala Phe Ser Asp Ala Gly Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125
```

Leu Tyr Lys Asn Arg Gly Phe Leu Pro Leu Ser His Phe Leu Pro Met
            130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
            165                 170                 175

Gly Leu Val Thr Gly Leu Glu Ala Val Arg Ser Pro Ser Phe Glu Lys
            180                 185                 190

<210> SEQ ID NO 16
<211> LENGTH: 192
<212> TYPE: PRT
<213> ORGANISM: Homo sapiens

<400> SEQUENCE: 16

Arg Pro Leu Ala Phe Ser Asp Ala Gly Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 17
<211> LENGTH: 192
<212> TYPE: PRT
<213> ORGANISM: Homo sapiens

<400> SEQUENCE: 17

Arg Pro Leu Ala Phe Ser Asp Ala Gly Pro His Val Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

```
Ala Asp Gly Lys Met Gln Gly Leu Leu Gln Tyr Ser Glu Glu Asp Cys
            85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 18
<211> LENGTH: 192
<212> TYPE: PRT
<213> ORGANISM: Homo sapiens

<400> SEQUENCE: 18

Arg Pro Leu Ala Phe Ser Asp Ala Gly Pro His Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
            85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 19
<211> LENGTH: 192
<212> TYPE: PRT
<213> ORGANISM: Homo sapiens

<400> SEQUENCE: 19

Arg Pro Leu Ala Phe Ser Asp Ala Gly Pro Val Tyr Gly Trp Gly Asp
1               5                   10                  15

Pro Ile Arg Leu Arg His Leu Tyr Thr Ser Gly Pro His Gly Leu Ser
            20                  25                  30
```

```
Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
 50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
             100                 105                 110

Glu Lys His Arg Leu Pro Val Ser Leu Ser Ser Ala Lys Gln Arg Gln
         115                 120                 125

Leu Tyr Lys Asn Arg Gly Phe Leu Pro Leu Ser His Phe Leu Pro Met
    130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 20
<211> LENGTH: 192
<212> TYPE: PRT
<213> ORGANISM: Homo sapiens

<400> SEQUENCE: 20

Arg Pro Leu Ala Phe Ser Asp Ala Gly Pro Val His Gly Trp Gly Asp
1               5                  10                  15

Pro Ile Arg Leu Arg His Leu Tyr Thr Ser Gly Pro His Gly Leu Ser
             20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
 50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
             100                 105                 110

Glu Lys His Arg Leu Pro Val Ser Leu Ser Ser Ala Lys Gln Arg Gln
         115                 120                 125

Leu Tyr Lys Asn Arg Gly Phe Leu Pro Leu Ser His Phe Leu Pro Met
    130                 135                 140

Leu Pro Met Val Pro Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 21
<211> LENGTH: 192
<212> TYPE: PRT
```

<213> ORGANISM: Homo sapiens

<400> SEQUENCE: 21

```
Arg Pro Leu Ala Phe Ser Asp Ala Gly Pro Val His Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 22
<211> LENGTH: 193
<212> TYPE: PRT
<213> ORGANISM: Homo sapiens

<400> SEQUENCE: 22

```
Arg Pro Leu Ala Phe Ser Asp Ala Gly Pro His Val His Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
```

```
                        165                 170                 175

Phe Gly Leu Val Thr Gly Leu Glu Ala Val Arg Ser Pro Ser Phe Glu
                180                 185                 190

Lys

<210> SEQ ID NO 23
<211> LENGTH: 192
<212> TYPE: PRT
<213> ORGANISM: Homo sapiens

<400> SEQUENCE: 23

Arg Pro Leu Ala Phe Ser Asp Ala Gly Pro His His Gly Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 24
<211> LENGTH: 192
<212> TYPE: PRT
<213> ORGANISM: Homo sapiens

<400> SEQUENCE: 24

Arg Pro Leu Ala Phe Ser Asp Ala Gly Pro His His Tyr Trp Gly Asp
1               5                   10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110
```

```
Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 25
<211> LENGTH: 192
<212> TYPE: PRT
<213> ORGANISM: Homo sapiens

<400> SEQUENCE: 25

Arg Pro Leu Ala Phe Ser Asp Ala Gly Pro His Val Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 26
<211> LENGTH: 192
<212> TYPE: PRT
<213> ORGANISM: Homo sapiens

<400> SEQUENCE: 26

Arg Pro Leu Ala Phe Ser Asp Ser Ser Pro Leu Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60
```

-continued

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 27
<211> LENGTH: 192
<212> TYPE: PRT
<213> ORGANISM: Homo sapiens

<400> SEQUENCE: 27

Arg Pro Leu Ala Phe Ser Asp Ser Ser Pro His Val His Trp Gly Asp
 1               5                  10                  15

Pro Ile Arg Leu Arg His Leu Tyr Thr Ser Gly Pro His Gly Leu Ser
                20                  25                  30

Ser Cys Phe Leu Arg Ile Arg Ala Asp Gly Val Val Asp Cys Ala Arg
            35                  40                  45

Gly Gln Ser Ala His Ser Leu Leu Glu Ile Lys Ala Val Ala Leu Arg
        50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 28
<211> LENGTH: 191
<212> TYPE: PRT
<213> ORGANISM: Homo sapiens

<400> SEQUENCE: 28

Arg Pro Leu Ala Phe Ser Asp Ala Gly Pro His Val Trp Gly Asp Pro
 1               5                  10                  15

```
Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 29
<211> LENGTH: 193
<212> TYPE: PRT
<213> ORGANISM: Homo sapiens

<400> SEQUENCE: 29

Arg Pro Leu Ala Phe Ser Asp Ala Gly Pro His Val His Tyr Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
                100                 105                 110

Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys
```

```
<210> SEQ ID NO 30
<211> LENGTH: 194
<212> TYPE: PRT
<213> ORGANISM: Homo sapiens

<400> SEQUENCE: 30

Arg Pro Leu Ala Phe Ser Asp Ala Gly Pro His Val His Tyr Ala Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
        50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 31
<211> LENGTH: 191
<212> TYPE: PRT
<213> ORGANISM: Homo sapiens

<400> SEQUENCE: 31

Arg His Pro Ile Pro Asp Ser Ser Pro Leu Leu Gln Phe Gly Ala Gln
1               5                   10                  15

Val Arg Leu Arg His Leu Tyr Thr Ser Gly Pro His Gly Leu Ser Ser
                20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125
```

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 32
<211> LENGTH: 191
<212> TYPE: PRT
<213> ORGANISM: Homo sapiens

<400> SEQUENCE: 32

Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 33
<211> LENGTH: 191
<212> TYPE: PRT
<213> ORGANISM: Homo sapiens

<400> SEQUENCE: 33

Arg His Pro Ile Pro Asp Ser Ser Pro Leu Leu Gln Phe Gly Pro Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

```
Asp Gly Lys Met Gln Gly Leu Leu Gln Tyr Ser Glu Glu Asp Cys Ala
            85                  90                  95

Phe Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 34
<211> LENGTH: 191
<212> TYPE: PRT
<213> ORGANISM: Homo sapiens

<400> SEQUENCE: 34

Arg His Pro Ile Pro Asp Ser Ser Pro Leu Leu Gln Phe Gly Gly Ala
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
            85                  90                  95

Phe Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 35
<211> LENGTH: 191
<212> TYPE: PRT
<213> ORGANISM: Homo sapiens

<400> SEQUENCE: 35

Arg His Pro Ile Pro Asp Ser Ser Pro Leu Leu Gln Phe Gly Gly Glu
1               5                   10                  15

Val Arg Leu Arg His Leu Tyr Thr Ser Gly Pro His Gly Leu Ser Ser
            20                  25                  30
```

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
 50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 36
<211> LENGTH: 191
<212> TYPE: PRT
<213> ORGANISM: Homo sapiens

<400> SEQUENCE: 36

Arg His Pro Ile Pro Asp Ser Ser Pro Leu Leu Gln Phe Gly Gly Asn
 1               5                  10                  15

Val Arg Leu Arg His Leu Tyr Thr Ser Gly Pro His Gly Leu Ser Ser
             20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
 50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 37
<211> LENGTH: 191
<212> TYPE: PRT
<213> ORGANISM: Homo sapiens

<400> SEQUENCE: 37

```
Arg His Pro Ile Pro Asp Ser Ser Pro Leu Leu Gln Phe Gly Gly Gln
1               5                   10                  15

Ala Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 38
<211> LENGTH: 191
<212> TYPE: PRT
<213> ORGANISM: Homo sapiens

<400> SEQUENCE: 38

```
Arg His Pro Ile Pro Asp Ser Ser Pro Leu Leu Gln Phe Gly Gly Gln
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175
```

```
Leu Val Thr Gly Leu Glu Ala Val Arg Ser Pro Ser Phe Glu Lys
            180                 185                 190

<210> SEQ ID NO 39
<211> LENGTH: 191
<212> TYPE: PRT
<213> ORGANISM: Homo sapiens

<400> SEQUENCE: 39

Arg His Pro Ile Pro Asp Ser Ser Pro Leu Leu Gln Phe Gly Gly Gln
1               5                   10                  15

Thr Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 40
<211> LENGTH: 193
<212> TYPE: PRT
<213> ORGANISM: Homo sapiens

<400> SEQUENCE: 40

Arg His Pro Ile Pro Asp Ser Ser Pro Leu Leu Gln Phe Gly Trp Gly
1               5                   10                  15

Gln Pro Val Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125
```

```
Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 41
<211> LENGTH: 182
<212> TYPE: PRT
<213> ORGANISM: Homo sapiens

<400> SEQUENCE: 41

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 42
<211> LENGTH: 178
<212> TYPE: PRT
<213> ORGANISM: Homo sapiens

<400> SEQUENCE: 42

His Pro Ile Pro Asp Ser Ser Pro Leu Leu Gln Phe Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60
```

```
Ala Ile Lys Gly Val His Ser Val Arg Tyr Leu Cys Met Gly Ala Asp
 65                  70                  75                  80

Gly Lys Met Gln Gly Leu Leu Gln Tyr Ser Glu Glu Asp Cys Ala Phe
                 85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Glu Pro Pro Gly Ile Leu Ala Pro Gln Pro Pro Asp Val Gly Ser Ser
145                 150                 155                 160

Asp Pro Leu Ser Met Val Gly Pro Ser Gln Gly Arg Ser Pro Ser Tyr
                165                 170                 175

Ala Ser

<210> SEQ ID NO 43
<211> LENGTH: 192
<212> TYPE: PRT
<213> ORGANISM: Homo sapiens

<400> SEQUENCE: 43

Arg Pro Leu Ala Phe Ser Asp Ala Gly Pro His Val His Tyr Gly Gly
 1               5                  10                  15

Asp Ile Arg Leu Arg His Leu Tyr Thr Ser Gly Pro His Gly Leu Ser
                 20                  25                  30

Ser Cys Phe Leu Arg Ile Arg Ala Asp Gly Val Val Asp Cys Ala Arg
             35                  40                  45

Gly Gln Ser Ala His Ser Leu Leu Glu Ile Lys Ala Val Ala Leu Arg
         50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 44
<211> LENGTH: 185
<212> TYPE: PRT
<213> ORGANISM: Homo sapiens

<400> SEQUENCE: 44

Arg Pro Leu Ala Phe Ser Asp Ala Gly Pro His Val His Tyr Gly Trp
 1               5                  10                  15

Gly Asp Pro Ile Arg Gln Arg Tyr Leu Tyr Thr Asp Asp Ala Gln Gln
```

```
            20                  25                  30
Thr Glu Ala His Leu Glu Ile Arg Glu Asp Gly Thr Val Gly Gly Ala
        35                  40                  45
Ala Asp Gln Ser Pro Glu Ser Leu Leu Gln Leu Lys Ala Leu Lys Pro
    50                  55                  60
Gly Val Ile Gln Ile Leu Gly Val Lys Thr Ser Arg Phe Leu Cys Gln
65                  70                  75                  80
Arg Pro Asp Gly Ala Leu Tyr Gly Ser Leu His Phe Asp Pro Glu Ala
                85                  90                  95
Cys Ser Phe Arg Glu Leu Leu Leu Glu Asp Gly Tyr Asn Val Tyr Gln
            100                 105                 110
Ser Glu Ala His Gly Leu Pro Leu His Leu Pro Gly Asn Lys Ser Pro
        115                 120                 125
His Arg Asp Pro Ala Pro Arg Gly Pro Ala Arg Phe Leu Pro Leu Pro
    130                 135                 140
Gly Leu Pro Pro Ala Leu Pro Glu Pro Pro Gly Ile Leu Ala Pro Gln
145                 150                 155                 160
Pro Pro Asp Val Gly Ser Ser Asp Pro Leu Ser Met Val Gly Pro Ser
                165                 170                 175
Gln Gly Arg Ser Pro Ser Tyr Ala Ser
                180                 185

<210> SEQ ID NO 45
<211> LENGTH: 193
<212> TYPE: PRT
<213> ORGANISM: Homo sapiens

<400> SEQUENCE: 45

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
                20                  25                  30
Leu Glu Ile Arg Glu Asp Gly Thr Val Gly Gly Ala Ala Asp Gln Ser
            35                  40                  45
Pro Glu Ser Leu Leu Gln Leu Lys Ala Leu Lys Pro Gly Val Ile Gln
        50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Met Val Pro Glu Glu Pro Glu Asp Leu Arg Gly His Leu
145                 150                 155                 160
Glu Ser Asp Met Phe Ser Ser Pro Leu Glu Thr Asp Ser Met Asp Pro
                165                 170                 175
Phe Gly Leu Val Thr Gly Leu Glu Ala Val Arg Ser Pro Ser Phe Glu
            180                 185                 190

Lys
```

```
<210> SEQ ID NO 46
<211> LENGTH: 232
<212> TYPE: PRT
<213> ORGANISM: Homo sapiens

<400> SEQUENCE: 46

Arg Pro Leu Ala Phe Ser Asp Ala Gly Pro His Val His Tyr Gly Trp
1               5                   10                  15

Gly Asp Pro Ile Arg Gln Arg Tyr Leu Tyr Thr Asp Asp Ala Gln Gln
                20                  25                  30

Thr Glu Ala His Leu Glu Ile Arg Glu Asp Gly Thr Val Gly Gly Ala
            35                  40                  45

Ala Asp Gln Ser Pro Glu Ser Leu Leu Gln Leu Lys Ala Leu Lys Pro
    50                  55                  60

Gly Val Ile Gln Ile Leu Gly Val Lys Thr Ser Arg Phe Leu Cys Gln
65                  70                  75                  80

Arg Pro Asp Gly Ala Leu Tyr Gly Ser Leu His Phe Asp Pro Glu Ala
                85                  90                  95

Cys Ser Phe Arg Glu Leu Leu Leu Glu Asp Gly Tyr Asn Val Tyr Gln
                100                 105                 110

Ser Glu Ala His Gly Leu Pro Leu His Leu Pro Gly Asn Lys Ser Pro
            115                 120                 125

His Arg Asp Pro Ala Pro Arg Gly Pro Ala Arg Phe Leu Pro Leu Pro
    130                 135                 140

Gly Leu Pro Pro Ala Leu Pro Glu Pro Pro Gly Ile Leu Ala Pro Gln
145                 150                 155                 160

Pro Pro Asp Val Gly Ser Ser Asp Pro Leu Ser Met Val Gly Pro Ser
                165                 170                 175

Gln Gly Arg Ser Pro Ser Tyr Ala Ser Pro Met Val Pro Glu Glu Pro
                180                 185                 190

Glu Asp Leu Arg Gly His Leu Glu Ser Asp Met Phe Ser Ser Pro Leu
            195                 200                 205

Glu Thr Asp Ser Met Asp Pro Phe Gly Leu Val Thr Gly Leu Glu Ala
    210                 215                 220

Val Arg Ser Pro Ser Phe Glu Lys
225                 230

<210> SEQ ID NO 47
<211> LENGTH: 190
<212> TYPE: PRT
<213> ORGANISM: Homo sapiens

<400> SEQUENCE: 47

His Pro Ile Pro Asp Ser Ser Pro Leu Leu Gln Trp Gly Asp Pro Ile
1               5                   10                  15

Arg Leu Arg His Leu Tyr Thr Ser Gly Pro His Gly Leu Ser Ser Cys
                20                  25                  30

Phe Leu Arg Ile Arg Ala Asp Gly Val Val Asp Cys Ala Arg Gly Gln
            35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
```

```
                    100                 105                  110
His Arg Leu Pro Val Ser Leu Ser Ser Ala Lys Gln Arg Gln Leu Tyr
            115                 120                 125
Lys Asn Arg Gly Phe Leu Pro Leu Ser His Phe Leu Pro Met Leu Pro
        130                 135                 140
Met Val Pro Glu Glu Pro Glu Asp Leu Arg Gly His Leu Glu Ser Asp
145                 150                 155                 160
Met Phe Ser Ser Pro Leu Glu Thr Asp Ser Met Asp Pro Phe Gly Leu
                165                 170                 175
Val Thr Gly Leu Glu Ala Val Arg Ser Pro Ser Phe Glu Lys
            180                 185                 190

<210> SEQ ID NO 48
<211> LENGTH: 187
<212> TYPE: PRT
<213> ORGANISM: Homo sapiens

<400> SEQUENCE: 48

Arg Asp Ser Ser Pro Leu Leu Gln Phe Gly Gly Gln Val Arg Leu Arg
1               5                   10                  15
His Leu Tyr Thr Ser Gly Pro His Gly Leu Ser Ser Cys Phe Leu Arg
            20                  25                  30
Ile Arg Ala Asp Gly Val Val Asp Cys Ala Arg Gly Gln Ser Ala His
        35                  40                  45
Ser Leu Leu Glu Ile Lys Ala Val Ala Leu Arg Thr Val Ala Ile Lys
    50                  55                  60
Gly Val His Ser Val Arg Tyr Leu Cys Met Gly Ala Asp Gly Lys Met
65                  70                  75                  80
Gln Gly Leu Leu Gln Tyr Ser Glu Glu Asp Cys Ala Phe Glu Glu Glu
                85                  90                  95
Ile Arg Pro Asp Gly Tyr Asn Val Tyr Arg Ser Glu Lys His Arg Leu
            100                 105                 110
Pro Val Ser Leu Ser Ser Ala Lys Gln Arg Gln Leu Tyr Lys Asn Arg
        115                 120                 125
Gly Phe Leu Pro Leu Ser His Phe Leu Pro Met Leu Pro Met Val Pro
    130                 135                 140
Glu Glu Pro Glu Asp Leu Arg Gly His Leu Glu Ser Asp Met Phe Ser
145                 150                 155                 160
Ser Pro Leu Glu Thr Asp Ser Met Asp Pro Phe Gly Leu Val Thr Gly
                165                 170                 175
Leu Glu Ala Val Arg Ser Pro Ser Phe Glu Lys
            180                 185

<210> SEQ ID NO 49
<211> LENGTH: 192
<212> TYPE: PRT
<213> ORGANISM: Homo sapiens

<400> SEQUENCE: 49

Arg Pro Leu Ala Phe Ser Asp Ser Ser Pro Leu Leu Gln Phe Gly Gly
1               5                   10                  15
Gln Val Arg Leu Arg His Leu Tyr Thr Ser Gly Pro His Gly Leu Ser
            20                  25                  30
Ser Cys Phe Leu Arg Ile Arg Ala Asp Gly Val Val Asp Cys Ala Arg
        35                  40                  45
Gly Gln Ser Ala His Ser Leu Leu Glu Ile Lys Ala Val Ala Leu Arg
```

```
                    50                  55                  60
Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 50
<211> LENGTH: 191
<212> TYPE: PRT
<213> ORGANISM: Homo sapiens

<400> SEQUENCE: 50

```
Arg His Pro Ile Pro Asp Ser Ser Pro Leu Leu Gln Phe Gly Asp Gln
  1               5                  10                  15

Val Arg Leu Arg His Leu Tyr Thr Ser Gly Pro His Gly Leu Ser Ser
                 20                  25                  30

Cys Phe Leu Arg Ile Arg Ala Asp Gly Val Val Asp Cys Ala Arg Gly
            35                  40                  45

Gln Ser Ala His Ser Leu Leu Glu Ile Lys Ala Val Ala Leu Arg Thr
        50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Leu Glu Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 51
<211> LENGTH: 191
<212> TYPE: PRT
<213> ORGANISM: Homo sapiens

<400> SEQUENCE: 51

Arg His Pro Ile Pro Asp Ser Ser Pro Leu Leu Gln Phe Gly Gly Asn

```
                1               5                  10                 15
            Val Arg Leu Arg His Leu Tyr Thr Ser Gly Pro His Gly Leu Ser Ser
                        20                  25                 30

Cys Phe Leu Arg Ile Arg Ala Asp Gly Val Val Asp Cys Ala Arg Gly
                        35                  40                 45

Gln Ser Ala His Ser Leu Leu Glu Ile Lys Ala Val Ala Leu Arg Thr
                        50                  55                 60

Val Ala Ile Lys Gly Val His Ser Val Arg Tyr Leu Cys Met Gly Ala
            65                  70                  75                 80

Asp Gly Lys Met Gln Gly Leu Leu Gln Tyr Ser Glu Glu Asp Cys Ala
                        85                  90                 95

Phe Glu Glu Glu Ile Arg Pro Asp Gly Tyr Asn Val Tyr Arg Ser Glu
                        100                 105                110

Lys His Arg Leu Pro Val Ser Leu Ser Ser Ala Lys Gln Arg Gln Leu
                        115                 120                125

Tyr Lys Asn Arg Gly Phe Leu Pro Leu Ser His Phe Leu Pro Met Leu
                        130                 135                140

Pro Met Val Pro Glu Glu Pro Glu Asp Leu Arg Gly His Leu Glu Ser
            145                 150                 155                160

Asp Met Phe Ser Ser Pro Leu Glu Thr Asp Ser Met Asp Pro Phe Gly
                        165                 170                175

Leu Val Thr Gly Leu Glu Ala Val Arg Ser Pro Ser Phe Glu Lys
                        180                 185                190

<210> SEQ ID NO 52
            <211> LENGTH: 187
            <212> TYPE: PRT
            <213> ORGANISM: Homo sapiens

<400> SEQUENCE: 52

Arg Asp Ser Ser Pro Leu Leu Gln Trp Gly Asp Pro Ile Arg Leu Arg
            1               5                   10                 15

His Leu Tyr Thr Ser Gly Pro His Gly Leu Ser Ser Cys Phe Leu Arg
                        20                  25                 30

Ile Arg Ala Asp Gly Val Val Asp Cys Ala Arg Gly Gln Ser Ala His
                        35                  40                 45

Ser Leu Leu Glu Ile Lys Ala Val Ala Leu Arg Thr Val Ala Ile Lys
                        50                  55                 60

Gly Val His Ser Val Arg Tyr Leu Cys Met Gly Ala Asp Gly Lys Met
            65                  70                  75                 80

Gln Gly Leu Leu Gln Tyr Ser Glu Glu Asp Cys Ala Phe Glu Glu Glu
                        85                  90                 95

Ile Arg Pro Asp Gly Tyr Asn Val Tyr Arg Ser Glu Lys His Arg Leu
                        100                 105                110

Pro Val Ser Leu Ser Ser Ala Lys Gln Arg Gln Leu Tyr Lys Asn Arg
                        115                 120                125

Gly Phe Leu Pro Leu Ser His Phe Leu Pro Met Leu Pro Met Val Pro
                        130                 135                140

Glu Glu Pro Glu Asp Leu Arg Gly His Leu Glu Ser Asp Met Phe Ser
            145                 150                 155                160

Ser Pro Leu Glu Thr Asp Ser Met Asp Pro Phe Gly Leu Val Thr Gly
                        165                 170                175

Leu Glu Ala Val Arg Ser Pro Ser Phe Glu Lys
                        180                 185
```

<210> SEQ ID NO 53
<211> LENGTH: 189
<212> TYPE: PRT
<213> ORGANISM: Homo sapiens

<400> SEQUENCE: 53

Met Asp Ser Ser Pro Leu Val His Tyr Gly Trp Gly Asp Pro Ile Arg
1               5                   10                  15

Leu Arg His Leu Tyr Thr Ser Gly Pro His Gly Leu Ser Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 54
<211> LENGTH: 192
<212> TYPE: PRT
<213> ORGANISM: Homo sapiens

<400> SEQUENCE: 54

Arg Pro Leu Ala Phe Ser Asp Ala Gly Pro Leu Leu Gln Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

```
Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 55
<211> LENGTH: 192
<212> TYPE: PRT
<213> ORGANISM: Homo sapiens

<400> SEQUENCE: 55

```
Arg Pro Leu Ala Phe Ser Asp Ala Gly Pro His Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 56
<211> LENGTH: 192
<212> TYPE: PRT
<213> ORGANISM: Homo sapiens

<400> SEQUENCE: 56

```
Arg Pro Leu Ala Phe Ser Asp Ala Gly Pro Val Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95
```

```
Ala Phe Glu Glu Ile Arg Pro Asp Gly Tyr Asn Val Tyr Arg Ser
            100                 105                 110

Glu Lys His Arg Leu Pro Val Ser Leu Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 57
<211> LENGTH: 192
<212> TYPE: PRT
<213> ORGANISM: Homo sapiens

<400> SEQUENCE: 57

Arg Pro Leu Ala Phe Ser Asp Ala Gly Pro Val His Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 58
<211> LENGTH: 192
<212> TYPE: PRT
<213> ORGANISM: Homo sapiens

<400> SEQUENCE: 58

Arg Pro Leu Ala Phe Ser Asp Ala Gly Pro Val His Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45
```

```
Gly Gln Ser Ala His Ser Leu Leu Glu Ile Lys Ala Val Ala Leu Arg
         50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
                115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 59
<211> LENGTH: 192
<212> TYPE: PRT
<213> ORGANISM: Homo sapiens

<400> SEQUENCE: 59

Arg Pro Leu Ala Phe Ser Asp Ala Gly Pro His His Gly Trp Gly Asp
 1               5                  10                  15

Pro Ile Arg Leu Arg His Leu Tyr Thr Ser Gly Pro His Gly Leu Ser
                 20                  25                  30

Ser Cys Phe Leu Arg Ile Arg Ala Asp Gly Val Val Asp Cys Ala Arg
             35                  40                  45

Gly Gln Ser Ala His Ser Leu Leu Glu Ile Lys Ala Val Ala Leu Arg
         50                  55                  60

Thr Val Ala Ile Lys Gly Val His Ser Val Arg Tyr Leu Cys Met Gly
 65                  70                  75                  80

Ala Asp Gly Lys Met Gln Gly Leu Leu Gln Tyr Ser Glu Glu Asp Cys
                 85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
                115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 60
<211> LENGTH: 192
<212> TYPE: PRT
<213> ORGANISM: Homo sapiens

<400> SEQUENCE: 60
```

```
Arg Pro Leu Ala Phe Ser Asp Ala Gly Pro His His Tyr Trp Gly Asp
 1               5                  10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 61
<211> LENGTH: 192
<212> TYPE: PRT
<213> ORGANISM: Homo sapiens

<400> SEQUENCE: 61

Arg Pro Leu Ala Phe Ser Asp Ala Gly Pro His Val Gly Trp Gly Asp
 1               5                  10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 62
<211> LENGTH: 192
<212> TYPE: PRT
<213> ORGANISM: Homo sapiens

<400> SEQUENCE: 62

```
Arg Pro Leu Ala Phe Ser Asp Ala Gly Pro His Val Tyr Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190
```

<210> SEQ ID NO 63
<211> LENGTH: 192
<212> TYPE: PRT
<213> ORGANISM: Homo sapiens

<400> SEQUENCE: 63

```
Arg Pro Leu Ala Phe Ser Asp Ala Gly Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140
```

```
Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 64
<211> LENGTH: 192
<212> TYPE: PRT
<213> ORGANISM: Homo sapiens

<400> SEQUENCE: 64

Arg Pro Leu Ala Phe Ser Asp Ser Ser Pro Leu Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 65
<211> LENGTH: 192
<212> TYPE: PRT
<213> ORGANISM: Homo sapiens

<400> SEQUENCE: 65

Arg Pro Leu Ala Phe Ser Asp Ser Ser Pro His Val His Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95
```

```
Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 66
<211> LENGTH: 192
<212> TYPE: PRT
<213> ORGANISM: Homo sapiens

<400> SEQUENCE: 66

Arg Pro Leu Ala Phe Ser Asp Ala Gly Pro His Leu Gln Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
        130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 67
<211> LENGTH: 191
<212> TYPE: PRT
<213> ORGANISM: Homo sapiens

<400> SEQUENCE: 67

Arg Pro Leu Ala Phe Ser Asp Ala Gly Pro His Val Trp Gly Asp Pro
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45
```

```
Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 68
<211> LENGTH: 193
<212> TYPE: PRT
<213> ORGANISM: Homo sapiens

<400> SEQUENCE: 68

Arg Pro Leu Ala Phe Ser Asp Ala Gly Pro His Val His Tyr Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 69
<211> LENGTH: 189
<212> TYPE: PRT
<213> ORGANISM: Homo sapiens
```

<400> SEQUENCE: 69

```
Arg Asp Ser Ser Pro Leu Val His Tyr Gly Trp Gly Asp Pro Ile Arg
1               5                   10                  15

Leu Arg His Leu Tyr Thr Ser Gly Pro His Gly Leu Ser Ser Cys Phe
            20                  25                  30

Leu Arg Ile Arg Ala Asp Gly Val Val Asp Cys Ala Arg Gly Gln Ser
        35                  40                  45

Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
65                  70                  75                  80

Lys Met Gln Gly Leu Leu Gln Tyr Ser Glu Glu Asp Cys Ala Phe Glu
                85                  90                  95

Glu Glu Ile Arg Pro Asp Gly Tyr Asn Val Tyr Arg Ser Glu Lys His
            100                 105                 110

Arg Leu Pro Val Ser Leu Ser Ser Ala Lys Gln Arg Gln Leu Tyr Lys
        115                 120                 125

Asn Arg Gly Phe Leu Pro Leu Ser His Phe Leu Pro Met Leu Pro Met
    130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185
```

<210> SEQ ID NO 70
<211> LENGTH: 190
<212> TYPE: PRT
<213> ORGANISM: Homo sapiens

<400> SEQUENCE: 70

```
Met Arg Asp Ser Ser Pro Leu Val His Tyr Gly Trp Gly Asp Pro Ile
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175
```

```
Val Thr Gly Leu Glu Ala Val Arg Ser Pro Ser Phe Glu Lys
        180                 185                 190

<210> SEQ ID NO 71
<211> LENGTH: 181
<212> TYPE: PRT
<213> ORGANISM: Homo sapiens

<400> SEQUENCE: 71

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Ser Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 72
<211> LENGTH: 181
<212> TYPE: PRT
<213> ORGANISM: Homo sapiens

<400> SEQUENCE: 72

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125
```

```
Ala Pro Arg Gly Pro Ala Arg Phe Leu Pro Leu Pro Gly Leu Pro Pro
        130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 73
<211> LENGTH: 212
<212> TYPE: PRT
<213> ORGANISM: Homo sapiens

<400> SEQUENCE: 73

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Val Gln Asp Glu Leu Gln Gly
                165                 170                 175

Val Gly Gly Glu Gly Cys His Met His Pro Glu Asn Cys Lys Thr Leu
            180                 185                 190

Leu Thr Asp Ile Asp Arg Thr His Thr Glu Lys Pro Val Trp Asp Gly
        195                 200                 205

Ile Thr Gly Glu
    210

<210> SEQ ID NO 74
<211> LENGTH: 189
<212> TYPE: PRT
<213> ORGANISM: Homo sapiens

<400> SEQUENCE: 74

Arg Asp Ala Gly Pro His Val His Tyr Gly Trp Gly Asp Pro Ile Arg
1               5                   10                  15

Leu Arg His Leu Tyr Thr Ser Gly Pro His Gly Leu Ser Ser Cys Phe
            20                  25                  30

Leu Arg Ile Arg Ala Asp Gly Val Val Asp Cys Ala Arg Gly Gln Ser
        35                  40                  45
```

```
Ala His Ser Leu Leu Glu Ile Lys Ala Val Ala Leu Arg Thr Val Ala
    50                  55                  60

Ile Lys Gly Val His Ser Val Arg Tyr Leu Cys Met Gly Ala Asp Gly
 65                  70                  75                  80

Lys Met Gln Gly Leu Leu Gln Tyr Ser Glu Glu Asp Cys Ala Phe Glu
                     85                  90                  95

Glu Glu Ile Arg Pro Asp Gly Tyr Asn Val Tyr Arg Ser Glu Lys His
                100                 105                 110

Arg Leu Pro Val Ser Leu Ser Ser Ala Lys Gln Arg Gln Leu Tyr Lys
            115                 120                 125

Asn Arg Gly Phe Leu Pro Leu Ser His Phe Leu Pro Met Leu Pro Met
        130                 135                 140

Val Pro Glu Glu Pro Glu Asp Leu Arg Gly His Leu Glu Ser Asp Met
145                 150                 155                 160

Phe Ser Ser Pro Leu Glu Thr Asp Ser Met Asp Pro Phe Gly Leu Val
                165                 170                 175

Thr Gly Leu Glu Ala Val Arg Ser Pro Ser Phe Glu Lys
            180                 185

<210> SEQ ID NO 75
<211> LENGTH: 184
<212> TYPE: PRT
<213> ORGANISM: Homo sapiens

<400> SEQUENCE: 75

Arg Val His Tyr Gly Trp Gly Asp Pro Ile Arg Leu Arg His Leu Tyr
 1               5                  10                  15

Thr Ser Gly Pro His Gly Leu Ser Ser Cys Phe Leu Arg Ile Arg Ala
                20                  25                  30

Asp Gly Val Val Asp Cys Ala Arg Gly Gln Ser Ala His Ser Leu Leu
            35                  40                  45

Glu Ile Lys Ala Val Ala Leu Arg Thr Val Ala Ile Lys Gly Val His
    50                  55                  60

Ser Val Arg Tyr Leu Cys Met Gly Ala Asp Gly Lys Met Gln Gly Leu
 65                  70                  75                  80

Leu Gln Tyr Ser Glu Glu Asp Cys Ala Phe Glu Glu Glu Ile Arg Pro
                 85                 90                  95

Asp Gly Tyr Asn Val Tyr Arg Ser Glu Lys His Arg Leu Pro Val Ser
                100                 105                 110

Leu Ser Ser Ala Lys Gln Arg Gln Leu Tyr Lys Asn Arg Gly Phe Leu
            115                 120                 125

Pro Leu Ser His Phe Leu Pro Met Leu Pro Met Val Pro Glu Glu Pro
        130                 135                 140

Glu Asp Leu Arg Gly His Leu Glu Ser Asp Met Phe Ser Ser Pro Leu
145                 150                 155                 160

Glu Thr Asp Ser Met Asp Pro Phe Gly Leu Val Thr Gly Leu Glu Ala
                165                 170                 175

Val Arg Ser Pro Ser Phe Glu Lys
            180

<210> SEQ ID NO 76
<211> LENGTH: 179
<212> TYPE: PRT
<213> ORGANISM: Homo sapiens

<400> SEQUENCE: 76
```

```
Arg Gly Asp Pro Ile Arg Leu Arg His Leu Tyr Thr Ser Gly Pro His
 1               5                  10                  15

Gly Leu Ser Ser Cys Phe Leu Arg Ile Arg Ala Asp Gly Val Val Asp
            20                  25                  30

Cys Ala Arg Gly Gln Ser Ala His Ser Leu Leu Glu Ile Lys Ala Val
        35                  40                  45

Ala Leu Arg Thr Val Ala Ile Lys Gly Val His Ser Val Arg Tyr Leu
    50                  55                  60

Cys Met Gly Ala Asp Gly Lys Met Gln Gly Leu Leu Gln Tyr Ser Glu
65                  70                  75                  80

Glu Asp Cys Ala Phe Glu Glu Glu Ile Arg Pro Asp Gly Tyr Asn Val
                85                  90                  95

Tyr Arg Ser Glu Lys His Arg Leu Pro Val Ser Leu Ser Ser Ala Lys
            100                 105                 110

Gln Arg Gln Leu Tyr Lys Asn Arg Gly Phe Leu Pro Leu Ser His Phe
        115                 120                 125

Leu Pro Met Leu Pro Met Val Pro Glu Glu Pro Glu Asp Leu Arg Gly
    130                 135                 140

His Leu Glu Ser Asp Met Phe Ser Ser Pro Leu Glu Thr Asp Ser Met
145                 150                 155                 160

Asp Pro Phe Gly Leu Val Thr Gly Leu Glu Ala Val Arg Ser Pro Ser
                165                 170                 175

Phe Glu Lys

<210> SEQ ID NO 77
<211> LENGTH: 175
<212> TYPE: PRT
<213> ORGANISM: Homo sapiens

<400> SEQUENCE: 77

Arg Arg Leu Arg His Leu Tyr Thr Ser Gly Pro His Gly Leu Ser Ser
 1               5                  10                  15

Cys Phe Leu Arg Ile Arg Ala Asp Gly Val Val Asp Cys Ala Arg Gly
            20                  25                  30

Gln Ser Ala His Ser Leu Leu Glu Ile Lys Ala Val Ala Leu Arg Thr
        35                  40                  45

Val Ala Ile Lys Gly Val His Ser Val Arg Tyr Leu Cys Met Gly Ala
    50                  55                  60

Asp Gly Lys Met Gln Gly Leu Leu Gln Tyr Ser Glu Glu Asp Cys Ala
65                  70                  75                  80

Phe Glu Glu Glu Ile Arg Pro Asp Gly Tyr Asn Val Tyr Arg Ser Glu
                85                  90                  95

Lys His Arg Leu Pro Val Ser Leu Ser Ser Ala Lys Gln Arg Gln Leu
            100                 105                 110

Tyr Lys Asn Arg Gly Phe Leu Pro Leu Ser His Phe Leu Pro Met Leu
        115                 120                 125

Pro Met Val Pro Glu Glu Pro Glu Asp Leu Arg Gly His Leu Glu Ser
    130                 135                 140

Asp Met Phe Ser Ser Pro Leu Glu Thr Asp Ser Met Asp Pro Phe Gly
145                 150                 155                 160

Leu Val Thr Gly Leu Glu Ala Val Arg Ser Pro Ser Phe Glu Lys
                165                 170                 175

<210> SEQ ID NO 78
```

<211> LENGTH: 188
<212> TYPE: PRT
<213> ORGANISM: Homo sapiens

<400> SEQUENCE: 78

```
Arg Ala Gly Pro His Val His Tyr Gly Trp Gly Asp Pro Ile Arg Leu
1               5                   10                  15

Arg His Leu Tyr Thr Ser Gly Pro His Gly Leu Ser Ser Cys Phe Leu
            20                  25                  30

Arg Ile Arg Ala Asp Gly Val Val Asp Cys Ala Arg Gly Gln Ser Ala
        35                  40                  45

His Ser Leu Leu Glu Ile Lys Ala Val Ala Leu Arg Thr Val Ala Ile
50                  55                  60

Lys Gly Val His Ser Val Arg Tyr Leu Cys Met Gly Ala Asp Gly Lys
65                  70                  75                  80

Met Gln Gly Leu Leu Gln Tyr Ser Glu Glu Asp Cys Ala Phe Glu Glu
                85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
        115                 120                 125

Arg Gly Phe Leu Pro Leu Ser His Phe Leu Pro Met Leu Pro Met Val
    130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185
```

<210> SEQ ID NO 79
<211> LENGTH: 187
<212> TYPE: PRT
<213> ORGANISM: Homo sapiens

<400> SEQUENCE: 79

```
Arg Gly Pro His Val His Tyr Gly Trp Gly Asp Pro Ile Arg Leu Arg
1               5                   10                  15

His Leu Tyr Thr Ser Gly Pro His Gly Leu Ser Ser Cys Phe Leu Arg
            20                  25                  30

Ile Arg Ala Asp Gly Val Val Asp Cys Ala Arg Gly Gln Ser Ala His
        35                  40                  45

Ser Leu Leu Glu Ile Lys Ala Val Ala Leu Arg Thr Val Ala Ile Lys
50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160
```

```
Ser Pro Leu Glu Thr Asp Ser Met Asp Pro Phe Gly Leu Val Thr Gly
                165                 170                 175

Leu Glu Ala Val Arg Ser Pro Ser Phe Glu Lys
        180                 185

<210> SEQ ID NO 80
<211> LENGTH: 186
<212> TYPE: PRT
<213> ORGANISM: Homo sapiens

<400> SEQUENCE: 80

Arg Pro His Val His Tyr Gly Trp Gly Asp Pro Ile Arg Leu Arg His
1               5                   10                  15

Leu Tyr Thr Ser Gly Pro His Gly Leu Ser Ser Cys Phe Leu Arg Ile
            20                  25                  30

Arg Ala Asp Gly Val Val Asp Cys Ala Arg Gly Gln Ser Ala His Ser
        35                  40                  45

Leu Leu Glu Ile Lys Ala Val Ala Leu Arg Thr Val Ala Ile Lys Gly
    50                  55                  60

Val His Ser Val Arg Tyr Leu Cys Met Gly Ala Asp Gly Lys Met Gln
65                  70                  75                  80

Gly Leu Leu Gln Tyr Ser Glu Glu Asp Cys Ala Phe Glu Glu Glu Ile
                85                  90                  95

Arg Pro Asp Gly Tyr Asn Val Tyr Arg Ser Glu Lys His Arg Leu Pro
            100                 105                 110

Val Ser Leu Ser Ser Ala Lys Gln Arg Gln Leu Tyr Lys Asn Arg Gly
        115                 120                 125

Phe Leu Pro Leu Ser His Phe Leu Pro Met Leu Pro Met Val Pro Glu
    130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 81
<211> LENGTH: 185
<212> TYPE: PRT
<213> ORGANISM: Homo sapiens

<400> SEQUENCE: 81

Arg His Val His Tyr Gly Trp Gly Asp Pro Ile Arg Leu Arg His Leu
1               5                   10                  15

Tyr Thr Ser Gly Pro His Gly Leu Ser Ser Cys Phe Leu Arg Ile Arg
            20                  25                  30

Ala Asp Gly Val Val Asp Cys Ala Arg Gly Gln Ser Ala His Ser Leu
        35                  40                  45

Leu Glu Ile Lys Ala Val Ala Leu Arg Thr Val Ala Ile Lys Gly Val
    50                  55                  60

His Ser Val Arg Tyr Leu Cys Met Gly Ala Asp Gly Lys Met Gln Gly
65                  70                  75                  80

Leu Leu Gln Tyr Ser Glu Glu Asp Cys Ala Phe Glu Glu Glu Ile Arg
                85                  90                  95

Pro Asp Gly Tyr Asn Val Tyr Arg Ser Glu Lys His Arg Leu Pro Val
            100                 105                 110
```

```
Ser Leu Ser Ser Ala Lys Gln Arg Gln Leu Tyr Lys Asn Arg Gly Phe
        115                 120                 125

Leu Pro Leu Ser His Phe Leu Pro Met Leu Pro Met Val Pro Glu Glu
        130                 135                 140

Pro Glu Asp Leu Arg Gly His Leu Glu Ser Asp Met Phe Ser Ser Pro
145                 150                 155                 160

Leu Glu Thr Asp Ser Met Asp Pro Phe Gly Leu Val Thr Gly Leu Glu
                165                 170                 175

Ala Val Arg Ser Pro Ser Phe Glu Lys
            180                 185

<210> SEQ ID NO 82
<211> LENGTH: 194
<212> TYPE: PRT
<213> ORGANISM: Homo sapiens

<400> SEQUENCE: 82

Arg Pro Leu Ala Phe Ser Ala Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 83
<211> LENGTH: 194
<212> TYPE: PRT
<213> ORGANISM: Homo sapiens

<400> SEQUENCE: 83

Arg Pro Leu Ala Phe Ser Asp Ala Ala Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45
```

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 84
<211> LENGTH: 194
<212> TYPE: PRT
<213> ORGANISM: Homo sapiens

<400> SEQUENCE: 84

Arg Pro Leu Ala Phe Ser Asp Ala Gly Ala His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 85
<211> LENGTH: 194
<212> TYPE: PRT

```
<213> ORGANISM: Homo sapiens

<400> SEQUENCE: 85

Arg Pro Leu Ala Phe Ser Asp Ala Gly Pro His Val His Tyr Gly Ala
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 86
<211> LENGTH: 194
<212> TYPE: PRT
<213> ORGANISM: Homo sapiens

<400> SEQUENCE: 86

Arg Pro Leu Ala Phe Ser Asp Ala Gly Pro His Val His Tyr Gly Trp
1               5                   10                  15

Gly Ala Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160
```

```
Leu Glu Ser Asp Met Phe Ser Ser Pro Leu Glu Thr Asp Ser Met Asp
                165                 170                 175
Pro Phe Gly Leu Val Thr Gly Leu Glu Ala Val Arg Ser Pro Ser Phe
            180                 185                 190
Glu Lys

<210> SEQ ID NO 87
<211> LENGTH: 167
<212> TYPE: PRT
<213> ORGANISM: Homo sapiens

<400> SEQUENCE: 87

Arg Pro Leu Ala Phe Ser Asp Ala Gly Pro His Val His Tyr Gly Trp
1               5                   10                  15
Gly Asp Ala Ile Cys Ala Arg Gly Gln Ser Ala His Ser Leu Leu Glu
            20                  25                  30
Ile Lys Ala Val Ala Leu Arg Thr Val Ala Ile Lys Gly Val His Ser
        35                  40                  45
Val Arg Tyr Leu Cys Met Gly Ala Asp Gly Lys Met Gln Gly Leu Leu
    50                  55                  60
Gln Tyr Ser Glu Glu Asp Cys Ala Phe Glu Glu Ile Arg Pro Asp
65                  70                  75                  80
Gly Tyr Asn Val Tyr Arg Ser Glu Lys His Arg Leu Pro Val Ser Leu
                85                  90                  95
Ser Ser Ala Lys Gln Arg Gln Leu Tyr Lys Asn Arg Gly Phe Leu Pro
            100                 105                 110
Leu Ser His Phe Leu Pro Met Leu Pro Met Val Pro Glu Glu Pro Glu
        115                 120                 125
Asp Leu Arg Gly His Leu Glu Ser Asp Met Phe Ser Ser Pro Leu Glu
    130                 135                 140
Thr Asp Ser Met Asp Pro Phe Gly Leu Val Thr Gly Leu Glu Ala Val
145                 150                 155                 160
Arg Ser Pro Ser Phe Glu Lys
                165

<210> SEQ ID NO 88
<211> LENGTH: 194
<212> TYPE: PRT
<213> ORGANISM: Homo sapiens

<400> SEQUENCE: 88

Arg Pro Leu Ala Phe Ser Asp Ala Gly Pro His Val His Tyr Gly Trp
1               5                   10                  15
Gly Asp Pro Ile Arg Leu Arg His Leu Tyr Thr Ser Gly Pro Ala Gly
            20                  25                  30
Leu Ser Ser Cys Phe Leu Arg Ile Arg Ala Asp Gly Val Val Asp Cys
        35                  40                  45
Ala Arg Gly Gln Ser Ala His Ser Leu Leu Glu Ile Lys Ala Val Ala
    50                  55                  60
Leu Arg Thr Val Ala Ile Lys Gly Val His Ser Val Arg Tyr Leu Cys
65                  70                  75                  80
Met Gly Ala Asp Gly Lys Met Gln Gly Leu Leu Gln Tyr Ser Glu Glu
                85                  90                  95
Asp Cys Ala Phe Glu Glu Ile Arg Pro Asp Gly Tyr Asn Val Tyr
            100                 105                 110
```

```
Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ala His Phe Leu
        130                 135                 140

Pro Met Leu Pro Met Val Pro Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 89
<211> LENGTH: 194
<212> TYPE: PRT
<213> ORGANISM: Homo sapiens

<400> SEQUENCE: 89

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro Ala Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
            115                 120                 125

Arg Gln Leu Tyr Lys Asn Arg Gly Phe Leu Pro Leu Ser Ala Phe Leu
        130                 135                 140

Pro Met Leu Pro Met Val Pro Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 90
<211> LENGTH: 194
<212> TYPE: PRT
<213> ORGANISM: Homo sapiens

<400> SEQUENCE: 90

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45
```

```
Ala Arg Gly Gln Ser Ala His Ser Leu Leu Glu Ile Lys Ala Val Ala
     50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ser His Phe Leu
130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 91
<211> LENGTH: 194
<212> TYPE: PRT
<213> ORGANISM: Homo sapiens

<400> SEQUENCE: 91

Arg Pro Leu Ala Phe Ser Asp Ala Gly Pro His Val His Tyr Gly Trp
 1               5                  10                  15

Gly Asp Pro Ile Arg Leu Arg His Leu Tyr Thr Ser Gly Pro His Gly
                 20                  25                  30

Leu Ser Ser Cys Phe Leu Arg Ile Arg Ala Asp Gly Val Val Asp Cys
             35                  40                  45

Ala Arg Gly Gln Ser Ala His Ser Leu Leu Glu Ile Lys Ala Val Ala
     50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Arg Gln Leu Tyr Lys Asn Arg Gly Phe Leu Pro Leu Ala His Phe Leu
130                 135                 140

Pro Met Leu Pro Met Val Pro Glu Gly Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 92
<211> LENGTH: 194
```

```
<212> TYPE: PRT
<213> ORGANISM: Homo sapiens

<400> SEQUENCE: 92

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Arg Gln Leu Tyr Lys Asn Arg Gly Phe Leu Pro Leu Ser Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 93
<211> LENGTH: 194
<212> TYPE: PRT
<213> ORGANISM: Homo sapiens

<400> SEQUENCE: 93

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Ala Gln Leu Tyr Lys Asn Arg Gly Phe Leu Pro Leu Ala His Phe Leu
    130                 135                 140

Pro Met Leu Pro Met Val Pro Glu Glu Pro Glu Asp Leu Arg Gly His
```

```
                 145                 150                 155                 160
Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 94
<211> LENGTH: 194
<212> TYPE: PRT
<213> ORGANISM: Homo sapiens

<400> SEQUENCE: 94

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ala Ala Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 95
<211> LENGTH: 194
<212> TYPE: PRT
<213> ORGANISM: Homo sapiens

<400> SEQUENCE: 95

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80
```

```
Met Gly Ala Asp Gly Lys Met Gln Gly Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ala Ala Gln
        115                 120                 125

Arg Gln Leu Tyr Lys Asn Arg Gly Phe Leu Pro Leu Ser Ala Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 96
<211> LENGTH: 194
<212> TYPE: PRT
<213> ORGANISM: Homo sapiens

<400> SEQUENCE: 96

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ala His Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 97
<211> LENGTH: 194
<212> TYPE: PRT
<213> ORGANISM: Homo sapiens

<400> SEQUENCE: 97

Arg Pro Leu Ala Phe Ser Asp Ala Gly Pro His Val His Tyr Gly Trp
1               5                   10                  15
```

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ser Ala Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 98
<211> LENGTH: 194
<212> TYPE: PRT
<213> ORGANISM: Homo sapiens

<400> SEQUENCE: 98

Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
 50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Ala Gln
        115                 120                 125

Ala Gln Leu Tyr Lys Asn Arg Gly Phe Leu Pro Leu Ala Ala Phe Leu
130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 99
<211> LENGTH: 194
<212> TYPE: PRT
<213> ORGANISM: Homo sapiens

<400> SEQUENCE: 99

```
Arg Pro Leu Ala Phe Ser Asp Ala Gly Pro His Val His Tyr Gly Trp
1               5                   10                  15

Gly Asp Pro Ile Arg Leu Arg His Leu Tyr Thr Ser Gly Pro His Gly
                20                  25                  30

Leu Ser Ser Cys Phe Leu Arg Ile Arg Ala Asp Gly Val Val Asp Cys
            35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Ile Arg Pro Asp Gly Tyr Asn Val Tyr
                100                 105                 110

Arg Ser Glu Lys His Arg Leu Pro Val Ser Leu Ser Ala Lys Gln
            115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
                180                 185                 190

Glu Lys
```

<210> SEQ ID NO 100
<211> LENGTH: 181
<212> TYPE: PRT
<213> ORGANISM: Homo sapiens

<400> SEQUENCE: 100

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
```

```
                    115                 120                 125
Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 101
<211> LENGTH: 4
<212> TYPE: PRT
<213> ORGANISM: Homo sapiens

<400> SEQUENCE: 101

Val His Tyr Gly
1

<210> SEQ ID NO 102
<211> LENGTH: 9
<212> TYPE: PRT
<213> ORGANISM: Homo sapiens

<400> SEQUENCE: 102

Asp Ala Ser Pro His Val His Tyr Gly
1               5

<210> SEQ ID NO 103
<211> LENGTH: 9
<212> TYPE: PRT
<213> ORGANISM: Homo sapiens

<400> SEQUENCE: 103

Asp Ser Ser Pro Leu Val His Tyr Gly
1               5

<210> SEQ ID NO 104
<211> LENGTH: 7
<212> TYPE: PRT
<213> ORGANISM: Homo sapiens

<400> SEQUENCE: 104

Asp Ser Ser Pro Leu Leu Gln
1               5

<210> SEQ ID NO 105
<211> LENGTH: 12
<212> TYPE: PRT
<213> ORGANISM: Homo sapiens

<400> SEQUENCE: 105

Asp Ser Ser Pro Leu Leu Gln Phe Gly Gly Gln Val
1               5                   10

<210> SEQ ID NO 106
<211> LENGTH: 5
<212> TYPE: PRT
<213> ORGANISM: Homo sapiens

<400> SEQUENCE: 106

Arg His Pro Ile Pro
1               5
```

```
<210> SEQ ID NO 107
<211> LENGTH: 4
<212> TYPE: PRT
<213> ORGANISM: Homo sapiens

<400> SEQUENCE: 107

His Pro Ile Pro
1

<210> SEQ ID NO 108
<211> LENGTH: 5
<212> TYPE: PRT
<213> ORGANISM: Homo sapiens

<400> SEQUENCE: 108

Arg Pro Leu Ala Phe
1               5

<210> SEQ ID NO 109
<211> LENGTH: 4
<212> TYPE: PRT
<213> ORGANISM: Homo sapiens

<400> SEQUENCE: 109

Pro Leu Ala Phe
1

<210> SEQ ID NO 110
<211> LENGTH: 6
<212> TYPE: PRT
<213> ORGANISM: Homo sapiens

<400> SEQUENCE: 110

Met Asp Ser Ser Pro Leu
1               5

<210> SEQ ID NO 111
<211> LENGTH: 7
<212> TYPE: PRT
<213> ORGANISM: Homo sapiens

<400> SEQUENCE: 111

Met Ser Asp Ser Ser Pro Leu
1               5

<210> SEQ ID NO 112
<211> LENGTH: 6
<212> TYPE: PRT
<213> ORGANISM: Homo sapiens

<400> SEQUENCE: 112

Ser Asp Ser Ser Pro Leu
1               5

<210> SEQ ID NO 113
<211> LENGTH: 5
<212> TYPE: PRT
<213> ORGANISM: Homo sapiens

<400> SEQUENCE: 113

Met Ser Ser Pro Leu
1               5
```

```
<210> SEQ ID NO 114
<211> LENGTH: 4
<212> TYPE: PRT
<213> ORGANISM: Homo sapiens

<400> SEQUENCE: 114

Ser Ser Pro Leu
1

<210> SEQ ID NO 115
<211> LENGTH: 4
<212> TYPE: PRT
<213> ORGANISM: Homo sapiens

<400> SEQUENCE: 115

Arg Asp Ser Ser
1

<210> SEQ ID NO 116
<211> LENGTH: 4
<212> TYPE: PRT
<213> ORGANISM: Homo sapiens

<400> SEQUENCE: 116

Met Asp Ser Ser
1

<210> SEQ ID NO 117
<211> LENGTH: 5
<212> TYPE: PRT
<213> ORGANISM: Homo sapiens

<400> SEQUENCE: 117

Met Arg Asp Ser Ser
1               5

<210> SEQ ID NO 118
<211> LENGTH: 5
<212> TYPE: PRT
<213> ORGANISM: Homo sapiens

<400> SEQUENCE: 118

Met Ser Ser Pro Leu
1               5

<210> SEQ ID NO 119
<211> LENGTH: 6
<212> TYPE: PRT
<213> ORGANISM: Homo sapiens

<400> SEQUENCE: 119

Met Asp Ser Ser Pro Leu
1               5

<210> SEQ ID NO 120
<211> LENGTH: 7
<212> TYPE: PRT
<213> ORGANISM: Homo sapiens

<400> SEQUENCE: 120

Met Ser Asp Ser Ser Pro Leu
1               5

<210> SEQ ID NO 121
<211> LENGTH: 5
```

```
<212> TYPE: PRT
<213> ORGANISM: Homo sapiens

<400> SEQUENCE: 121

Asp Ser Ser Pro Leu
1               5

<210> SEQ ID NO 122
<211> LENGTH: 5
<212> TYPE: PRT
<213> ORGANISM: Homo sapiens

<400> SEQUENCE: 122

Asp Ala Ser Pro His
1               5

<210> SEQ ID NO 123
<211> LENGTH: 4
<212> TYPE: PRT
<213> ORGANISM: Homo sapiens

<400> SEQUENCE: 123

Arg Asp Ser Ser
1

<210> SEQ ID NO 124
<211> LENGTH: 4
<212> TYPE: PRT
<213> ORGANISM: Homo sapiens

<400> SEQUENCE: 124

Met Asp Ser Ser
1

<210> SEQ ID NO 125
<211> LENGTH: 5
<212> TYPE: PRT
<213> ORGANISM: Homo sapiens

<400> SEQUENCE: 125

Met Arg Asp Ser Ser
1               5

<210> SEQ ID NO 126
<211> LENGTH: 6
<212> TYPE: PRT
<213> ORGANISM: Homo sapiens

<400> SEQUENCE: 126

Met Asp Ser Ser Pro Leu
1               5

<210> SEQ ID NO 127
<211> LENGTH: 7
<212> TYPE: PRT
<213> ORGANISM: Homo sapiens

<400> SEQUENCE: 127

Met Ser Asp Ser Ser Pro Leu
1               5

<210> SEQ ID NO 128
<211> LENGTH: 5
<212> TYPE: PRT
<213> ORGANISM: Homo sapiens
```

```
<400> SEQUENCE: 128

Met Ser Ser Pro Leu
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 129

Gly Ser Gly Gly Ser
1               5

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Linker
      sequence

<400> SEQUENCE: 130

Gly Gly Gly Ser
1

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Linker
      sequence

<400> SEQUENCE: 131

Gly Gly Ser Gly
1

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 132

Gly Gly Ser Gly Gly
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 133

Gly Ser Gly Ser Gly
1               5

<210> SEQ ID NO 134
<211> LENGTH: 5
```

-continued

```
<212> TYPE: PRT
<213> ORGANISM: Artificial Sequence
<220> FEATURE:
<223> OTHER INFORMATION: Description of Artificial Sequence: Linker
      sequence

<400> SEQUENCE: 134

Gly Ser Gly Gly Gly
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Linker
      sequence

<400> SEQUENCE: 135

Gly Ser Ser Ser Gly
1               5

<210> SEQ ID NO 136
<211> LENGTH: 32
<212> TYPE: DNA
<213> ORGANISM: Artificial Sequence
<220> FEATURE:
<223> OTHER INFORMATION: Description of Artificial Sequence: Forward
      primer

<400> SEQUENCE: 136
ccgactagtc accatgcgga gcgggtgtgt gg                                   32

<210> SEQ ID NO 137
<211> LENGTH: 41
<212> TYPE: DNA
<213> ORGANISM: Artificial Sequence
<220> FEATURE:
<223> OTHER INFORMATION: Description of Artificial Sequence: Reverse
      primer

<400> SEQUENCE: 137
ataagaatgc ggccgcttac ttctcaaagc tgggactcct c                         41

<210> SEQ ID NO 138
<211> LENGTH: 186
<212> TYPE: PRT
<213> ORGANISM: Homo sapiens

<400> SEQUENCE: 138

Asp Ser Ser Pro Leu Leu Gln Phe Gly Gly Gln Val Arg Leu Arg His
1               5                   10                  15

Leu Tyr Thr Ser Gly Pro His Gly Leu Ser Ser Cys Phe Leu Arg Ile
                20                  25                  30

Arg Ala Asp Gly Val Val Asp Cys Ala Arg Gly Gln Ser Ala His Ser
            35                  40                  45

Leu Leu Glu Ile Lys Ala Val Ala Leu Arg Thr Val Ala Ile Lys Gly
        50                  55                  60

Val His Ser Val Arg Tyr Leu Cys Met Gly Ala Asp Gly Lys Met Gln
65                  70                  75                  80

Gly Leu Leu Gln Tyr Ser Glu Glu Asp Cys Ala Phe Glu Glu Glu Ile
                85                  90                  95

Arg Pro Asp Gly Tyr Asn Val Tyr Arg Ser Glu Lys His Arg Leu Pro
                100                 105                 110
```

Val Ser Leu Ser Ser Ala Lys Gln Arg Gln Leu Tyr Lys Asn Arg Gly
            115                 120                 125

Phe Leu Pro Leu Ser His Phe Leu Pro Met Leu Pro Met Val Pro Glu
130                 135                 140

Glu Pro Glu Asp Leu Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 139
<211> LENGTH: 194
<212> TYPE: PRT
<213> ORGANISM: Homo sapiens

<400> SEQUENCE: 139

Arg Pro Leu Ala Phe Ser Asp Ala Ser Pro His Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 140
<211> LENGTH: 194
<212> TYPE: PRT
<213> ORGANISM: Homo sapiens

<400> SEQUENCE: 140

Arg Pro Leu Ala Phe Ser Asp Ser Ser Pro Leu Val His Tyr Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

```
Ala Arg Gly Gln Ser Ala His Ser Leu Leu Glu Ile Lys Ala Val Ala
     50                  55                  60

Leu Arg Thr Val Ala Ile Lys Gly Val His Ser Val Arg Tyr Leu Cys
 65                  70                  75                  80

Met Gly Ala Asp Gly Lys Met Gln Gly Leu Leu Gln Tyr Ser Glu Glu
                 85                  90                  95

Asp Cys Ala Phe Glu Glu Ile Arg Pro Asp Gly Tyr Asn Val Tyr
             100                 105                 110

Arg Ser Glu Lys His Arg Leu Pro Val Ser Leu Ser Ser Ala Lys Gln
             115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 141
<211> LENGTH: 188
<212> TYPE: PRT
<213> ORGANISM: Homo sapiens

<400> SEQUENCE: 141

Asp Ser Ser Pro Leu Val His Tyr Gly Trp Gly Asp Pro Ile Arg Leu
 1               5                  10                  15

Arg His Leu Tyr Thr Ser Gly Pro His Gly Leu Ser Ser Cys Phe Leu
                20                  25                  30

Arg Ile Arg Ala Asp Gly Val Val Asp Cys Ala Arg Gly Gln Ser Ala
             35                  40                  45

His Ser Leu Leu Glu Ile Lys Ala Val Ala Leu Arg Thr Val Ala Ile
 50                  55                  60

Lys Gly Val His Ser Val Arg Tyr Leu Cys Met Gly Ala Asp Gly Lys
 65                  70                  75                  80

Met Gln Gly Leu Leu Gln Tyr Ser Glu Glu Asp Cys Ala Phe Glu Glu
                 85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
            115                 120                 125

Arg Gly Phe Leu Pro Leu Ser His Phe Leu Pro Met Leu Pro Met Val
    130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185

<210> SEQ ID NO 142
<211> LENGTH: 193
<212> TYPE: PRT
<213> ORGANISM: Homo sapiens
```

-continued

```
<400> SEQUENCE: 142

Arg His Pro Ile Pro Asp Ser Ser Pro Leu Leu Gln Phe Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
            180                 185                 190

Lys

<210> SEQ ID NO 143
<211> LENGTH: 191
<212> TYPE: PRT
<213> ORGANISM: Homo sapiens

<400> SEQUENCE: 143

Arg His Pro Ile Pro Asp Ser Ser Pro Leu Leu Gln Trp Gly Asp Pro
1               5                   10                  15

Ile Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
```

```
                        165                 170                 175

Leu Val Thr Gly Leu Glu Ala Val Arg Ser Pro Ser Phe Glu Lys
            180                 185                 190

<210> SEQ ID NO 144
<211> LENGTH: 194
<212> TYPE: PRT
<213> ORGANISM: Homo sapiens

<400> SEQUENCE: 144

Arg Pro Leu Ala Phe Ser Asp Ala Gly Pro Leu Leu Gln Phe Gly Trp
1               5                   10                  15

Gly Asp Pro Ile Arg Leu Arg His Leu Tyr Thr Ser Gly Pro His Gly
            20                  25                  30

Leu Ser Ser Cys Phe Leu Arg Ile Arg Ala Asp Gly Val Val Asp Cys
        35                  40                  45

Ala Arg Gly Gln Ser Ala His Ser Leu Leu Glu Ile Lys Ala Val Ala
    50                  55                  60

Leu Arg Thr Val Ala Ile Lys Gly Val His Ser Val Arg Tyr Leu Cys
65                  70                  75                  80

Met Gly Ala Asp Gly Lys Met Gln Gly Leu Leu Gln Tyr Ser Glu Glu
                85                  90                  95

Asp Cys Ala Phe Glu Glu Glu Ile Arg Pro Asp Gly Tyr Asn Val Tyr
            100                 105                 110

Arg Ser Glu Lys His Arg Leu Pro Val Ser Leu Ser Ser Ala Lys Gln
        115                 120                 125

Arg Gln Leu Tyr Lys Asn Arg Gly Phe Leu Pro Leu Ser His Phe Leu
    130                 135                 140

Pro Met Leu Pro Met Val Pro Glu Glu Pro Glu Asp Leu Arg Gly His
145                 150                 155                 160

Leu Glu Ser Asp Met Phe Ser Ser Pro Leu Glu Thr Asp Ser Met Asp
                165                 170                 175

Pro Phe Gly Leu Val Thr Gly Leu Glu Ala Val Arg Ser Pro Ser Phe
            180                 185                 190

Glu Lys

<210> SEQ ID NO 145
<211> LENGTH: 193
<212> TYPE: PRT
<213> ORGANISM: Homo sapiens

<400> SEQUENCE: 145

Arg His Pro Ile Pro Asp Ser Ser Pro His Val His Tyr Gly Trp Gly
1               5                   10                  15

Asp Pro Ile Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110
```

```
Ser Glu Lys His Arg Leu Pro Val Ser Leu Ser Ser Ala Lys Gln Arg
            115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu
                180                 185                 190

Lys

<210> SEQ ID NO 146
<211> LENGTH: 192
<212> TYPE: PRT
<213> ORGANISM: Homo sapiens

<400> SEQUENCE: 146

Arg Pro Leu Ala Phe Ser Asp Ala Gly Pro Leu Leu Gln Phe Gly Gly
1               5                   10                  15

Gln Val Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
                100                 105                 110

Glu Lys His Arg Leu Pro Val Ser Leu Ser Ser Ala Lys Gln Arg Gln
            115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
                180                 185                 190

<210> SEQ ID NO 147
<211> LENGTH: 191
<212> TYPE: PRT
<213> ORGANISM: Homo sapiens

<400> SEQUENCE: 147

Arg His Pro Ile Pro Asp Ser Ser Pro His Val His Tyr Gly Gly Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45
```

-continued

```
Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190
```

<210> SEQ ID NO 148
<211> LENGTH: 187
<212> TYPE: PRT
<213> ORGANISM: Homo sapiens

<400> SEQUENCE: 148

```
Arg Asp Ser Ser Pro Leu Leu Gln Phe Gly Gly Gln Val Arg Leu Arg
  1               5                  10                  15

His Leu Tyr Thr Ser Gly Pro His Gly Leu Ser Ser Cys Phe Leu Arg
                 20                  25                  30

Ile Arg Ala Asp Gly Val Val Asp Cys Ala Arg Gly Gln Ser Ala His
             35                  40                  45

Ser Leu Leu Glu Ile Lys Ala Val Ala Leu Arg Thr Val Ala Ile Lys
 50                  55                  60

Gly Val His Ser Val Arg Tyr Leu Cys Met Gly Ala Asp Gly Lys Met
 65                  70                  75                  80

Gln Gly Leu Leu Gln Tyr Ser Glu Glu Asp Cys Ala Phe Glu Glu Glu
                 85                  90                  95

Ile Arg Pro Asp Gly Tyr Asn Val Tyr Arg Ser Glu Lys His Arg Leu
            100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
                180                 185
```

<210> SEQ ID NO 149
<211> LENGTH: 192
<212> TYPE: PRT
<213> ORGANISM: Homo sapiens

<400> SEQUENCE: 149

```
Arg Pro Leu Ala Phe Ser Asp Ser Ser Pro Leu Leu Gln Phe Gly Gly
 1               5                  10                  15
Gln Val Arg Leu Arg His Leu Tyr Thr Ser Gly Pro His Gly Leu Ser
             20                  25                  30
Ser Cys Phe Leu Arg Ile Arg Ala Asp Gly Val Val Asp Cys Ala Arg
         35                  40                  45
Gly Gln Ser Ala His Ser Leu Leu Glu Ile Lys Ala Val Ala Leu Arg
 50                  55                  60
Thr Val Ala Ile Lys Gly Val His Ser Val Arg Tyr Leu Cys Met Gly
 65                  70                  75                  80
Ala Asp Gly Lys Met Gln Gly Leu Leu Gln Tyr Ser Glu Glu Asp Cys
                 85                  90                  95
Ala Phe Glu Glu Glu Ile Arg Pro Asp Gly Tyr Asn Val Tyr Arg Ser
             100                 105                 110
Glu Lys His Arg Leu Pro Val Ser Leu Ser Ser Ala Lys Gln Arg Gln
             115                 120                 125
Leu Tyr Lys Asn Arg Gly Phe Leu Pro Leu Ser His Phe Leu Pro Met
 130                 135                 140
Leu Pro Met Val Pro Glu Glu Pro Glu Asp Leu Arg Gly His Leu Glu
145                 150                 155                 160
Ser Asp Met Phe Ser Ser Pro Leu Glu Thr Asp Ser Met Asp Pro Phe
                 165                 170                 175
Gly Leu Val Thr Gly Leu Glu Ala Val Arg Ser Pro Ser Phe Glu Lys
             180                 185                 190
```

<210> SEQ ID NO 150
<211> LENGTH: 191
<212> TYPE: PRT
<213> ORGANISM: Homo sapiens

<400> SEQUENCE: 150

```
Arg His Pro Ile Pro Asp Ser Ser Pro Leu Leu Gln Phe Gly Ala Gln
 1               5                  10                  15
Val Arg Leu Arg His Leu Tyr Thr Ser Gly Pro His Gly Leu Ser Ser
             20                  25                  30
Cys Phe Leu Arg Ile Arg Ala Asp Gly Val Val Asp Cys Ala Arg Gly
         35                  40                  45
Gln Ser Ala His Ser Leu Leu Glu Ile Lys Ala Val Ala Leu Arg Thr
 50                  55                  60
Val Ala Ile Lys Gly Val His Ser Val Arg Tyr Leu Cys Met Gly Ala
 65                  70                  75                  80
Asp Gly Lys Met Gln Gly Leu Leu Gln Tyr Ser Glu Glu Asp Cys Ala
                 85                  90                  95
Phe Glu Glu Glu Ile Arg Pro Asp Gly Tyr Asn Val Tyr Arg Ser Glu
             100                 105                 110
Lys His Arg Leu Pro Val Ser Leu Ser Ser Ala Lys Gln Arg Gln Leu
             115                 120                 125
Tyr Lys Asn Arg Gly Phe Leu Pro Leu Ser His Phe Leu Pro Met Leu
 130                 135                 140
Pro Met Val Pro Glu Glu Pro Glu Asp Leu Arg Gly His Leu Glu Ser
145                 150                 155                 160
Asp Met Phe Ser Ser Pro Leu Glu Thr Asp Ser Met Asp Pro Phe Gly
                 165                 170                 175
Leu Val Thr Gly Leu Glu Ala Val Arg Ser Pro Ser Phe Glu Lys
             180                 185                 190
```

<210> SEQ ID NO 151
<211> LENGTH: 191
<212> TYPE: PRT
<213> ORGANISM: Homo sapiens

<400> SEQUENCE: 151

```
Arg His Pro Ile Pro Asp Ser Ser Pro Leu Leu Gln Phe Gly Asp Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190
```

<210> SEQ ID NO 152
<211> LENGTH: 191
<212> TYPE: PRT
<213> ORGANISM: Homo sapiens

<400> SEQUENCE: 152

```
Arg His Pro Ile Pro Asp Ser Ser Pro Leu Leu Gln Phe Gly Pro Gln
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140
```

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 153
<211> LENGTH: 191
<212> TYPE: PRT
<213> ORGANISM: Homo sapiens

<400> SEQUENCE: 153

Arg His Pro Ile Pro Asp Ser Ser Pro Leu Leu Gln Phe Gly Gly Ala
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 154
<211> LENGTH: 191
<212> TYPE: PRT
<213> ORGANISM: Homo sapiens

<400> SEQUENCE: 154

Arg His Pro Ile Pro Asp Ser Ser Pro Leu Leu Gln Phe Gly Gly Glu
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 155
<211> LENGTH: 191
<212> TYPE: PRT
<213> ORGANISM: Homo sapiens

<400> SEQUENCE: 155

Arg His Pro Ile Pro Asp Ser Ser Pro Leu Leu Gln Phe Gly Gly Asn
1               5                   10                  15

Val Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
            115                 120                 125

Tyr Lys Asn Arg Gly Phe Leu Pro Leu Ser His Phe Leu Pro Met Leu
        130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
                180                 185                 190

<210> SEQ ID NO 156
<211> LENGTH: 191
<212> TYPE: PRT
<213> ORGANISM: Homo sapiens

<400> SEQUENCE: 156

Arg His Pro Ile Pro Asp Ser Ser Pro Leu Leu Gln Phe Gly Gly Gln
1               5                   10                  15

Ala Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

```
Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 157
<211> LENGTH: 191
<212> TYPE: PRT
<213> ORGANISM: Homo sapiens

<400> SEQUENCE: 157

Arg His Pro Ile Pro Asp Ser Ser Pro Leu Leu Gln Phe Gly Gly Gln
  1               5                  10                  15

Ile Arg Leu Arg His Leu Tyr Thr Ser Gly Pro His Gly Leu Ser Ser
                 20                  25                  30

Cys Phe Leu Arg Ile Arg Ala Asp Gly Val Val Asp Cys Ala Arg Gly
                 35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
 65                  70                  75                  80

Asp Gly Lys Met Gln Gly Leu Leu Gln Tyr Ser Glu Glu Asp Cys Ala
                 85                  90                  95

Phe Glu Glu Glu Ile Arg Pro Asp Gly Tyr Asn Val Tyr Arg Ser Glu
                100                 105                 110

Lys His Arg Leu Pro Val Ser Leu Ser Ser Ala Lys Gln Arg Gln Leu
                115                 120                 125

Tyr Lys Asn Arg Gly Phe Leu Pro Leu Ser His Phe Leu Pro Met Leu
            130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 158
<211> LENGTH: 191
<212> TYPE: PRT
<213> ORGANISM: Homo sapiens

<400> SEQUENCE: 158
```

Arg His Pro Ile Pro Asp Ser Ser Pro Leu Leu Gln Phe Gly Gly Gln
1               5                   10                  15

Thr Arg Leu Arg His Leu Tyr Thr Ser Gly Pro His Gly Leu Ser Ser
            20                  25                  30

Cys Phe Leu Arg Ile Arg Ala Asp Gly Val Val Asp Cys Ala Arg Gly
        35                  40                  45

Gln Ser Ala His Ser Leu Leu Glu Ile Lys Ala Val Ala Leu Arg Thr
    50                  55                  60

Val Ala Ile Lys Gly Val His Ser Val Arg Tyr Leu Cys Met Gly Ala
65                  70                  75                  80

Asp Gly Lys Met Gln Gly Leu Leu Gln Tyr Ser Glu Glu Asp Cys Ala
                85                  90                  95

Phe Glu Glu Glu Ile Arg Pro Asp Gly Tyr Asn Val Tyr Arg Ser Glu
            100                 105                 110

Lys His Arg Leu Pro Val Ser Leu Ser Ser Ala Lys Gln Arg Gln Leu
        115                 120                 125

Tyr Lys Asn Arg Gly Phe Leu Pro Leu Ser His Phe Leu Pro Met Leu
    130                 135                 140

Pro Met Val Pro Glu Glu Pro Glu Asp Leu Arg Gly His Leu Glu Ser
145                 150                 155                 160

Asp Met Phe Ser Ser Pro Leu Glu Thr Asp Ser Met Asp Pro Phe Gly
                165                 170                 175

Leu Val Thr Gly Leu Glu Ala Val Arg Ser Pro Ser Phe Glu Lys
            180                 185                 190

<210> SEQ ID NO 159
<211> LENGTH: 193
<212> TYPE: PRT
<213> ORGANISM: Homo sapiens

<400> SEQUENCE: 159

Arg His Pro Ile Pro Asp Ser Ser Pro Leu Leu Gln Phe Gly Trp Gly
1               5                   10                  15

Gln Pro Val Arg Leu Arg His Leu Tyr Thr Ser Gly Pro His Gly Leu
            20                  25                  30

Ser Ser Cys Phe Leu Arg Ile Arg Ala Asp Gly Val Val Asp Cys Ala
        35                  40                  45

Arg Gly Gln Ser Ala His Ser Leu Leu Glu Ile Lys Ala Val Ala Leu
    50                  55                  60

Arg Thr Val Ala Ile Lys Gly Val His Ser Val Arg Tyr Leu Cys Met
65                  70                  75                  80

Gly Ala Asp Gly Lys Met Gln Gly Leu Leu Gln Tyr Ser Glu Glu Asp
                85                  90                  95

Cys Ala Phe Glu Glu Glu Ile Arg Pro Asp Gly Tyr Asn Val Tyr Arg
            100                 105                 110

Ser Glu Lys His Arg Leu Pro Val Ser Leu Ser Ser Ala Lys Gln Arg
        115                 120                 125

Gln Leu Tyr Lys Asn Arg Gly Phe Leu Pro Leu Ser His Phe Leu Pro
    130                 135                 140

Met Leu Pro Met Val Pro Glu Glu Pro Glu Asp Leu Arg Gly His Leu
145                 150                 155                 160

Glu Ser Asp Met Phe Ser Ser Pro Leu Glu Thr Asp Ser Met Asp Pro
                165                 170                 175

Phe Gly Leu Val Thr Gly Leu Glu Ala Val Arg Ser Pro Ser Phe Glu 180                 185                 190

Lys

<210> SEQ ID NO 160
<211> LENGTH: 190
<212> TYPE: PRT
<213> ORGANISM: Homo sapiens

<400> SEQUENCE: 160

His Pro Ile Pro Asp Ser Ser Pro Leu Leu Gln Phe Gly Gly Gln Val
1               5                   10                  15

Arg Leu Arg His Leu Tyr Thr Ser Gly Pro His Gly Leu Ser Ser Cys
            20                  25                  30

Phe Leu Arg Ile Arg Ala Asp Gly Val Val Asp Cys Ala Arg Gly Gln
        35                  40                  45

Ser Ala His Ser Leu Leu Glu Ile Lys Ala Val Ala Leu Arg Thr Val
    50                  55                  60

Ala Ile Lys Gly Val His Ser Val Arg Tyr Leu Cys Met Gly Ala Asp
65                  70                  75                  80

Gly Lys Met Gln Gly Leu Leu Gln Tyr Ser Glu Glu Asp Cys Ala Phe
                85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
        115                 120                 125

Lys Asn Arg Gly Phe Leu Pro Leu Ser His Phe Leu Pro Met Leu Pro
    130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 161
<211> LENGTH: 186
<212> TYPE: PRT
<213> ORGANISM: Homo sapiens

<400> SEQUENCE: 161

Asp Ser Ser Pro Leu Leu Gln Phe Gly Gly Gln Val Arg Leu Arg His
1               5                   10                  15

Leu Tyr Thr Ser Gly Pro His Gly Leu Ser Ser Cys Phe Leu Arg Ile
            20                  25                  30

Arg Ala Asp Gly Val Val Asp Cys Ala Arg Gly Gln Ser Ala His Ser
        35                  40                  45

Leu Leu Glu Ile Lys Ala Val Ala Leu Arg Thr Val Ala Ile Lys Gly
    50                  55                  60

Val His Ser Val Arg Tyr Leu Cys Met Gly Ala Asp Gly Lys Met Gln
65                  70                  75                  80

Gly Leu Leu Gln Tyr Ser Glu Glu Asp Cys Ala Phe Glu Glu Glu Ile
                85                  90                  95

Arg Pro Asp Gly Tyr Asn Val Tyr Arg Ser Glu Lys His Arg Leu Pro
            100                 105                 110

Val Ser Leu Ser Ser Ala Lys Gln Arg Gln Leu Tyr Lys Asn Arg Gly
        115                 120                 125

```
Phe Leu Pro Leu Ser His Phe Leu Pro Met Leu Pro Met Val Pro Glu
    130                 135                 140
Glu Pro Glu Asp Leu Arg Gly His Leu Glu Ser Asp Met Phe Ser Ser
145                 150                 155                 160
Pro Leu Glu Thr Asp Ser Met Asp Pro Phe Gly Leu Val Thr Gly Leu
                165                 170                 175
Glu Ala Val Arg Ser Pro Ser Phe Glu Lys
            180                 185
```

<210> SEQ ID NO 162
<211> LENGTH: 190
<212> TYPE: PRT
<213> ORGANISM: Homo sapiens

<400> SEQUENCE: 162

```
His Pro Ile Pro Asp Ser Ser Pro Leu Leu Gln Trp Gly Asp Pro Ile
1               5                   10                  15
Arg Leu Arg His Leu Tyr Thr Ser Gly Pro His Gly Leu Ser Ser Cys
            20                  25                  30
Phe Leu Arg Ile Arg Ala Asp Gly Val Val Asp Cys Ala Arg Gly Gln
        35                  40                  45
Ser Ala His Ser Leu Leu Glu Ile Lys Ala Val Ala Leu Arg Thr Val
    50                  55                  60
Ala Ile Lys Gly Val His Ser Val Arg Tyr Leu Cys Met Gly Ala Asp
65                  70                  75                  80
Gly Lys Met Gln Gly Leu Leu Gln Tyr Ser Glu Glu Asp Cys Ala Phe
                85                  90                  95
Glu Glu Glu Ile Arg Pro Asp Gly Tyr Asn Val Tyr Arg Ser Glu Lys
            100                 105                 110
His Arg Leu Pro Val Ser Leu Ser Ser Ala Lys Gln Arg Gln Leu Tyr
        115                 120                 125
Lys Asn Arg Gly Phe Leu Pro Leu Ser His Phe Leu Pro Met Leu Pro
    130                 135                 140
Met Val Pro Glu Glu Pro Glu Asp Leu Arg Gly His Leu Glu Ser Asp
145                 150                 155                 160
Met Phe Ser Ser Pro Leu Glu Thr Asp Ser Met Asp Pro Phe Gly Leu
                165                 170                 175
Val Thr Gly Leu Glu Ala Val Arg Ser Pro Ser Phe Glu Lys
            180                 185                 190
```

<210> SEQ ID NO 163
<211> LENGTH: 192
<212> TYPE: PRT
<213> ORGANISM: Homo sapiens

<400> SEQUENCE: 163

```
His Pro Ile Pro Asp Ser Ser Pro Leu Leu Gln Phe Gly Trp Gly Asp
1               5                   10                  15
Pro Ile Arg Leu Arg His Leu Tyr Thr Ser Gly Pro His Gly Leu Ser
            20                  25                  30
Ser Cys Phe Leu Arg Ile Arg Ala Asp Gly Val Val Asp Cys Ala Arg
        35                  40                  45
Gly Gln Ser Ala His Ser Leu Leu Glu Ile Lys Ala Val Ala Leu Arg
    50                  55                  60
Thr Val Ala Ile Lys Gly Val His Ser Val Arg Tyr Leu Cys Met Gly
65                  70                  75                  80
```

```
Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 164
<211> LENGTH: 192
<212> TYPE: PRT
<213> ORGANISM: Homo sapiens

<400> SEQUENCE: 164

His Pro Ile Pro Asp Ser Ser Pro His Val His Tyr Gly Trp Gly Asp
1               5                   10                  15

Pro Ile Arg Leu Arg His Leu Tyr Thr Ser Gly Pro His Gly Leu Ser
            20                  25                  30

Ser Cys Phe Leu Arg Ile Arg Ala Asp Gly Val Val Asp Cys Ala Arg
        35                  40                  45

Gly Gln Ser Ala His Ser Leu Leu Glu Ile Lys Ala Val Ala Leu Arg
    50                  55                  60

Thr Val Ala Ile Lys Gly Val His Ser Val Arg Tyr Leu Cys Met Gly
65                  70                  75                  80

Ala Asp Gly Lys Met Gln Gly Leu Leu Gln Tyr Ser Glu Glu Asp Cys
                85                  90                  95

Ala Phe Glu Glu Glu Ile Arg Pro Asp Gly Tyr Asn Val Tyr Arg Ser
            100                 105                 110

Glu Lys His Arg Leu Pro Val Ser Leu Ser Ser Ala Lys Gln Arg Gln
        115                 120                 125

Leu Tyr Lys Asn Arg Gly Phe Leu Pro Leu Ser His Phe Leu Pro Met
    130                 135                 140

Leu Pro Met Val Pro Glu Glu Pro Glu Asp Leu Arg Gly His Leu Glu
145                 150                 155                 160

Ser Asp Met Phe Ser Ser Pro Leu Glu Thr Asp Ser Met Asp Pro Phe
                165                 170                 175

Gly Leu Val Thr Gly Leu Glu Ala Val Arg Ser Pro Ser Phe Glu Lys
            180                 185                 190

<210> SEQ ID NO 165
<211> LENGTH: 190
<212> TYPE: PRT
<213> ORGANISM: Homo sapiens

<400> SEQUENCE: 165

His Pro Ile Pro Asp Ser Ser Pro His Val His Tyr Gly Gly Gln Val
1               5                   10                  15

Arg Leu Arg His Leu Tyr Thr Ser Gly Pro His Gly Leu Ser Ser Cys
            20                  25                  30
```

```
Phe Leu Arg Ile Arg Ala Asp Gly Val Val Asp Cys Ala Arg Gly Gln
            35                  40                  45

Ser Ala His Ser Leu Leu Glu Ile Lys Ala Val Ala Leu Arg Thr Val
 50                  55                  60

Ala Ile Lys Gly Val His Ser Val Arg Tyr Leu Cys Met Gly Ala Asp
 65                  70                  75                  80

Gly Lys Met Gln Gly Leu Leu Gln Tyr Ser Glu Glu Asp Cys Ala Phe
                 85                  90                  95

Glu Glu Glu Ile Arg Pro Asp Gly Tyr Asn Val Tyr Arg Ser Glu Lys
            100                 105                 110

His Arg Leu Pro Val Ser Leu Ser Ser Ala Lys Gln Arg Gln Leu Tyr
            115                 120                 125

Lys Asn Arg Gly Phe Leu Pro Leu Ser His Phe Leu Pro Met Leu Pro
130                 135                 140

Met Val Pro Glu Glu Pro Glu Asp Leu Arg Gly His Leu Glu Ser Asp
145                 150                 155                 160

Met Phe Ser Ser Pro Leu Glu Thr Asp Ser Met Asp Pro Phe Gly Leu
                165                 170                 175

Val Thr Gly Leu Glu Ala Val Arg Ser Pro Ser Phe Glu Lys
            180                 185                 190

<210> SEQ ID NO 166
<211> LENGTH: 188
<212> TYPE: PRT
<213> ORGANISM: Homo sapiens

<400> SEQUENCE: 166

Asp Ala Gly Pro His Val His Tyr Gly Trp Gly Asp Pro Ile Arg Leu
1               5                   10                  15

Arg His Leu Tyr Thr Ser Gly Pro His Gly Leu Ser Ser Cys Phe Leu
            20                  25                  30

Arg Ile Arg Ala Asp Gly Val Val Asp Cys Ala Arg Gly Gln Ser Ala
        35                  40                  45

His Ser Leu Leu Glu Ile Lys Ala Val Ala Leu Arg Thr Val Ala Ile
 50                  55                  60

Lys Gly Val His Ser Val Arg Tyr Leu Cys Met Gly Ala Asp Gly Lys
 65                  70                  75                  80

Met Gln Gly Leu Leu Gln Tyr Ser Glu Glu Asp Cys Ala Phe Glu Glu
                 85                  90                  95

Glu Ile Arg Pro Asp Gly Tyr Asn Val Tyr Arg Ser Glu Lys His Arg
            100                 105                 110

Leu Pro Val Ser Leu Ser Ser Ala Lys Gln Arg Gln Leu Tyr Lys Asn
            115                 120                 125

Arg Gly Phe Leu Pro Leu Ser His Phe Leu Pro Met Leu Pro Met Val
130                 135                 140

Pro Glu Glu Pro Glu Asp Leu Arg Gly His Leu Glu Ser Asp Met Phe
145                 150                 155                 160

Ser Ser Pro Leu Glu Thr Asp Ser Met Asp Pro Phe Gly Leu Val Thr
                165                 170                 175

Gly Leu Glu Ala Val Arg Ser Pro Ser Phe Glu Lys
            180                 185

<210> SEQ ID NO 167
<211> LENGTH: 183
<212> TYPE: PRT
```

<213> ORGANISM: Homo sapiens

<400> SEQUENCE: 167

Val His Tyr Gly Trp Gly Asp Pro Ile Arg Leu Arg His Leu Tyr Thr
1               5                   10                  15

Ser Gly Pro His Gly Leu Ser Ser Cys Phe Leu Arg Ile Arg Ala Asp
            20                  25                  30

Gly Val Val Asp Cys Ala Arg Gly Gln Ser Ala His Ser Leu Leu Glu
        35                  40                  45

Ile Lys Ala Val Ala Leu Arg Thr Val Ala Ile Lys Gly Val His Ser
    50                  55                  60

Val Arg Tyr Leu Cys Met Gly Ala Asp Gly Lys Met Gln Gly Leu Leu
65                  70                  75                  80

Gln Tyr Ser Glu Glu Asp Cys Ala Phe Glu Glu Glu Ile Arg Pro Asp
                85                  90                  95

Gly Tyr Asn Val Tyr Arg Ser Glu Lys His Arg Leu Pro Val Ser Leu
            100                 105                 110

Ser Ser Ala Lys Gln Arg Gln Leu Tyr Lys Asn Arg Gly Phe Leu Pro
        115                 120                 125

Leu Ser His Phe Leu Pro Met Leu Pro Met Val Pro Glu Glu Pro Glu
    130                 135                 140

Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
            180

<210> SEQ ID NO 168
<211> LENGTH: 174
<212> TYPE: PRT
<213> ORGANISM: Homo sapiens

<400> SEQUENCE: 168

Arg Leu Arg His Leu Tyr Thr Ser Gly Pro His Gly Leu Ser Ser Cys
1               5                   10                  15

Phe Leu Arg Ile Arg Ala Asp Gly Val Val Asp Cys Ala Arg Gly Gln
            20                  25                  30

Ser Ala His Ser Leu Leu Glu Ile Lys Ala Val Ala Leu Arg Thr Val
        35                  40                  45

Ala Ile Lys Gly Val His Ser Val Arg Tyr Leu Cys Met Gly Ala Asp
    50                  55                  60

Gly Lys Met Gln Gly Leu Leu Gln Tyr Ser Glu Glu Asp Cys Ala Phe
65                  70                  75                  80

Glu Glu Glu Ile Arg Pro Asp Gly Tyr Asn Val Tyr Arg Ser Glu Lys
                85                  90                  95

His Arg Leu Pro Val Ser Leu Ser Ser Ala Lys Gln Arg Gln Leu Tyr
            100                 105                 110

Lys Asn Arg Gly Phe Leu Pro Leu Ser His Phe Leu Pro Met Leu Pro
        115                 120                 125

Met Val Pro Glu Glu Pro Glu Asp Leu Arg Gly His Leu Glu Ser Asp
    130                 135                 140

Met Phe Ser Ser Pro Leu Glu Thr Asp Ser Met Asp Pro Phe Gly Leu
145                 150                 155                 160

Val Thr Gly Leu Glu Ala Val Arg Ser Pro Ser Phe Glu Lys

```
                 165                 170

<210> SEQ ID NO 169
<211> LENGTH: 14
<212> TYPE: PRT
<213> ORGANISM: Artificial Sequence
<220> FEATURE:
<223> OTHER INFORMATION: Synthetic peptide

<400> SEQUENCE: 169

Trp Gly Asp Pro Ile Arg Leu Arg His Leu Tyr Thr Ser Gly
1               5                   10

<210> SEQ ID NO 170
<211> LENGTH: 5
<212> TYPE: PRT
<213> ORGANISM: Artificial Sequence
<220> FEATURE:
<223> OTHER INFORMATION: Synthetic peptide

<400> SEQUENCE: 170

Trp Gly Asp Pro Ile
1               5

<210> SEQ ID NO 171
<211> LENGTH: 4
<212> TYPE: PRT
<213> ORGANISM: Artificial Sequence
<220> FEATURE:
<223> OTHER INFORMATION: Synthetic peptide

<400> SEQUENCE: 171

Trp Gly Pro Ile
1

<210> SEQ ID NO 172
<211> LENGTH: 5
<212> TYPE: PRT
<213> ORGANISM: Artificial Sequence
<220> FEATURE:
<223> OTHER INFORMATION: Synthetic peptide

<400> SEQUENCE: 172

Trp Gly Asp Pro Val
1               5

<210> SEQ ID NO 173
<211> LENGTH: 4
<212> TYPE: PRT
<213> ORGANISM: Artificial Sequence
<220> FEATURE:
<223> OTHER INFORMATION: Synthetic peptide

<400> SEQUENCE: 173

Trp Gly Asp Ile
1

<210> SEQ ID NO 174
<211> LENGTH: 4
<212> TYPE: PRT
<213> ORGANISM: Artificial Sequence
<220> FEATURE:
<223> OTHER INFORMATION: Synthetic peptide

<400> SEQUENCE: 174

Gly Asp Pro Ile
1
```

<210> SEQ ID NO 175
<211> LENGTH: 5
<212> TYPE: PRT
<213> ORGANISM: Artificial Sequence
<220> FEATURE:
<223> OTHER INFORMATION: Synthetic peptide

<400> SEQUENCE: 175

Trp Gly Gln Pro Ile
1               5

<210> SEQ ID NO 176
<211> LENGTH: 5
<212> TYPE: PRT
<213> ORGANISM: Artificial Sequence
<220> FEATURE:
<223> OTHER INFORMATION: Synthetic peptide

<400> SEQUENCE: 176

Trp Gly Ala Pro Ile
1               5

<210> SEQ ID NO 177
<211> LENGTH: 5
<212> TYPE: PRT
<213> ORGANISM: Artificial Sequence
<220> FEATURE:
<223> OTHER INFORMATION: Synthetic peptide

<400> SEQUENCE: 177

Ala Gly Asp Pro Ile
1               5

<210> SEQ ID NO 178
<211> LENGTH: 5
<212> TYPE: PRT
<213> ORGANISM: Artificial Sequence
<220> FEATURE:
<223> OTHER INFORMATION: Synthetic peptide

<400> SEQUENCE: 178

Trp Ala Asp Pro Ile
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic peptide

<400> SEQUENCE: 179

Trp Gly Asp Ala Ile
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic peptide

<400> SEQUENCE: 180

Trp Gly Asp Pro Ala
1               5

<210> SEQ ID NO 181
<211> LENGTH: 4
<212> TYPE: PRT
<213> ORGANISM: Artificial Sequence
<220> FEATURE:
<223> OTHER INFORMATION: Synthetic peptide

<400> SEQUENCE: 181

Trp Asp Pro Ile
1

<210> SEQ ID NO 182
<211> LENGTH: 4
<212> TYPE: PRT
<213> ORGANISM: Artificial Sequence
<220> FEATURE:
<223> OTHER INFORMATION: Synthetic peptide

<400> SEQUENCE: 182

Trp Gly Asp Ile
1

<210> SEQ ID NO 183
<211> LENGTH: 4
<212> TYPE: PRT
<213> ORGANISM: Artificial Sequence
<220> FEATURE:
<223> OTHER INFORMATION: Synthetic peptide

<400> SEQUENCE: 183

Trp Gly Asp Pro
1

<210> SEQ ID NO 184
<211> LENGTH: 5
<212> TYPE: PRT
<213> ORGANISM: Artificial Sequence
<220> FEATURE:
<223> OTHER INFORMATION: Synthetic peptide

<400> SEQUENCE: 184

Phe Gly Asp Pro Ile
1               5

<210> SEQ ID NO 185
<211> LENGTH: 9
<212> TYPE: PRT
<213> ORGANISM: Artificial Sequence
<220> FEATURE:
<223> OTHER INFORMATION: Synthetic peptide

<400> SEQUENCE: 185

Arg Leu Arg His Leu Tyr Thr Ser Gly
1               5

<210> SEQ ID NO 186
<211> LENGTH: 9
<212> TYPE: PRT
<213> ORGANISM: Artificial Sequence
<220> FEATURE:
<223> OTHER INFORMATION: core sequence

<400> SEQUENCE: 186

Arg Gln Arg Tyr Leu Tyr Thr Asp Asp
1               5

<210> SEQ ID NO 187
<211> LENGTH: 13
<212> TYPE: PRT
<213> ORGANISM: Artificial Sequence
<220> FEATURE:
<223> OTHER INFORMATION: Synthetic peptide

<400> SEQUENCE: 187

Ala Gly Pro His Val His Tyr Gly Trp Gly Asp Pro Ile
1               5                   10

<210> SEQ ID NO 188
<211> LENGTH: 165
<212> TYPE: PRT
<213> ORGANISM: Homo sapiens
<220> FEATURE:
<223> OTHER INFORMATION: FGF19 C-terminal sequence

<400> SEQUENCE: 188

Pro His Gly Leu Ser Ser Cys Phe Leu Arg Ile Arg Ala Asp Gly Val
1               5                   10                  15

Val Asp Cys Ala Arg Gly Gln Ser Ala His Ser Leu Leu Glu Ile Lys
            20                  25                  30

Ala Val Ala Leu Arg Thr Val Ala Ile Lys Gly Val His Ser Val Arg
        35                  40                  45

Tyr Leu Cys Met Gly Ala Asp Gly Lys Met Gln Gly Leu Leu Gln Tyr
    50                  55                  60

Ser Glu Glu Asp Cys Ala Phe Glu Glu Ile Arg Pro Asp Gly Tyr
65                  70                  75                  80

Asn Val Tyr Arg Ser Glu Lys His Arg Leu Pro Val Ser Leu Ser Ser
                85                  90                  95

Ala Lys Gln Arg Gln Leu Tyr Lys Asn Arg Gly Phe Leu Pro Leu Ser
            100                 105                 110

His Phe Leu Pro Met Leu Pro Met Val Pro Glu Glu Pro Glu Asp Leu
        115                 120                 125

Arg Gly His Leu Glu Ser Asp Met Phe Ser Ser Pro Leu Glu Thr Asp
    130                 135                 140

Ser Met Asp Pro Phe Gly Leu Val Thr Gly Leu Glu Ala Val Arg Ser
145                 150                 155                 160

Pro Ser Phe Glu Lys
                165

<210> SEQ ID NO 189
<211> LENGTH: 5
<212> TYPE: PRT
<213> ORGANISM: Artificial Sequence
<220> FEATURE:
<223> OTHER INFORMATION: Linker sequence

<400> SEQUENCE: 189

Gly Gly Gly Ser Gly
1               5

<210> SEQ ID NO 190
<211> LENGTH: 11
<212> TYPE: PRT
<213> ORGANISM: Homo sapiens
<220> FEATURE:
<223> OTHER INFORMATION: Sheet-8/Loop-8/Sheet-9 region of FGF19

```
<400> SEQUENCE: 190

Glu Glu Ile Arg Pro Asp Gly Tyr Asn Val Tyr
1               5                   10

<210> SEQ ID NO 191
<211> LENGTH: 11
<212> TYPE: PRT
<213> ORGANISM: Homo sapiens
<220> FEATURE:
<223> OTHER INFORMATION: Sheet-8/Loop-8/Sheet-9 region of FGF21

<400> SEQUENCE: 191

Glu Leu Leu Leu Glu Asp Gly Tyr Asn Val Tyr
1               5                   10

<210> SEQ ID NO 192
<211> LENGTH: 187
<212> TYPE: PRT
<213> ORGANISM: Artificial Sequence
<220> FEATURE:
<223> OTHER INFORMATION: M53 sequence

<400> SEQUENCE: 192

Met Asp Ser Ser Pro Leu Leu Gln Trp Gly Pro Ile Arg Leu Arg
1               5                   10                  15

His Leu Tyr Thr Ser Gly Pro His Gly Leu Ser Ser Cys Phe Leu Arg
                20                  25                  30

Ile Arg Ala Asp Gly Val Val Asp Cys Ala Arg Gly Gln Ser Ala His
                35                  40                  45

Ser Leu Leu Glu Ile Lys Ala Val Ala Leu Arg Thr Val Ala Ile Lys
        50                  55                  60

Gly Val His Ser Val Arg Tyr Leu Cys Met Gly Ala Asp Gly Lys Met
65                  70                  75                  80

Gln Gly Leu Leu Gln Tyr Ser Glu Glu Asp Cys Ala Phe Glu Glu Glu
                85                  90                  95

Ile Arg Pro Asp Gly Tyr Asn Val Tyr Arg Ser Glu Lys His Arg Leu
                100                 105                 110

Pro Val Ser Leu Ser Ser Ala Lys Gln Arg Gln Leu Tyr Lys Asn Arg
        115                 120                 125

Gly Phe Leu Pro Leu Ser His Phe Leu Pro Met Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
                180                 185
```

METHODS OF USING COMPOSITIONS COMPRISING FUSION VARIANTS OF FGF19 POLYPEPTIDES FOR REDUCING GLUCOSE LEVELS IN A SUBJECT

RELATED APPLICATIONS

This application is a division of U.S. Ser. No. 14/743,851, filed Jun. 18, 2015, which is a division of U.S. Ser. No. 14/616,401, filed Feb. 6, 2015 (now U.S. Pat. No. 9,089,525), which is a division of U.S. Ser. No. 13/538,705 filed Jun. 29, 2012 (now U.S. Pat. No. 8,951,966), which claims the benefit of priority of U.S. Ser. No. 61/504,128 filed Jul. 1, 2011, and U.S. Ser. No. 61/515,126 filed Aug. 4, 2011, each of which are expressly incorporated herein by reference in their entirety.

FIELD OF THE INVENTION

The invention relates to variants of fibroblast growth factor 19 (FGF19) proteins and peptide sequences (and peptidomimetics) and fusions of fibroblast growth factor 19 (FGF19) and/or fibroblast growth factor 21 (FGF21) proteins and peptide sequences (and peptidomimetics), and variants of fusions of fibroblast growth factor 19 (FGF19) and/or fibroblast growth factor 21 (FGF21) proteins and peptide sequences (and peptidomimetics) having glucose lowering activity, and methods for and uses in treatment of hyperglycemia and other disorders.

INTRODUCTION

Diabetes mellitus is a debilitating metabolic disease caused by absent insulin production (type 1) or insulin resistance or insufficient insulin production (type 2) from pancreatic β-cells. β-cells are specialized endocrine cells that manufacture and store insulin for release following a meal. Insulin is a hormone that facilitates the transfer of glucose from the blood into tissues where it is needed. Patients with diabetes must frequently monitor blood glucose levels and many require multiple daily insulin injections to survive. However, such patients rarely attain ideal glucose levels by insulin injection (Turner, R. C. et al. *JAMA* 281:2005 (1999)). Furthermore, prolonged elevation of insulin levels can result in detrimental side effects such as hypoglycemic shock and desensitization of the body's response to insulin. Consequently, diabetic patients still develop long-term complications, such as cardiovascular diseases, kidney disease, blindness, nerve damage and wound healing disorders (UK Prospective Diabetes Study (UKPDS) Group, *Lancet* 352:837 (1998)).

Bariatric surgery has been proposed as a potential treatment for diabetes. It has been postulated that changes in gut hormone secretion after the surgery are responsible for the resolution of diabetic conditions. The underlying molecular mechanism has yet to be elucidated, although glucagon-like peptide 1 (GLP-1) has been speculated as a possible candidate (Rubino, F. Diabetes Care 32 Suppl 2:S368 (2009)). FGF19 is highly expressed in the distal small intestine and transgenic over-expression of FGF19 improves glucose homeostasis (Tomlinson, E. Endocrinology 143(5):1741-7 (2002)). Serum levels of FGF19 in humans are elevated following gastric bypass surgery. Augmented expression and secretion of FGF19 could at least partially explain the diabetes remission experienced following surgery.

Accordingly, there is a need for alternative treatments of hyperglycemic conditions such as diabetes, prediabetes, insulin resistance, hyperinsulinemia, glucose intolerance or metabolic syndrome, and other disorders and diseases associated with elevated glucose levels, in humans. The invention satisfies this need and provides related advantages.

SUMMARY

The invention is based, in part, on variants of fibroblast growth factor 19 (FGF19) peptide sequences, fusions of fibroblast growth factor 19 (FGF19) and/or fibroblast growth factor 21 (FGF21) peptide sequences and variants of fusions (chimeras) of fibroblast growth factor 19 (FGF19) and/or fibroblast growth factor 21 (FGF21) peptide sequences having one or more activities, such as glucose lowering activity. Such variants and fusions (chimeras) of FGF19 and/or FGF21 peptide sequences include sequences that do not increase or induce hepatocellular carcinoma (HCC) formation or HCC tumorigenesis. Such variants and fusions (chimeras) of FGF19 and/or FGF21 peptide sequences also include sequences that do not induce a substantial elevation or increase in lipid profile.

In one embodiment, a chimeric peptide sequence includes or consists of: an N-terminal region having at least seven amino acid residues, the N-terminal region having a first amino acid position and a last amino acid position, where the N-terminal region has a DSSPL (SEQ ID NO:121) or DASPH (SEQ ID NO:122) sequence; and a C-terminal region having a portion of FGF19, where the C-terminal region has a first amino acid position and a last amino acid position, where the C-terminal region includes amino acid residues 16-29 of FGF19 (WGDPIRLRHLYTSG; SEQ ID NO:169), and where the W residue corresponds to the first amino acid position of the C-terminal region.

In another embodiment, a chimeric peptide sequence includes or consists of: an N-terminal region having a portion of FGF21, where the N-terminal region has a first amino acid position and a last amino acid position, where the N-terminal region has a GQV sequence, and where the V residue corresponds to the last amino acid position of the N-terminal region; and a C-terminal region including a portion of FGF19, the C-terminal region having a first amino acid position and a last amino acid position, where the C-terminal region includes amino acid residues 21-29 of FGF19 (RLRHLYTSG; SEQ ID NO:185), and where the R residue corresponds to the first position of the C-terminal region.

In a further embodiment, a chimeric peptide sequence includes or consists of any of: an N-terminal region comprising a portion of SEQ ID NO:100 [FGF21], the N-terminal region having a first amino acid position and a last amino acid position, wherein the N-terminal region comprises at least 5 (or more) contiguous amino acids of SEQ ID NO:100 [FGF21] including the amino acid residues GQV, and wherein the V residue corresponds to the last amino acid position of the N-terminal region; and a C-terminal region comprising a portion of SEQ ID NO:99 [FGF19], the C-terminal region having a first amino acid position and a last amino acid position, wherein the C-terminal region comprises amino acid residues 21-29 of SEQ ID NO:99 [FGF19], RLRHLYTSG (SEQ ID NO:185), and wherein the R residue corresponds to the first position of the C-terminal region. In particular aspects, the N-terminal region comprises at least 6 contiguous amino acids (or more, e.g., 7, 8, 9, 10, 11, 12, 13, 14, 15, 16, 17, 18, 19, 20, 20-25, 25-30, 30-40, 40-50, 50-75, 75-100 contiguous amino acids) of SEQ ID NO:100 [FGF21] including the amino acid residues GQV.

In an additional embodiment, a peptide sequence includes or consists of any of: a fibroblast growth factor 19 (FGF19) sequence variant having one or more amino acid substitutions, insertions or deletions compared to a reference or wild type FGF19; a fibroblast growth factor 21 (FGF21) sequence variant having one or more amino acid substitutions, insertions or deletions compared to a reference or wild type FGF21; a portion of an FGF19 sequence fused to a portion of an FGF21 sequence; or a portion of an FGF19 sequence fused to a portion of an FGF21 sequence, wherein the FGF19 and/or FGF21 sequence portion(s) have one or more amino acid substitutions, insertions or deletions compared to a reference or wild type FGF19 and/or FGF21.

In still further embodiments, a peptide sequence or a chimeric peptide sequence includes or consists of amino-terminal amino acids 1-16 of SEQ ID NO:100 [FGF21] fused to carboxy-terminal amino acids 21-194 of SEQ ID NO:99 [FGF19], or the peptide sequence has amino-terminal amino acids 1-147 of SEQ ID NO:99 [FGF19] fused to carboxy-terminal amino acids 147-181 of SEQ ID NO:100 [FGF21] (M41), or the peptide sequence has amino-terminal amino acids 1-20 of SEQ ID NO:99 [FGF19] fused to carboxy-terminal amino acids 17-181 of SEQ ID NO:100 [FGF21] (M44), or the peptide sequence has amino-terminal amino acids 1-146 of SEQ ID NO:100 [FGF21] fused to carboxy-terminal amino acids 148-194 of SEQ ID NO:99 [FGF19] (M45), or the peptide sequence has amino-terminal amino acids 1-20 of SEQ ID NO:99 [FGF19] fused to internal amino acids 17-146 of SEQ ID NO:100 [FGF21] fused to carboxy-terminal amino acids 148-194 of SEQ ID NO:99 [FGF19] (M46).

In yet additional embodiments, a peptide sequence or a chimeric peptide sequence has a WGDPI (SEQ ID NO:170) sequence motif corresponding to the WGDPI (SEQ ID NO:170) sequence of amino acids 16-20 of SEQ ID NO:99 [FGF19], or has a substituted, mutated or absent WGDPI (SEQ ID NO:170) sequence motif corresponding to FGF19 WGDPI (SEQ ID NO:170) sequence of amino acids 16-20 of FGF19, or the WGDPI (SEQ ID NO:170) sequence motif has one or more amino acids substituted, mutated or absent; or is distinct from an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the FGF19 WGDPI (SEQ ID NO:170) sequence at amino acids 16-20.

In yet further embodiments, a peptide sequence or a chimeric peptide sequence has an N-terminal region that includes or consists of amino acid residues VHYG (SEQ ID NO:101), where the N-terminal region comprises amino acid residues DASPHVHYG (SEQ ID NO:102), or where the N-terminal region comprises amino acid residues DSSPLVHYG (SEQ ID NO:103), or where the N-terminal region comprises amino acid residues DSSPLLQ (SEQ ID NO:104), or where the N-terminal region comprises amino acid residues DSSPLLQFGGQV (SEQ ID NO:105). In particular aspects, the G corresponds to the last position of the N-terminal region, or the Q residue is the last amino acid position of the N-terminal region, or the V residue corresponds to the last position of the N-terminal region.

In still additional embodiments, a peptide sequence or a chimeric peptide sequence has an N-terminal region that includes or consists of RHPIP (SEQ ID NO:106), where R is the first amino acid position of the N-terminal region; or HPIP (SEQ ID NO:107) (e.g., where HPIP (SEQ ID NO:107) are the first 4 amino acid residues of the N-terminal region), where H is the first amino acid position of the N-terminal region; or RPLAF (SEQ ID NO:108), where R is the first amino acid position of the N-terminal region; or PLAF (SEQ ID NO:109), where P is the first amino acid position of the N-terminal region; or R, where R is the first amino acid position of the N-terminal region, or has at the N-terminal region any one of the following sequences: MDSSPL (SEQ ID NO:110), MSDSSPL (SEQ ID NO:111), SDSSPL (SEQ ID NO:112), MSSPL (SEQ ID NO:113) or SSPL (SEQ ID NO:114).

In other embodiments, a peptide sequence or a chimeric peptide sequence has, at the first position of the N-terminal region, an "M" residue, an "R" residue, a "S" residue, a "H" residue, a "P" residue, a "L" residue or an "D" residue. In alternative embodiments, a peptide sequence or a chimeric peptide sequence does not have a "M" residue or an "R" residue at the first amino acid position of the N-terminal region.

In still other embodiments, a peptide sequence or a chimeric peptide sequence has at the first and second positions of the N-terminal region an MR sequence, or at the first and second positions of the N-terminal region an RM sequence, or at the first and second positions of the N-terminal region an RD sequence, or at the first and second positions of the N-terminal region an DS sequence, or at the first and second positions of the N-terminal region an MD sequence, or at the first and second positions of the N-terminal region an MS sequence, or at the first through third positions of the N-terminal region an MDS sequence, or at the first through third positions of the N-terminal region an RDS sequence, or at the first through third positions of the N-terminal region an MSD sequence, or at the first through third positions of the N-terminal region an MSS sequence, or at the first through third positions of the N-terminal region an DSS sequence, or at the first through fourth positions of the N-terminal region an RDSS (SEQ ID NO:115) sequence, or at the first through fourth positions of the N-terminal region an MDSS (SEQ ID NO:116) sequence, or at the first through fifth positions of the N-terminal region an MRDSS (SEQ ID NO:117) sequence, or at the first through fifth positions of the N-terminal region an MSSPL (SEQ ID NO:113) sequence, or at the first through sixth positions of the N-terminal region an MDSSPL (SEQ ID NO:110) sequence, or at the first through seventh positions of the N-terminal region an MSDSSPL (SEQ ID NO:111) sequence.

In still other embodiments, a peptide sequence or a chimeric peptide sequence an addition of amino acid residues 30-194 of SEQ ID NO:99 [FGF19] at the C-terminus, resulting in a chimeric polypeptide having at the last position of the C-terminal region that corresponds to about residue 194 of SEQ ID NO:99 [FGF19]. In further other embodiments, a chimeric peptide sequence or peptide sequence comprises all or a portion of an FGF19 sequence (e.g., SEQ ID NO:99), positioned at the C-terminus of the peptide, or where the amino terminal "R" residue is deleted from the peptide.

In more particular embodiments, a chimeric peptide sequence or peptide sequence includes or consists of any of M1-M98 variant peptide sequences, or a subsequence or fragment of any of the M1-M98 (SEQ ID NOS:1-52, 192, and 54-98, respectively variant peptide sequences.

In additional particular embodiments, a chimeric peptide sequence or peptide sequence has an N-terminal or a C-terminal region from about 20 to about 200 amino acid residues in length. In further particular embodiments, a chimeric peptide sequence or peptide sequence has at least one amino acid deletion. In still further particular embodiments, a chimeric peptide sequence or peptide sequence, or a subsequence or fragment thereof, has 1, 2, 3, 4, 5, 6, 7, 8, 9, 10, 11, 12, 13, 14, 15, 16, 17, 18, 19, 20 or more amino acid deletions from the amino terminus, the carboxy-terminus or internally. In a particular non-limiting aspect, the amino acid substitution, or deletion is at any of amino acid positions 8-20 of FGF19 (AGPHVHYGWGDPI; SEQ ID NO:187).

In more particular embodiments, a chimeric peptide sequence or peptide sequence includes or consists of an amino acid sequence of about 5 to 10, 10 to 20, 20 to 30, 30 to 40, 40 to 50, 60 to 70, 70 to 80, 80 to 90, 90 to 100 or more amino acids. In more particular embodiments, a chimeric peptide sequence or peptide sequence includes or consists of an amino acid sequence of about 5 to 10, 10 to 20, 20 to 30, 30 to 40, 40 to 50, 50 to 60, 60 to 70, 70 to 80, 80 to 90, 90 to 100 or more amino acids of FGF19 or FGF21.

In further particular embodiments, chimeric peptide sequences and peptide sequences have particular functions or activities. In one aspect, a chimeric peptide sequence or peptide sequence maintains or increases an FGFR4 mediated activity. In additional aspects, a chimeric peptide sequence or peptide sequence binds to fibroblast growth factor receptor 4 (FGFR4) or activates FGFR4, or does not detectably bind to fibroblast growth factor receptor 4 (FGFR4) or activate FGFR4, or binds to FGFR4 with an affinity less than, comparable to or greater than FGF19 binding affinity for FGFR4, or activates FGFR4 to an extent or amount less than, comparable to or greater than FGF19 activates FGFR4. In further aspects, a chimeric peptide sequence or peptide sequence has reduced hepatocellular carcinoma (HCC) formation compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19, and/or has greater glucose lowering activity compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19, and/or has less lipid increasing activity compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19, and/or has less triglyceride, cholesterol, non-HDL or HDL increasing activity compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19, and/or has less lean mass reducing activity compared to FGF21. Such functions and activities can be ascertained in vitro or in vivo, for example, in a db/db mouse.

In still additional embodiments, chimeric peptide sequences and peptide sequences isolated or purified, and/or chimeric peptide sequences and peptide sequences can be included in compositions. In one embodiment, a chimeric peptide sequence or peptide sequence is included in a pharmaceutical composition. Such compositions include combinations of inactive or other active ingredients. In one embodiment, a compositions, such as a pharmaceutical composition includes chimeric peptide sequence or peptide sequence and a glucose lowering agent.

In yet further embodiments, nucleic acid molecules encoding the chimeric peptide sequence or peptide sequence are provided. Such molecules can further include an expression control element in operable linkage that confers expression of the nucleic acid molecule encoding the peptide in vitro, in a cell or in vivo, or a vector comprising the nucleic acid molecule (e.g., a viral vector). Transformed and host cells that express the chimeric peptide sequences and peptide sequences are also provided.

Uses and methods of treatment that include administration or delivery of any chimeric peptide sequence or peptide sequence are also provided. In particular embodiments, a use or method of treatment of a subject includes administering an invention chimeric peptide or peptide sequence to a subject, such as a subject having, or at risk of having, a disease or disorder treatable by an invention peptide sequence, in an amount effective for treating the disease or disorder. In a further embodiment, a method includes administering an invention chimeric peptide or peptide sequence to a subject, such as a subject having a hyperglycemic condition (e.g., diabetes, such as insulin-dependent (type I) diabetes, type II diabetes, or gestational diabetes), insulin resistance, hyperinsulinemia, glucose intolerance or metabolic syndrome, or is obese or has an undesirable body mass.

In particular aspects of the methods and uses, a chimeric peptide sequence or peptide sequence is administered to a subject in an amount effective to improve glucose metabolism in the subject. In more particular aspects, a subject has a fasting plasma glucose level greater than 100 mg/dl or has a hemoglobin A1c (HbA1c) level above 6%, prior to administration.

In further embodiments, a use or method of treatment of a subject is intended to or results in reduced glucose levels, increased insulin sensitivity, reduced insulin resistance, reduced glucagon, an improvement in glucose tolerance, or glucose metabolism or homeostasis, improved pancreatic function, or reduced triglyceride, cholesterol, IDL, LDL or VLDL levels, or a decrease in blood pressure, a decrease in intimal thickening of the blood vessel, or a decrease in body mass or weight gain.

Methods of analyzing and/or identifying a chimeric peptide sequence or peptide sequence are also provided, such as chimeric peptide sequences and peptide sequences that have glucose lowering activity without substantial hepatocellular carcinoma (HCC) activity. In one embodiment, a method includes: a) providing a candidate chimeric peptide sequence or peptide sequence; b) administering the candidate peptide sequence to a test animal (e.g., a db/db mouse); c) measuring glucose levels of the animal after administration of the candidate peptide sequence, to determine if the candidate peptide sequence reduces glucose levels. In a particular aspect, the chimeric peptide sequence or peptide sequence is also analyzed for induction of HCC in the animal (e.g., assessing a hepatic tissue sample from the test animal), or expression of a marker correlating with HCC activity, wherein a candidate peptide having glucose lowering activity and not substantial HCC activity. Such methods identify the candidate as having glucose lowering activity, optionally also without substantial hepatocellular carcinoma (HCC) activity.

DESCRIPTION OF DRAWINGS

FIG. 1 shows representative domain exchanges between FGF21 (no shading) and FGF19 (grey shading) protein sequences, and the resultant fusion (chimeric) sequences. The amino acid regions from each of FGF21 and FGF19 present in the fusion (chimera) are indicated by the numbers. Glucose lowering and lipid elevation are shown for each of the chimeric sequences.

FIGS. 2A-2I show glucose lowering and body weight data. A) variant M5; B) variant M1; C) variant M2 and variant M69; D) variant M3; E) variant M48 and variant M49; F) variant M51 and variant M50; G) variant M52 peptide; H) variant M53 peptide; and I) variant M70 peptide sequences all have glucose lowering (i.e., anti-diabetic) activity in db/db mice. Mice were injected with AAV vector expressing FGF19, FGF21, the selected variants, and saline and GFP are negative controls.

FIGS. 3A-3I show serum lipid profile (triglyceride, total cholesterol, HDL and non-HDL) of db/db mice injected with AAV vector expressing FGF19, FGF21 or A) variant M5; B) variant M1; C) variant M2 and variant M69; D) variant M3; E) variant M48 and variant M49; F) variant M51 and variant M50; G) variant M52 peptide; H) variant M53 peptide; and I) variant M70 peptide sequences. Variant M5 peptide sequence did not increase or elevate lipids, in contrast to FGF19, M1, M2 and M69 which increases and elevates lipids. Serum levels of all variants were comparable. Saline and GFP are negative controls.

DETAILED DESCRIPTION

Figure 2A:
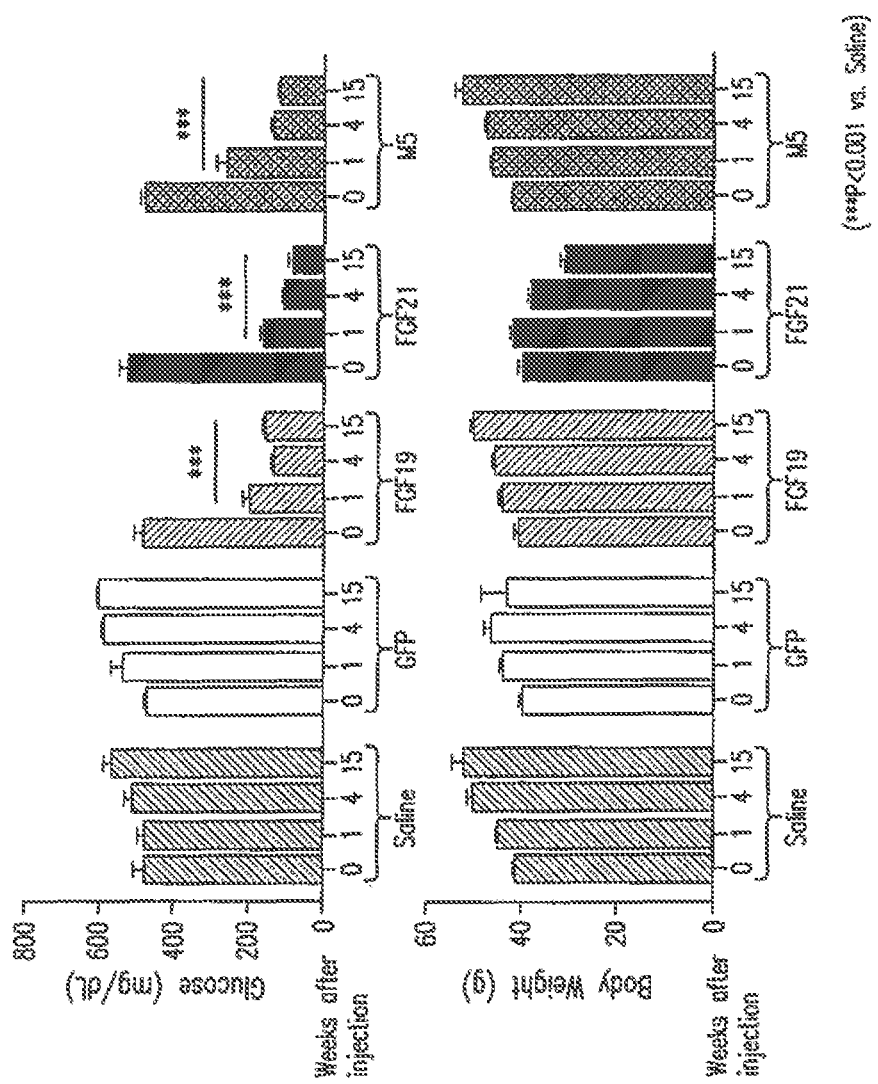

The invention provides chimeric and peptide sequences that are able to lower or reduce levels of glucose. In one embodiment, a chimeric peptide sequence includes or consists of an N-terminal region having at least seven amino acid residues and the N-terminal region having a first amino acid position and a last amino acid position, where the N-terminal region has a DSSPL (SEQ ID NO:121) or DASPH (SEQ ID NO:122) sequence; and a C-terminal region having a portion of FGF19 and the C-terminal region having a first amino acid position and a last amino acid position, where the C-terminal region includes amino acid residues 16-29 of FGF19 (WGDPIRLRHLYTSG; SEQ ID NO:169) and the W residue corresponds to the first amino acid position of the C-terminal region.

In another embodiment, a chimeric peptide sequence includes or consists of an N-terminal region having a portion of FGF21 and the N-terminal region having a first amino acid position and a last amino acid position, where the N-terminal region has a GQV sequence and the V residue corresponds to the last amino acid position of the N-terminal region; and a C-terminal region having a portion of FGF19 and the C-terminal region having a first amino acid position and a last amino acid position where the C-terminal region includes amino acid residues 21-29 of FGF19 (RLRHLYTSG; SEQ ID NO:185) and the R residue corresponds to the first position of the C-terminal region.

In further embodiments, a peptide sequence includes or consists of a fibroblast growth factor 19 (FGF19) sequence variant having one or more amino acid substitutions, insertions or deletions compared to a reference or wild type FGF19. In additional embodiments, a peptide sequence includes or consists of a fibroblast growth factor 21 (FGF21) sequence variant having one or more amino acid substitutions, insertions or deletions compared to a reference or wild type FGF21. In yet additional embodiments, a peptide sequence includes or consists of a portion of an FGF19 sequence fused to a portion of an FGF21 sequence. In still additional embodiments, a peptide sequence includes or consists of a portion of an FGF19 sequence fused to a portion of an FGF21 sequence, where the FGF19 and/or FGF21 sequence portion(s) have one or more amino acid substitutions, insertions or deletions compared to a reference or wild type FGF19 and/or FGF21.

The invention also provides methods and uses of treating a subject having or at risk of having a metabolic disorder treatable using variants and fusions of fibroblast growth factor 19 (FGF19) and/or fibroblast growth factor 21 (FGF21) peptide sequences. In one embodiment, a method includes contacting or administering to a subject one or more variant or fusion fibroblast growth factor 19 (FGF19) and/or fibroblast growth factor 21 (FGF21) peptide sequences in an amount effective for treating the disorder. In another embodiment, a method includes contacting or administering to a subject one or more nucleic acid molecules encoding a variant or fusion fibroblast growth factor 19 (FGF19) and/or fibroblast growth factor 21 (FGF21) peptide sequence (for example, an expression control element in operable linkage with the nucleic acid encoding the peptide sequence, optionally including a vector), in an amount effective for treating the disorder.

Although an understanding of the underlying mechanism of action of the invention peptides is not required in order to practice the invention, without being bound to any particular theory or hypothesis, it is believed that invention peptides mimic, at least in part, the effect that bariatric surgery has on, for example, glucose homeostasis and weight loss. Changes in gastrointestinal hormone secretion (e.g., glucagon-like peptide 1 (GLP-1)) after bariatric surgery are believed responsible for the resolution of, for example, diabetic conditions. FGF19 is highly expressed in the distal small intestine, and transgenic over-expression of FGF19 improves glucose homeostasis. Because levels of FGF19 in humans are also elevated following gastric bypass surgery, the elevated FGF19 might be involved with the remission of diabetes observed following bariatric surgery.

A representative reference or wild type FGF19 sequence is set forth as:

(SEQ ID NO: 99)
RPLAFSDAGPHVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK.

A representative reference or wild type FGF21 sequence is set forth as:

(SEQ ID NO: 100)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHGLPLHLPGNKSPHRDPAPRGPARFLPLPGLPPALPEPP
GILAPQPPDVGSSDPLSMVGPSQGRSPSYAS.

Representative variant sequences, namely variant M1, variant M2, variant M3, variant M5, variant M48, variant M49, variant M50, variant M51, variant M52, variant M53, variant M69, and variant M70 peptide sequences are shown below:

(M1; SEQ ID NO: 1)
RPLAFSDASPHVHYGWGDPIRLRHLYTSGPHGLSSCFLRIRADGVVDCARGQSAHSLLEIKA
VALRTVAIKGVHSVRYLCMGADGKMQGLLQYSEEDCAFEEEIRPDGYNVYRSEKHRLPVSL
SSAKQRQLYKNRGFLPLSHFLPMLPMVPEEPEDLRGHLESDMFSSPLETDSMDPFGLVTGLE
AVRSPSFEK (M2; SEQ ID NO: 2)
RPLAFSDSSPLVHYGWGDPIRLRHLYTSGPHGLSSCFLRIRADGVVDCARGQSAHSLLEIKAV
ALRTVAIKGVHSVRYLCMGADGKMQGLLQYSEEDCAFEEEIRPDGYNVYRSEKEIRLPVSLS
SAKQRQLYKNRGFLPLSHFLPMLPMVPEEPEDLRGHLESDMFSSPLETDSMDPFGLVTGLEA
VRSPSFEK (M3; SEQ ID NO: 3)
RPLAFSDAGPHVHYGWGDPIRLRHLYTSGPHGLSSCFLRIRADGVVDCARGQSAHSLLEIKA
VALRTVAIKGVHSVRYLCMGADGKMQGLLQYSEEDCAFEEEILEDGYNVYRSEKHRLPVSL
SSAKQRQLYKNRGFLPLSHFLPMLPMVPEEPEDLRGHLESDMFSSPLETDSMDPFGLVTGLE
AVRSPSFEK (M5; SEQ ID NO: 5)
RHPIPDSSPLLQFGGQVRLRHLYTSGPHGLSSCFLRIRADGVVDCARGQSAHSLLEIKAVALR
TVAIKGVHSVRYLCMGADGKMQGLLQYSEEDCAFEEEIRPDGYNVYRSEKHRLPVSLSSAK
QRQLYKNRGFLPLSHFLPMLPMVPEEPEDLRGHLESDMFSSPLETDSMDPFGLVTGLEAVRS
PSFEK (M48; SEQ ID NO: 48)
RDSSPLLQFGGQVRLRHLYTSGPHGLSSCFLRIRADGVVDCARGQSAHSLLEIKAVALRTVAI
KGVHSVRYLCMGADGKMQGLLQYSEEDCAFEEEIRPDGYNVYRSEKHRLPVSLSSAKQRQ
LYKNRGFLPLSHFLPMLPMVPEEPEDLRGHLESDMFSSPLETDSMDPFGLVTGLEAVRSPSFEK (M49; SEQ ID NO: 49)
RPLAFSDSSPLLQFGGQVRLRHLYTSGPHGLSSCFLRIRADGVVDCARGQSAHSLLEIKAVAL
RTVAIKGVHSVRYLCMGADGKMQGLLQYSEEDCAFEEEIRPDGYNVYRSEKHRLPVSLSSA
KQRQLYKNRGFLPLSHFLPMLPMVPEEPEDLRGHLESDMFSSPLETDSMDPFGLVTGLEAVR
SPSFEK (M50; SEQ ID NO: 50)
RHPIPDSSPLLQFGDQVRLRHLYTSGPHGLSSCFLRIRADGVVDCARGQSAHSLLEIKAVALR
TVAIKGVHSVRYLCMGADGKMQGLLQYSEEDCAFEEEILEDGYNVYRSEKHRLPVSLSSAK
QRQLYKNRGFLPLSHFLPMLPMVPEEPEDLRGHLESDMFSSPLETDSMDPFGLVTGLEAVRS
PSFEK

```
                                                        (M51; SEQ ID NO: 51)
RHPIPDSSPLLQFGGNVRLRHLYTSGPHGLSSCFLRIRADGVVDCARGQSAHSLLEIKAVALR

TVAIKGVHSVRYLCMGADGKMQGLLQYSEEDCAFEEEIRPDGYNVYRSEKHRLPVSLSSAK

QRQLYKNRGFLPLSHFLPMLPMVPEEPEDLRGHLESDMFSSPLETDSMDPFGLVTGLEAVRS

PSFEK (M52; SEQ ID NO: 52)
RDSSPLLQWGDPIRLRHLYTSGPHGLSSCFLRIRADGVVDCARGQSAHSLLEIKAVALRTVAI

KGVHSVRYLCMGADGKMQGLLQYSEEDCAFEEEIRPDGYNVYRSEKHRLPVSLSSAKQRQ

LYKNRGFLPLSHFLPMLPMVPEEPEDLRGHLESDMFSSPLETDSMDPFGLVTGLEAVRSPSFEK (M53; SEQ ID NO: 53)
MDSSPLLQWGDPIRLRHLYTSGPHGLSSCFLRIRADGVVDCARGQSAHSLLEIKAVALRTVA

IKGVHSVRYLCMGADGKMQGLLQYSEEDCAFEEEIRPDGYNVYRSEKHRLPVSLSSAKQRQ

LYKNRGFLPLSHFLPMLPMVPEEPEDLRGHLESDMFSSPLETDSMDPFGLVTGLEAVRSPSFEK (M69; SEQ ID NO: 69)
RDSSPLVHYGWGDPIRLRHYTSGPHGLSSCFLRIRADGVVDCARGQSAHSLLEIKAVALRT

VAIKGVHSVRYLCMGADGKMQGLLQYSEEDCAFEEEIRPDGYNVYRSEKHRLPVSLSSAKQ

RQLYKNRGFLPLSHFLPMLPMVPEEPEDLRGHLESDMFSSPLETDSMDPFGLVTGLEAVRSP

SFEK (M70; SEQ ID NO: 70)
MRDSSPLVHYGWGDPIRLRHLYTSGPHGLSSCFLRIRADGVVDCARGQSAHSLLEIKAVALR

TVAIKGVHSVRYLCMGADGKMQGLLQYSEEDCAFEEEIRPDGYNVYRSEKHRLPVSLSSAK

QRQLYKNRGFLPLSHFLPMLPMVPEEPEDLRGHLESDMFSSPLETDSMDPFGLVTGLEAVRS

PSFEK
```

Three additional allelic (polymorphic) forms of FGF21, namely M71, M72 and M73 are also shown below:

```
                                                        (M71; SEQ ID NO: 71)
HPIPDSSPLLQFGGQVRQRYLYTDDAQQTEAHLEIREDGTVGGAADQSPE

SLLQLKALKPGVIQILGVKTSRFLCQRPDGALYGSLHFDPEACSFRELLL

EDGYNVYQSEAHSLPLHLPGNKSPHRDPAPRGPARFLPLPGLPPALPEPP

GILAPQPPDVGSSDPLSMVGPSQGRSPSYAS (M72; SEQ ID NO: 72)
HPIPDSSPLLQFGGQVRQRYLYTDDAQQTEAHLEIREDGTVGGAADQSPE

SLLQLKALKPGVIQILGVKTSRFLCQRPDGALYGSLHFDPEACSFRELLL

EDGYNVYQSEAHGLPLHLPGNKSPHRDPAPRGPARFLPLPGLPPAPPEPP

GILAPQPPDVGSSDPLSMVGPSQGRSPSYAS (M73; SEQ ID NO: 73)
HPIPDSSPLLQFGGQVRQRYLYTDDAQQTEAHLEIREDGTVGGAADQSPE

SLLQLKALKPGVIQILGVKTSRFLCQRPDGALYGSLHFDPEACSFRELLL

EDGYNVYQSEAHGLPLHLPGNKSPHRDPAPRGPARFLPLPGLPPALPEPP

GILAPQPPDVGSSDPLSMVVQDELQGVGGEGCHMHPENCKTLLTDIDRTH

TEKPVWDGITGE
```

FGF21 allelic variants are illustrated above (e.g., M70, M71 and M72).

The terms "peptide," "protein," and "polypeptide" sequence are used interchangeably herein to refer to two or more amino acids, or "residues," including chemical modifications and derivatives of amino acids, covalently linked by an amide bond or equivalent. The amino acids forming all or a part of a peptide may be from among the known 21 naturally occurring amino acids, which are referred to by both their single letter abbreviation or common three-letter abbreviation. In the peptide sequences of the invention, conventional amino acid residues have their conventional meaning. Thus, "Leu" is leucine, "Ile" is isoleucine, "Nle" is norleucine, and so on.

Figure 1:
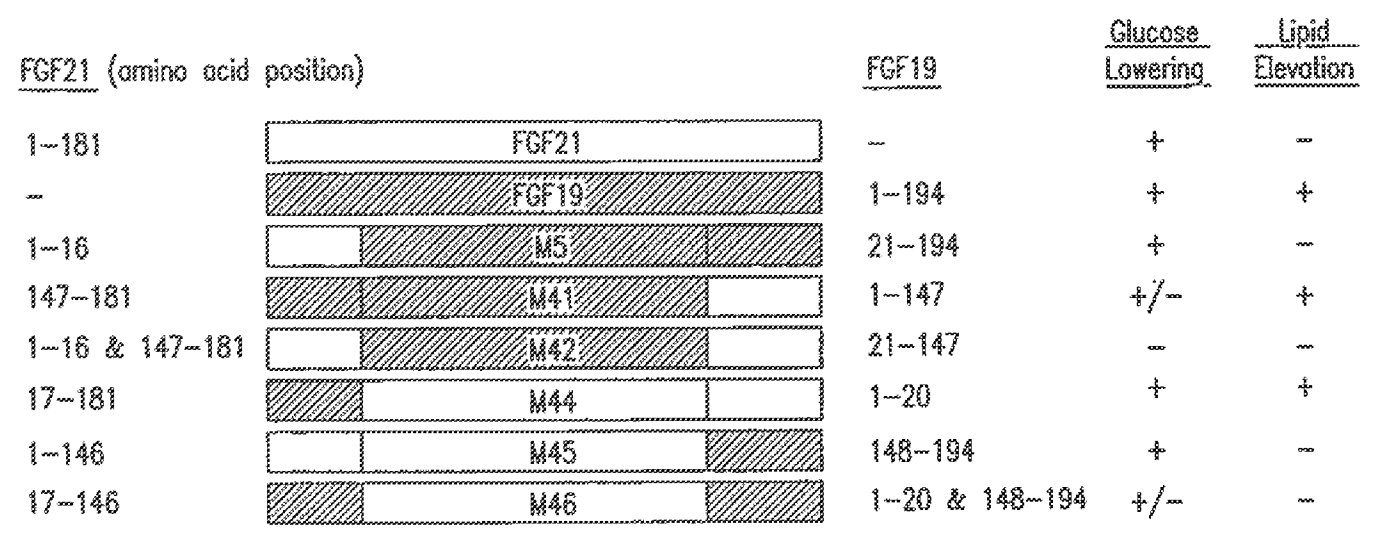

Exemplified herein are peptide sequences, distinct from reference FGF19 and FGF21 polypeptides set forth herein, that reduce or lower glucose, in vivo (Tables 1-8 and FIG. 1 SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)). Non-limiting particular examples are a peptide sequence with amino-terminal amino acids 1-16 of FGF21 fused to carboxy-terminal amino acids 21-194 of FGF19; a peptide sequence with amino-terminal amino acids 1-147 of FGF19 fused to carboxy-terminal amino acids 147-181 of FGF21; a peptide sequence with amino-terminal amino acids 1-20 of FGF19 fused to carboxy-terminal amino acids 17-181 of FGF21; a peptide sequence with amino-terminal amino acids 1-146 of FGF21 fused to carboxy-terminal amino acids 148-194 of FGF19; and a peptide sequence with amino-terminal amino acids 1-20 of FGF19 fused to internal amino acids 17-146 of FGF21 fused to carboxy-terminal amino acids 148-194 of FGF19.

Additional particular peptides sequences have a WGDPI (SEQ ID NO:170) sequence motif corresponding to the WGDPI (SEQ ID NO:170) sequence of amino acids 16-20 of FGF19 (SEQ ID NO:99), lack a WGDPI sequence motif corresponding to the WGDPI (SEQ ID NO:170) sequence of amino acids 16-20 of FGF19 (SEQ ID NO:99), or have a substituted (i.e., mutated) WGDPI (SEQ ID NO:170) sequence motif corresponding to FGF19 WGDPI (SEQ ID NO:170) sequence of amino acids 16-20 of FGF19 (SEQ ID NO:99).

Particular peptide sequences of the invention also include sequences distinct from FGF19 and FGF21 (e.g., as set forth herein), and FGF 19 variant sequences having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for FGF19 WGDPI (SEQ ID NO:170) sequence at amino acids 16-20. Accordingly, the wild-type FGF19 and FGF21 (e.g., as set forth herein as SEQ ID NOS:99 and 100, respectively) may be excluded sequences, and FGF19 having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19 may also be excluded. This exclusion, however, does not apply to where a sequence has, for example, 3 FGF21 residues fused to FGF19 having, for example, any of GQV, GQV, GDI, or GPI, or 2 FGF21 residues fused to any of WGPI (SEQ ID NO:171), WGDI (SEQ ID NO:173), GDPI (SEQ ID NO:174), WDPI (SEQ ID NO:181), WGDI (SEQ ID NO:182), or WGDP (SEQ ID NO:183).

Particular non-limiting examples of peptide sequences include or consist of all or a part of a sequence variant specified herein as M1-M98 (SEQ ID NOs:1-52, 192, and 54-98, respectively). More particular non-limiting examples of peptide sequences include or consist of all or a part of a sequence set forth as:
HPIPDSSPLLQFGGQVRLRHLYTSGPHGLSSCFLRI-RADGVVDCARGQSAHSLLEIKAVALRT VAIKGVHS-VRYLCMGADGKMQGLLQYSEEDCAFEEEIRPDGYN-VYRSEKHRLPVSLSSAKQ RQLYKNRGFLPLSHFLPMLPMVPEEPEDLRGHLESD-MFSSPLETDSMDPFGLVTGLEAVRSP SFEK (SEQ ID NO:160) (FGF21 sequences can also include an "R" residue at the amino terminus), or a subsequence or fragment thereof; or
DSSPLLQFGGQVRLRHLYTSGPHGLSSCFLRIRADGV-VDCARGQSAHSLLEIKAVALRTVAI KGVHSVRYLCM-GADGKMQGLLQYSEEDCAFEEEIRPDGYN-VYRSEKHRLPVSLSSAKQRQ LYKNRGFLPLSHFLPMLPMVPEEPEDLRGHLESDMF-SSPLETDSMDPFGLVTGLEAVRSPSFEK (SEQ ID NO:161), or a subsequence or fragment thereof; or
RPLAFSDASPHVHYGWGDPIRLRHLYTSGPHGLSSC-FLRIRADGVVDCARGQSAHSLLEIKA VALRTVAIK-GVHSVRYLCMGADGKMQGLLQYSEEDCAFEEEIRP-DGYNVYRSEKHRLPVSL SSAKQRQLYKNRGFLPLSHFLPMLPMVPEEPEDL-RGHLESDMFSSPLETDSMDPFGLVTGLE AVRSPSFEK (M1) (SEQ ID NO:1), or a subsequence or fragment thereof; or
RPLAFSDSSPLVHYGWGDPIRLRHLYTSGPHGLSSC-FLRIRADGVVDCARGQSAHSLLEIKAV ALRTVAIK-GVHSVRYLCMGADGKMQGLLQYSEEDCAFEEEIRP-DGYNVYRSEKHRLPVSLS SAKQRQLYKNRGFLPLSHFLPMLPMVPEEPEDL-RGHLESDMFSSPLETDSMDPFGLVTGLEA VRSPSFEK (M2) (SEQ ID NO:2), or a subsequence or fragment thereof; or
DSSPLVHYGWGDPIRLRHLYTSGPHGLSSCFLRI-RADGVVDCARGQSAHSLLEIKAVALRTV AIKGVHS-VRYLCMGADGKMQGLLQYSEEDCAFEEEIRPDGYN-VYRSEKHRLPVSLSSAKQR QLYKNRGFLPLSHFLPMLPMVPEEPEDLRGHLESD-MFSSPLETDSMDPFGLVTGLEAVRSPSFEK (SEQ ID NO:141), or a subsequence or fragment thereof; or
RDSSPLVHYGWGDPIRLRHLYTSGPHGLSSCFLRI-RADGVVDCARGQSAHSLLEIKAVALRT VAIKGVHS-VRYLCMGADGKMQGLLQYSEEDCAFEEEIRPDGYN-VYRSEKHRLPVSLSSAKQ RQLYKNRGFLPLSHFLPMLPMVPEEPEDLRGHLESD-MFSSPLETDSMDPFGLVTGLEAVRSP SFEK (M69) (SEQ ID NO:69), or a subsequence or fragment thereof; or
RDSSPLLQWGDPIRLRHLYTSGPHGLSSCFLRI-RADGVVDCARGQSAHSLLEIKAVALRTVAI KGVHS-VRYLCMGADGKMQGLLQYSEEDCAFEEEIRPDGYN-VYRSEKHRLPVSLSSAKQRQ LYKNRGFLPLSHFLPMLPMVPEEPEDLRGHLESDMF-SSPLETDSMDPFGLVTGLEAVRSPSFEK (M52) (SEQ ID NO: 52), or a subsequence or fragment thereof; or
HPIPDSSPLLQFGGQVRLRHLYTSGPHGLSSCFLRI-RADGVVDCARGQSAHSLLEIKAVALRT VAIKGVHS-VRYLCMGADGKMQGLLQYSEEDCAFEEEIRPDGYN-VYRSEKHRLPVSLSSAKQ RQLYKNRGFLPLSHFLPMLPMVPEEPEDLRGHLESD-MFSSPLETDSMDPFGLVTGLEAVRSPSFEK (SEQ ID NO:160), or a subsequence or fragment thereof;
HPIPDSSPLLQFGGQVRQRYLYTDDAQQTEAHL-EIREDGTVGGAADQSPESLLQLKALKPGV IQILGVK-TSRFLCQRPDGALYGSLHFDPEACSFRELLLEDGYN-VYQSEAHSLPLHLPGNKSPH RDPAPRGPARFLPLPGLPPALPEPPGILAPQPPDVGSS-DPLSMVGPSQGRSPSYAS (M71) (SEQ ID NO:71), or a subsequence or fragment thereof; or
HPIPDSSPLLQFGGQVRQRYLYTDDAQQTEAHL-EIREDGTVGGAADQSPESLLQLKALKPGV IQILGVK-TSRFLCQRPDGALYGSLHFDPEACSFRELLLEDGYN-VYQSEAHGLPLHLPGNKSPH RDPAPRGPARFLPLPGLPPAPPEPPGILAPQPPDVGSS-DPLSMVGPSQGRSPSYAS (M72) (SEQ ID NO:72), or a subsequence or fragment thereof; or
HPIPDSSPLLQFGGQVRQRYLYTDDAQQTEAHL-EIREDGTVGGAADQSPESLLQLKALKPGV IQILGVK-TSRFLCQRPDGALYGSLHFDPEACSFRELLLEDGYN-VYQSEAHGLPLHLPGNKSPH RDPAPRGPARFLPLPGLPPALPEPPGILAPQPPDVGSS-DPLSMVQDELQGVGGEGCHMHPE NCKTLLT-DIDRTHTEKPVWDGITGE (M73) (SEQ ID NO:73), or a subsequence or fragment thereof; or
RPLAFSDASPHVHYGWGDPIRLRHLYTSGPHGLSSC-FLRIRADGVVDCARGQSAHSLLEIKA VALRTVAIK-GVHSVRYLCMGADGKMQGLLQYSEEDCAFEEEIRP-DGYNVYRSEKHRLPVSL SSAKQRQLYKNRGFLPLSHFLPMLPMVPEEPEDL-RGHLESDMFSSPLETDSMDPFGLVTGLE AVRSPSFEK (M1) (SEQ ID NO:1), or a subsequence or fragment thereof; or RPLAFSDSSPLVHYGWGDPIRLRHLYTSGPHGLSSC-FLRIRADGVVDCARGQSAHSLLEIKAV ALRTVAIK-GVHSVRYLCMGADGKMQGLLQYSEEDCAFEEEIRP-DGYNVYRSEKHRLPVSLS SAKQRQLYKNRGFLPLSHFLPMLPMVPEEPEDL-RGHLESDMFSSPLETDSMDPFGLVTGLEA VRSPSFEK (M2) (SEQ ID NO:2), or a subsequence or fragment thereof; or
RPLAFSDAGPHVHYGWGDPIRLRHLYTSGPHGLSSC-FLRIRADGVVDCARGQSAHSLLEIKA VALRTVAIK-GVHSVRYLCMGADGKMQGLLQYSEEDCAFEEE-ILEDGYNVYRSEKHRLPVSL SSAKQRQLYKNRGFLPLSHFLPMLPMVPEEPEDL-RGHLESDMFSSPLETDSMDPFGLVTGLE AVRSPSFEK (M3) (SEQ ID NO:3), or a subsequence or fragment thereof; or
RDSSPLLQFGGQVRLRHLYTSGPHGLSSCFLRI-RADGVVDCARGQSAHSLLEIKAVALRTVAI KGVHS-VRYLCMGADGKMQGLLQYSEEDCAFEEEIRPDGYN-VYRSEKHRLPVSLSSAKQRQ LYKNRGFLPLSHFLPMLPMVPEEPEDLRGHLESDMF-SSPLETDSMDPFGLVTGLEAVRSPSFEK (M48) (SEQ ID NO:48), or a subsequence or fragment thereof; or
RPLAFSDSSPLLQFGGQVRLRHLYTSGPHGLSSCFL-RIRADGVVDCARGQSAHSLLEIKAVAL RTVAIK-GVHSVRYLCMGADGKMQGLLQYSEEDCAFEEEIRP-DGYNVYRSEKHRLPVSLSSA KQRQLYKNRGFLPLSHFLPMLPMVPEEPEDL-RGHLESDMFSSPLETDSMDPFGLVTGLEAVR SPSFEK (M49) (SEQ ID NO:49), or a subsequence or fragment thereof; or
RHPIPDSSPLLQFGDQVRLRHLYTSGPHGLSSCFLRI-RADGVVDCARGQSAHSLLEIKAVALR TVAIKGVHS-VRYLCMGADGKMQGLLQYSEEDCAFEEEILEDGYN-VYRSEKHRLPVSLSSAK QRQLYKNRGFLPLSHFLPMLPMVPEEPEDLRGHLES-DMFSSPLETDSMDPFGLVTGLEAVRS PSFEK (M50) (SEQ ID NO:50), or a subsequence or fragment thereof; or
RHPIPDSSPLLQFGGNVRLRHLYTSGPHGLSSCFLRI-RADGVVDCARGQSAHSLLEIKAVALR TVAIKGVHS-VRYLCMGADGKMQGLLQYSEEDCAFEEEIRPDGYN-VYRSEKHRLPVSLSSAK QRQLYKNRGFLPLSHFLPMLPMVPEEPEDLRGHLES-DMFSSPLETDSMDPFGLVTGLEAVRS PSFEK (M51) (SEQ ID NO:51), or a subsequence or fragment thereof; or
MDSSPLLQWGDPIRLRHLYTSGPHGLSSCFLRI-RADGVVDCARGQSAHSLLEIKAVALRTVA IKGVHS-VRYLCMGADGKMQGLLQYSEEDCAFEEEIRPDGYN-VYRSEKHRLPVSLSSAKQRQ LYKNRGFLPLSHFLPMLPMVPEEPEDLRGHLESDMF-SSPLETDSMDPFGLVTGLEAVRSPSFEK (M53) (SEQ ID NO:192), or a subsequence or fragment thereof; and
MRDSSPLVHYGWGDPIRLRHLYTSGPHGLSSCFLRI-RADGVVDCARGQSAHSLLEIKAVALR TVAIKGVHS-VRYLCMGADGKMQGLLQYSEEDCAFEEEIRPDGYN-VYRSEKHRLPVSLSSAK QRQLYKNRGFLPLSHFLPMLPMVPEEPEDLRGHLES-DMFSSPLETDSMDPFGLVTGLEAVRS PSFEK (M70) (SEQ ID NO:70), or a subsequence or fragment thereof, or for any of the foregoing peptide sequences the R terminal residue may be deleted.

Further particular non-limiting examples of peptide sequences include or consist of:
HPIPDSSPLLQFGGQVRLRHLYTSGPHGLSSCFLRI-RADGVVDCARGQSAHSLLEIKAVALRT VAIKGVHS-VRYLCMGADGKMQGLLQYSEEDCAFEEEIRPDGYN-VYRSEKHRLPVSLSSAKQ RQLYKNRGFLPLSHFLPMVPEEPEDLRGHLESD-MFSSPLETDSMDPFGLVTGLEAVRSP SFEK (SEQ ID NO:160), or a subsequence or fragment thereof; or
DSSPLLQFGGQVRLRHLYTSGPHGLSSCFLRIRADGV-VDCARGQSAHSLLEIKAVALRTVAI KGVHSVRYLCM-GADGKMQGLLQYSEEDCAFEEEIRPDGYN-VYRSEKHRLPVSLSSAKQRQ LYKNRGFLPLSHFLPMLPMVPEEPEDLRGHLESDMF-SSPLETDSMDPFGLVTGLEAVRSPSFEK (SEQ ID NO:161), or a subsequence or fragment thereof;
RPLAFSDASPHVHYGWGDPIRLRHLYTSGPHGLSSC-FLRIRADGVVDCARGQSAHSLLEIKA VALRTVAIK-GVHSVRYLCMGADGKMQGLLQYSEEDCAFEEEIRP-DGYNVYRSEKHRLPVSL SSAKQRQLYKNRGFLPLSHFLPMLPMVPEEPEDL-RGHLESDMFSSPLETDSMDPFGLVTGLE AVRSPSFEK (SEQ ID NO:1), or a subsequence or fragment thereof;
RPLAFSDSSPLVHYGWGDPIRLRHLYTSGPHGLSSC-FLRIRADGVVDCARGQSAHSLLEIKAV ALRTVAIK-GVHSVRYLCMGADGKMQGLLQYSEEDCAFEEEIRP-DGYNVYRSEKHRLPVSLS SAKQRQLYKNRGFLPLSHFLPMLPMVPEEPEDL-RGHLESDMFSSPLETDSMDPFGLVTGLEA VRSPSFEK (SEQ ID NO:2), or a subsequence or fragment thereof;
DSSPLVHYGWGDPIRLRHLYTSGPHGLSSCFLRI-RADGVVDCARGQSAHSLLEIKAVALRTV AIKGVHS-VRYLCMGADGKMQGLLQYSEEDCAFEEEIRPDGYN-VYRSEKHRLPVSLSSAKQR QLYKNRGFLPLSHFLPMLPMVPEEPEDLRGHLESD-MFSSPLETDSMDPFGLVTGLEAVRSPSFEK (SEQ ID NO:141), or a subsequence or fragment thereof.

Additional particular non-limiting examples of peptide sequences, having at the N-terminus, a peptide sequence including or consisting of all or a part of any of:

```
        (amino acids 1-25 of SEQ ID NO: 160)
HPIPDSSPLLQFGGQVRLRHLYTSG (M5-R);

(amino acids 2-22 of SEQ ID NO: 6)
DSSPLLQFGGQVRLRHLYTSG (M6-R);

(amino acids 1-27 of SEQ ID NO: 7)
RPLAFSDSSPLLQFGGQVRLRHLYTSG (M7);

(amino acids 2-26 of SEQ ID NO: 8)
HPIPDSSPLLQWGDPIRLRHLYTSG (M8-R);

(amino acids 2-28 of SEQ ID NO: 9)
HPIPDSSPLLQFGWGDPIRLRHLYTSG (M9-R);

(amino acids 2-28 of SEQ ID NO: 10)
HPIPDSSPHVHYGWGDPI RLRHLYTSG (M10-R);

(amino acids 1-27 of SEQ ID NO: 11)
RPLAFSDAGPLLQWGDPIRLRHLYTSG (M11);

(amino acids 1-29 of SEQ ID NO: 12)
RPLAFSDAGPLLQFGWGDPIRLRHLYTSG (M12);

(amino acids 1-27 of SEQ ID NO: 13)
RPLAFSDAGPLLQFGGQVRLRHLYTSG (M13);

(amino acids 2-26 of SEQ ID NO: 14)
HPIPDSSPHVHYGGQVRLRHLYTSG (M14-R);

(amino acids 1-27 of SEQ ID NO: 15)
RPLAFSDAGPHVHWGDPIRLRHLYTSG (M15);

(amino acids 1-27 of SEQ ID NO: 16)
RPLAFSDAGPHVHWGDPI RLRHLYTSG (M16);
```

-continued (amino acids 1-27 of SEQ ID NO: 17)
RPLAFSDAGPHVGWGDPI RLRHLYTSG (M17);

(amino acids 1-27 of SEQ ID NO: 18)
RPLAFSDAGPHYGWGDPIRLRHLYTSG (M18);

(amino acids 1-27 of SEQ ID NO: 19)
RPLAFSDAGPVYGWGDPIRLRHLYTSG (M19);

(amino acids 1-27 of SEQ ID NO: 20)
RPLAFSDAGPVHGWGDPI RLRHLYTSG (M20);

(amino acids 1-27 of SEQ ID NO: 21)
RPLAFSDAGPVHYWGDPIRLRHLYTSG (M21);

(amino acids 1-27 of SEQ ID NO: 22)
RPLAFSDAGPHVHGWGDPIRLRHLYTSG (M22);

(amino acids 1-27 of SEQ ID NO: 23)
RPLAFSDAGPHHGWGDPIRLRHLYTSG (M23);

(amino acids 1-27 of SEQ ID NO: 24)
RPLAFSDAGPHHYWGDPIRLRHLYTSG (M24);

(amino acids 1-27 of SEQ ID NO: 25)
RPLAFSDAGPHVYWGDPIRLRHLYTSG (M25);

(amino acids 1-27 of SEQ ID NO: 26)
RPLAFSDSSPLVHWGDPIRLRHLYTSG (M26);

(amino acids 1-27 of SEQ ID NO: 27)
RPLAFSDSSPHVHWGDPIRLRHLYTSG (M2722);

(amino acids 1-26 of SEQ ID NO: 28)
RPLAFSDAGPHVWGDPIRLRHLYTSG (M28);

(amino acids 1-28 of SEQ ID NO: 29)
RPLAFSDAGPHVHYWGDPI RLRHLYTSG (M29);

(amino acids 1-29 of SEQ ID NO: 30)
RPLAFSDAGPHVHYAWGDPIRLRHLYTSG (M30);

(amino acids 1-26 of SEQ ID NO: 31)
RHPIPDSSPLLQFGAQVRLRHLYTSG (M31);

(amino acids 1-26 of SEQ ID NO: 32)
RHPIPDSSPLLQFGDQVRLRHLYTSG (M32);

(amino acids 1-26 of SEQ ID NO: 33)
RHPIPDSSPLLQFGPQVRLRHLYTSG (M33);

(amino acids 1-26 of SEQ ID NO: 34)
RHPIPDSSPLLQFGGAVRLRHLYTSG (M34);

(amino acids 1-26 of SEQ ID NO: 35)
RHPIPDSSPLLQFGGEVRLRHLYTSG (M35);

(amino acids 1-26 of SEQ ID NO: 36)
RHPIPDSSPLLQFGGNVRLRHLYTSG (M36);

(amino acids 1-26 of SEQ ID NO: 37)
RHPIPDSSPLLQFGGQARLRHLYTSG (M37);

(amino acids 1-26 of SEQ ID NO: 38)
RHPIPDSSPLLQFGGQI RLRHLYTSG (M38);

(amino acids 1-26 of SEQ ID NO: 39)
RHPIPDSSPLLQFGGQTRLRHLYTSG (M39);

(amino acids 1-28 of SEQ ID NO: 40)
RHPIPDSSPLLQFGWGQPVRLRHLYTSG (M40);

(amino acids 2-24 of SEQ ID NO: 74)
DAGPHVYGWGDPIRLRHLYTSG (M74-R);

(amino acids 2-19 of SEQ ID NO: 75)
VHYGWGDPIRLRHLYTSG (M75-R);

(amino acids 2-10 of SEQ ID NO: 77)
RLRHLYTSG (M77-R);

-continued (amino acids 1-28 of SEQ ID NO: 9)
RHPIPDSSPLLQFGWGDPIRLRHLYTSG (M9);

(amino acids 1-26 of SEQ ID NO: 8)
RHPIPDSSPLLQWGDPIRLRHLYTSG (M8);

(amino acids 1-29 of SEQ ID NO: 12)
RPLAFSDAGPLLQFGWGDPI RLRHLYTSG (M12);

(amino acids 1-28 of SEQ ID NO: 10)
RHPIPDSSPHVHYGWGDPIRLRHLYTSG (M10);

(amino acids 1-27 of SEQ ID NO: 13)
RPLAFSDAGPLLQFGGQVRLRHLYTSG (M13);

(amino acids 1-26 of SEQ ID NO: 14)
RHPIPDSSPHVHYGGQVRLRHLYTSG (M14);

amino acids 1-27 of SEQ ID NO: 43)
RPLAFSDAGPHVHYGGDIRLRHLYTSG (M43);

(amino acids 1-22 of SEQ ID NO: 6)
RDSSPLLQFGGQVRLRHLYTSG (M6);

and for any of the foregoing peptide sequences the amino terminal R residue may be deleted.

Peptide sequences of the invention additionally include those with reduced or absent induction or formation of hepatocellular carcinoma (HCC) compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. Peptide sequences of the invention also include those with greater glucose lowering activity compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19. Peptide sequences of the invention moreover include those with less lipid (e.g., triglyceride, cholesterol, non-HDL or HDL) increasing activity compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19.

Typically, the number of amino acids or residues in an invention peptide sequence will total less than about 250 (e.g., amino acids or mimetics thereof). In various particular embodiments, the number of residues comprise from about 20 up to about 200 residues (e.g., amino acids or mimetics thereof). In additional embodiments, the number of residues comprise from about 50 up to about 200 residues (e.g., amino acids or mimetics thereof). In further embodiments, the number of residues comprise from about 100 up to about 195 residues (e.g., amino acids or mimetics thereof) in length.

Amino acids or residues can be linked by amide or by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, NY). Thus, when a peptide of the invention includes a portion of an FGF19 sequence and a portion of an FG21 sequence, the two portions need not be joined to each other by an amide bond, but can be joined by any other chemical moiety or conjugated together via a linker moiety.

The invention also includes subsequences, variants and modified forms of the exemplified peptide sequences (including the FGF19 and FGF21 variants and subsequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), so long as the foregoing retains at least a detectable or measureable activity or function. For example, certain exemplified variant peptides have FGF19 C-terminal sequence, PHGLSSCFLRIRADGVVD-CARGQSAHSLLEIKAVALRTVAIKGVHSVRYLCM-GADGKMQGL LQYSEEDCAFEEEIRPDGYN-VYRSEKHRLPVSLS SAKQRQLYKNRGFLPLSHFLPMLPMVPE EPEDL-RGHLESDMFSSPLETDSMDPFGLVTGLEAVRSPSFEK (SEQ ID NO:188) at the C-terminal portion, e.g., following the "TSG" amino acid residues of the variant.

Also, certain exemplified variant peptides, for example, those having all or a portion of FGF21 sequence at the amino-terminus, have an "R" residue positioned at the N-terminus, which can be omitted. Similarly, certain exemplified variant peptides, include an "M" residue positioned at the N-terminus, which can be appended to or further substituted for an omitted residue, such as an "R" residue. More particularly, in various embodiments peptide sequences at the N-terminus include any of: RDSS (SEQ ID NO:115), DSS, MDSS (SEQ ID NO:116) or MRDSS (SEQ ID NO:117). Furthermore, in cells when a "M" residue is adjacent to a "S" residue, the "M" residue may be cleaved such that the "M" residue is deleted from the peptide sequence, whereas when the "M" residue is adjacent to a "D" residue, the "M" residue may not be cleaved. Thus, by way of example, in various embodiments peptide sequences include those with the following residues at the N-terminus: MDSSPL (SEQ ID NO:119), MSDSSPL (SEQ ID NO:120) (cleaved to SDSSPL (SEQ ID NO:112)) and MSSPL (SEQ ID NO:113) (cleaved to SSPL (SEQ ID NO:114)).

Accordingly, the "peptide," "polypeptide," and "protein" sequences of the invention include subsequences, variants and modified forms of the FGF19 and FGF21 variants and subsequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), so long as the subsequence, variant or modified form (e.g., fusion or chimera) retains at least a detectable activity or function.

As used herein, the term "modify" and grammatical variations thereof, means that the composition deviates relative to a reference composition, such as a peptide sequence. Such modified peptide sequences, nucleic acids and other compositions may have greater or less activity or function, or have a distinct function or activity compared with a reference unmodified peptide sequence, nucleic acid, or other composition, or may have a property desirable in a protein formulated for therapy (e.g. serum half-life), to elicit antibody for use in a detection assay, and/or for protein purification. For example, a peptide sequence of the invention can be modified to increase serum half-life, to increase in vitro and/or in vivo stability of the protein, etc.

Particular examples of such subsequences, variants and modified forms of the peptide sequences exemplified herein (e.g., a peptide sequence listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) include substitutions, deletions and/or insertions/additions of one or more amino acids, to or from the amino terminus, the carboxy-terminus or internally. One example is a substitution of an amino acid residue for another amino acid residue within the peptide sequence. Another is a deletion of one or more amino acid residues from the peptide sequence, or an insertion or addition of one or more amino acid residues into the peptide sequence.

The number of residues substituted, deleted or inserted/added are one or more amino acids (e.g., 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more) of a peptide sequence. Thus, an FGF19 or FGF21 sequence can have few or many amino acids substituted, deleted or inserted/added (e.g., 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more). In addition, an FGF19 amino acid sequence can include or consist of an amino acid sequence of about 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more amino acids from FGF21; or an FGF21 amino acid or sequence can include or consist of an amino acid sequence of about 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250, or more amino acids from FGF19.

Specific examples of substitutions include substituting a D residue for an L-residue. Accordingly, although residues are listed in the L-isomer configuration D-amino acids at any particular or all positions of the peptide sequences of the invention are included, unless a D-isomer leads to a sequence that has no detectable or measurable function.

Additional specific examples are non-conservative and conservative substitutions. A "conservative substitution" is a replacement of one amino acid by a biologically, chemically or structurally similar residue. Biologically similar means that the substitution is compatible with a biological activity, e.g., glucose lowering activity. Structurally similar means that the amino acids have side chains with similar length, such as alanine, glycine and serine, or having similar size, or the structure of a first, second or additional peptide sequence is maintained. Chemical similarity means that the residues have the same charge or are both hydrophilic and hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc. Routine assays can be used to determine whether a subsequence, variant or modified form has activity, e.g., glucose lowering activity.

Particular examples of subsequences, variants and modified forms of the peptide sequences exemplified herein (e.g., a peptide sequence listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) have 50%-60%, 60%-70%, 70%-75%, 75%-80%, 80%-85%, 85%-90%, 90%-95%, or 96%, 97%, 98%, or 99% identity to a reference peptide sequence (for example, a peptide sequence in any of Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)). The term "identity" and "homology" and grammatical variations thereof mean that two or more referenced entities are the same. Thus, where two amino acid sequences are identical, they have the identical amino acid sequence. "Areas, regions or domains of identity" mean that a portion of two or more referenced entities are the same. Thus, where two amino acid sequences are identical or homologous over one or more sequence regions, they share identity in these regions.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For peptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

In the invention peptide sequences, including subsequences, variants and modified forms of the peptide sequences exemplified herein (e.g., sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) an "amino acid" or "residue" includes conventional alpha-amino acids as well as beta-amino acids, alpha, alpha disubstituted amino acids and N-substituted amino acids wherein at least one side chain is an amino acid side chain moiety as defined herein. An "amino acid" further includes N-alkyl alpha-amino acids, wherein the N-terminus amino group has a $C_1$ to $C_6$ linear or branched alkyl substituent. The term "amino acid" therefore includes stereoisomers and modifications of naturally occurring protein amino acids, non-protein amino acids, post-translationally modified amino acids (e.g., by glycosylation, phosphorylation, ester or amide cleavage, etc.), enzymatically modified or synthesized amino acids, derivatized amino acids, constructs or structures designed to mimic amino acids, amino acids with a side chain moiety modified, derivatized from naturally occurring moieties, or synthetic, or not naturally occurring, etc. Modified and unusual amino acids are included in the peptide sequences of the invention (see, for example, in *Synthetic Peptides: A User's Guide*; Hruby et al., *Biochem. J.* 268:249 (1990); and Toniolo C., *Int. J. Peptide Protein Res.* 35:287 (1990)).

In addition, protecting and modifying groups of amino acids are included. The term "amino acid side chain moiety" as used herein includes any side chain of any amino acid, as the term "amino acid" is defined herein. This therefore includes the side chain moiety in naturally occurring amino acids. It further includes side chain moieties in modified naturally occurring amino acids as set forth herein and known to one of skill in the art, such as side chain moieties in stereoisomers and modifications of naturally occurring protein amino acids, non-protein amino acids, post-translationally modified amino acids, enzymatically modified or synthesized amino acids, derivatized amino acids, constructs or structures designed to mimic amino acids, etc. For example, the side chain moiety of any amino acid disclosed herein or known to one of skill in the art is included within the definition.

A "derivative of an amino acid side chain moiety" is included within the definition of an amino acid side chain moiety. Non-limiting examples of derivatized amino acid side chain moieties include, for example: (a) adding one or more saturated or unsaturated carbon atoms to an existing alkyl, aryl, or aralkyl chain; (b) substituting a carbon in the side chain with another atom, preferably oxygen or nitrogen; (c) adding a terminal group to a carbon atom of the side chain, including methyl (—CH$_3$), methoxy (—OCH$_3$), nitro (—NO$_2$), hydroxyl (—OH), or cyano (—C≡N); (d) for side chain moieties including a hydroxy, thiol or amino groups, adding a suitable hydroxy, thiol or amino protecting group; or (e) for side chain moieties including a ring structure, adding one or more ring substituents, including hydroxyl, halogen, alkyl, or aryl groups attached directly or through an ether linkage. For amino groups, suitable protecting groups are known to the skilled artisan. Provided such derivatization provides a desired activity in the final peptide sequence (e.g., glucose lowering, improved glucose or lipid metabolism, anti-diabetic activity, absence of substantial HCC formation or tumorigenesis, absence of substantial modulation of lean or fat mass, etc.).

An "amino acid side chain moiety" includes all such derivatization, and particular non-limiting examples include: gamma-amino butyric acid, 12-amino dodecanoic acid, alpha-aminoisobutyric acid, 6-amino hexanoic acid, 4-(aminomethyl)-cyclohexane carboxylic acid, 8-amino octanoic acid, biphenylalanine, Boc—t-butoxycarbonyl, benzyl, benzoyl, citrulline, diaminobutyric acid, pyrrollysine, diaminopropionic acid, 3,3-diphenylalanine, orthonine, citrulline, 1,3-dihydro-2H-isoindolecarboxylic acid, ethyl, Fmoc—fluorenylmethoxycarbonyl, heptanoyl (CH3-(CH2).sub.5-C(═O)—), hexanoyl (CH3-(CH2)4-C(═O)—), homoarginine, homocysteine, homolysine, homophenylalanine, homoserine, methyl, methionine sulfoxide, methionine sulfone, norvaline (NVA), phenylglycine, propyl, isopropyl, sarcosine (SAR), tert-butylalanine, and benzyloxycarbonyl.

A single amino acid, including stereoisomers and modifications of naturally occurring protein amino acids, non-protein amino acids, post-translationally modified amino acids, enzymatically synthesized amino acids, non-naturally occurring amino acids including derivatized amino acids, an alpha, alpha disubstituted amino acid derived from any of the foregoing (i.e., an alpha, alpha disubstituted amino acid, wherein at least one side chain is the same as that of the residue from which it is derived), a beta-amino acid derived from any of the foregoing (i.e., a beta-amino acid which other than for the presence of a beta-carbon is otherwise the same as the residue from which it is derived) etc., including all of the foregoing can be referred to herein as a "residue." Suitable substituents, in addition to the side chain moiety of the alpha-amino acid, include C1 to C6 linear or branched alkyl. Aib is an example of an alpha, alpha disubstituted amino acid. While alpha, alpha disubstituted amino acids can be referred to using conventional L- and D-isomeric references, it is to be understood that such references are for convenience, and that where the substituents at the alpha-position are different, such amino acid can interchangeably be referred to as an alpha, alpha disubstituted amino acid derived from the L- or D-isomer, as appropriate, of a residue with the designated amino acid side chain moiety. Thus (S)-2-Amino-2-methyl-hexanoic acid can be referred to as either an alpha, alpha disubstituted amino acid derived from L-Nle (norleucine) or as an alpha, alpha disubstituted amino acid derived from D-Ala. Similarly, Aib can be referred to as an alpha, alpha disubstituted amino acid derived from Ala. Whenever an alpha, alpha disubstituted amino acid is provided, it is to be understood as including all (R) and (S) configurations thereof.

An "N-substituted amino acid" includes any amino acid wherein an amino acid side chain moiety is covalently bonded to the backbone amino group, optionally where there are no substituents other than H in the alpha-carbon position. Sarcosine is an example of an N-substituted amino acid. By way of example, sarcosine can be referred to as an N-substituted amino acid derivative of Ala, in that the amino acid side chain moiety of sarcosine and Ala is the same, i.e., methyl.

Covalent modifications of the invention peptide sequences, including subsequences, variants and modified forms of the peptide sequences exemplified herein (e.g., sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), are included in the invention. One type of covalent modification includes reacting targeted amino acid residues with an organic derivatizing agent that is capable of reacting with selected side chains or the N- or C-terminal residues of the peptide. Derivatization with bifunctional agents is useful, for instance, for cross linking peptide to a water-insoluble support matrix or surface for use in the method for purifying anti-peptide antibodies, and vice-versa. Commonly used cross linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, amidation of any C-terminal carboxyl group, etc.

Exemplified peptide sequences, and subsequences, variants and modified forms of the peptide sequences exemplified herein (e.g., sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), can also include alterations of the backbone for stability, derivatives, and peptidomimetics. The term "peptidomimetic" includes a molecule that is a mimic of a residue (referred to as a "mimetic"), including but not limited to piperazine core molecules, keto-piperazine core molecules and diazepine core molecules. Unless otherwise specified, an amino acid mimetic of an invention peptide sequence includes both a carboxyl group and amino group, and a group corresponding to an amino acid side chain, or in the case of a mimetic of Glycine, no side chain other than hydrogen.

By way of example, these would include compounds that mimic the sterics, surface charge distribution, polarity, etc. of a naturally occurring amino acid, but need not be an amino acid, which would impart stability in the biological system. For example, Proline may be substituted by other lactams or lactones of suitable size and substitution; Leucine may be substituted by an alkyl ketone, N-substituted amide, as well as variations in amino acid side chain length using alkyl, alkenyl or other substituents, others may be apparent to the skilled artisan. The essential element of making such substitutions is to provide a molecule of roughly the same size and charge and configuration as the residue used to design the molecule. Refinement of these modifications will be made by analyzing the compounds in a functional (e.g., glucose lowering) or other assay, and comparing the structure activity relationship. Such methods are within the scope of the skilled artisan working in medicinal chemistry and drug development.

Another type of modification of the invention peptide sequences, including subsequences, sequence variants and modified forms of the exemplified peptide sequences (including the peptides listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), is glycosylation. As used herein, "glycosylation" broadly refers to the presence, addition or attachment of one or more sugar (e.g., carbohydrate) moieties to proteins, lipids or other organic molecules. The use of the term "deglycosylation" herein is generally intended to mean the removal or deletion, of one or more sugar (e.g., carbohydrate) moieties. In addition, the phrase includes qualitative changes in the glycosylation of the native proteins involving a change in the type and proportions (amount) of the various sugar (e.g., carbohydrate) moieties present.

Glycosylation can be achieved by modification of an amino acid residue, or by adding one or more glycosylation sites that may or may not be present in the native sequence. For example, a typically non-glycosylated residue can be substituted for a residue that may be glycosylated. Addition of glycosylation sites can be accomplished by altering the amino acid sequence. The alteration to the peptide sequence may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein.

Peptide sequences of the invention may optionally be altered through changes at the nucleotide (e.g., DNA) level, particularly by mutating the DNA encoding the peptide at preselected bases such that codons are generated that will translate into the desired amino acids. Another means of increasing the number of carbohydrate moieties on the peptide is by chemical or enzymatic coupling of glycosides to the polypeptide (see, for example, in WO 87/05330). De-glycosylation can be accomplished by removing the underlying glycosylation site, by deleting the glycosylation by chemical and/or enzymatic means, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Various cell lines can be used to produce proteins that are glycosylated. One non-limiting example is Dihydrofolate reductase (DHFR)-deficient Chinese Hamster Ovary (CHO) cells, which are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

Another type of modification is to conjugate (e.g., link) one or more additional components or molecules at the N- and/or C-terminus of an invention peptide sequence, such as another protein (e.g., a protein having an amino acid sequence heterologous to the subject protein), or a carrier molecule. Thus, an exemplary peptide sequence can be a conjugate with another component or molecule.

In certain embodiments, the amino- or carboxy-terminus of an invention peptide sequence can be fused with an immunoglobulin Fc region (e.g., human Fc) to form a fusion conjugate (or fusion molecule). Fc fusion conjugates can increase the systemic half-life of biopharmaceuticals, and thus the biopharmaceutical product may have prolonged activity or require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. Well-known and validated Fc-fusion drugs consist of two copies of a biopharmaceutical linked to the Fc region of an antibody to improve pharmacokinetics, solubility, and production efficiency. More recent Fc-fusion technology links a single copy of a biopharmaceutical to Fc region of an antibody to optimize the pharmacokinetic and pharmacodynamic properties of the biopharmaceutical as compared to traditional Fc-fusion conjugates.

A conjugate modification can be used to produce a peptide sequence that retains activity with an additional or complementary function or activity of the second molecule. For example, a peptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated peptide sequence, a conjugate that targets a type of cell or organ more efficiently than an unconjugated peptide sequence, or a drug to further counter the causes or effects associated with a disorder or disease as set forth herein (e.g., diabetes).

Clinical effectiveness of protein therapeutics may be limited by short plasma half-life and susceptibility to degradation. Studies of various therapeutic proteins have shown that various modifications, including conjugating or linking the peptide sequence to any of a variety of nonproteinaceous polymers, e.g., polyethylene glycol (PEG), polypropylene glycol, or polyoxyalkylenes (see, for example, typically via a linking moiety covalently bound to both the protein and the nonproteinaceous polymer (e.g., a PEG) can prolong half-life. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGS suitable for conjugation to an invention peptide sequence is generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the peptide sequence can be linear or branched. Branched PEG derivatives, "star-PEGs" and multi-armed PEGS are included in the invention. A molecular weight of the PEG used in the invention is not restricted to any particular range, but certain embodiments have a molecular weight between 500 and 20,000 while other embodiments have a molecular weight between 4,000 and 10,000.

The invention includes compositions of conjugates wherein the PEGS have different "n" values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art.

PEG may directly or indirectly (e.g., through an intermediate) bind to the peptide sequences of the invention. For example, in one embodiment, PEG binds via a terminal reactive group (a "spacer"). The spacer, is, for example, a terminal reactive group which mediates a bond between the free amino or carboxyl groups of one or more of the peptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to free amino group is 2,4-bis(O-methoxypolyethyleneglycol)-6-chloro-s-triazine which may be prepared by reacting polyethylene glycol monomethyl ether with cyanuric chloride. The activated polyethylene glycol which is bound to the free carboxyl group includes polyoxyethylenediamine.

Conjugation of one or more of invention peptide sequences to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGS attached. Various methods known in the art may be used to terminate the reaction. In some embodiments the reaction is terminated by acidifying the reaction mixture and freezing at, e.g., −20° C.

Invention peptide sequences including subsequences, sequence variants and modified forms of the exemplified peptide sequences (including the peptides listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), further include conjugation to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells. Such conjugated forms, if desired, can be used to produce antibodies against peptide sequences of the invention.

Additional suitable components and molecules for conjugation include, for example, thyroglobulin; albumins such as human serum albumin (HSA); tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Fusion of albumin to an invention peptide sequence can, for example, be achieved by genetic manipulation, such that the DNA coding for HSA (human serum albumin), or a fragment thereof, is joined to the DNA coding for a peptide sequence. Thereafter, a suitable host can be transformed or transfected with the fused nucleotide sequence in the form of, for example, a suitable plasmid, so as to express a fusion polypeptide. The expression may be effected in vitro from, for example, prokaryotic or eukaryotic cells, or in vivo from, for example, a transgenic organism. In some embodiments of the invention, the expression of the fusion protein is performed in mammalian cell lines, for example, CHO cell lines.

Further means for genetically fusing target proteins or peptides to albumin include a technology known as Albufuse® (Novozymes Biopharma A/S; Denmark), and the conjugated therapeutic peptide sequences frequently become much more effective with better uptake in the body. The technology has been utilized commercially to produce Albuferon® (Human Genome Sciences), a combination of albumin and interferon α-2B used to treat hepatitis C infection.

Another embodiment entails the use of one or more human domain antibodies (dAbs). dAbs are the smallest functional binding units of human antibodies (IgGs) and have favorable stability and solubility characteristics. The technology entails a dAb(s) conjugated to HSA (thereby forming a "AlbudAb"; see, e.g., EP1517921B, WO2005/ 118642 and WO2006/051288) and a molecule of interest (e.g., a peptide sequence of the invention). AlbudAbs are often smaller and easier to manufacture in microbial expression systems, such as bacteria or yeast, than current technologies used for extending the serum half-life of peptides. As HSA has a half-life of about three weeks, the resulting conjugated molecule improves the half-life. Use of the dAb technology may also enhance the efficacy of the molecule of interest.

Additional suitable components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH~4, and then eluted with a linear (0M to 0.5M) NaCl gradient buffered at a pH from 3 to 5.5, preferably at pH~4.5. The content of the fractions obtained by cation exchange chromatography may be identified by molecular weight using conventional methods, for example, mass spectroscopy, SDS-PAGE, or other known methods for separating molecular entities by molecular weight. A fraction is then accordingly identified which contains the conjugate having the desired number of PEGS attached, purified free from unmodified protein sequences and from conjugates having other numbers of PEGs attached.

In still other embodiments, an invention peptide sequence is linked to a chemical agent (e.g., an immunotoxin or chemotherapeutic agent), including, but are not limited to, a cytotoxic agent, including taxol, cytochalasin B, gramicidin D, mitomycin, etoposide, tenoposide, vincristine, vinblastine, colchicin, doxorubicin, daunorubicin, and analogs or homologs thereof. Other chemical agents include, for example, antimetabolites (e.g., methotrexate, 6-mercaptopurine, 6-thioguanine, cytarabine, 5-fluorouracil decarbazine); alkylating agents (e.g., mechlorethamine, carmustine and lomustine, cyclothosphamide, busulfan, dibromomannitol, streptozotocin, mitomycin C, and cisplatin); antibiotics (e.g., bleomycin); and anti-mitotic agents (e.g., vincristine and vinblastine). Cytotoxins can be conjugated to a peptide of the invention using linker technology known in the art and described herein.

Further suitable components and molecules for conjugation include those suitable for detection in an assay. Particular non-limiting examples include detectable labels, such as a radioisotope (e.g., $^{125}$I; $^{35}$S, $^{32}$P; $^{33}$P), an enzyme which generates a detectable product (e.g., luciferase, β-galactosidase, horse radish peroxidase and alkaline phosphatase), a fluorescent protein, a chromogenic protein, dye (e.g., fluorescein isothiocyanate); fluorescence emitting metals (e.g., $^{152}$Eu); chemiluminescent compounds (e.g., luminol and acridinium salts); bioluminescent compounds (e.g., luciferin); and fluorescent proteins. Indirect labels include labeled or detectable antibodies that bind to a peptide sequence, where the antibody may be detected.

In certain embodiments, a peptide sequence of the invention is conjugated to a radioactive isotope to generate a cytotoxic radiopharmaceutical (radioimmunoconjugates) useful as a diagnostic or therapeutic agent. Examples of such radioactive isotopes include, but are not limited to, iodine[13]

indium[111], yttrium[90] and lutetium[177]. Methods for preparing radioimmunoconjugates are known to the skilled artisan. Examples of radioimmunoconjugates that are commercially available include ibritumomab, tiuxetan, and tositumomab.

Other means and methods included in the invention for prolonging the circulation half-life, increasing stability, reducing clearance, or altering immunogenicity or allergenicity of a peptide sequence of the invention involves modification of the peptide sequence by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

Any of the foregoing components and molecules used to modify peptide sequences of the invention may optionally be conjugated via a linker. Suitable linkers include "flexible linkers" which are generally of sufficient length to permit some movement between the modified peptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1, 2, 3, 4, 5, 6, 7, 8, 9, 10, 10-20, 20-30, 30-50 amino acids (e.g., Gly).

Exemplary flexible linkers include glycine polymers (G)n, glycine-serine polymers (for example, (GS)n, GSGGSn (SEQ ID NO:129) and GGGSn (SEQ ID NO:130), where n is an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:131), GGSGG (SEQ ID NO:132), GSGSG (SEQ ID NO:133), GSGGG (SEQ ID NO:134), GGGSG (SEQ ID NO:189), and GSSSG (SEQ ID NO:135).

Peptide sequences of the invention, including the FGF19 and FGF21 variants and subsequences and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), as well as subsequences, sequence variants and modified forms of the sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively) have one or more activities as set forth herein. One example of an activity is glucose lowering activity. Another example of an activity is reduced stimulation or formation of hepatocellular carcinoma (HCC), for example, as compared to FGF19. An additional example of an activity is lower or reduced lipid (e.g., triglyceride, cholesterol, non-HDL) or HDL increasing activity, for example, as compared to FGF21. A further example of an activity is a lower or reduced lean muscle mass reducing activity, for example, as compared to FGF21. Yet another example of an activity is binding to fibroblast growth factor receptor-4 (FGFR4), or activating FGFR4, for example, peptide sequences that bind to FGFR4 with an affinity comparable to or greater than FGF19 binding affinity for FGFR4; and peptide sequences that activate FGFR4 to an extent or amount comparable to or greater than FGF19 activates FGFR4. Still further examples of activities include down-regulation or reduction of aldo-keto reductase gene expression, for example, compared to FGF19; up-regulation or increased Slc1a2 gene expression compared to FGF21.

More particularly, peptide sequences of the invention, including the FGF19 and FGF21 variants and subsequences and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), as well as subsequences, variants and modified forms of the sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively) include those with the following activities: peptide sequences having reduced hepatocellular carcinoma (HCC) formation compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; peptide sequences having greater glucose lowering activity compared to FGF19, or FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; peptide sequences having less lipid increasing activity (e.g., less triglyceride, cholesterol, non-HDL) or more HDL increasing activity compared to FGF19, or an FGF 19 variant sequence having any of GQV, GDI, WGPI (SEQ ID NO:171), WGDPV (SEQ ID NO:172), WGDI (SEQ ID NO:173), GDPI (SEQ ID NO:174), GPI, WGQPI (SEQ ID NO:175), WGAPI (SEQ ID NO:176), AGDPI (SEQ ID NO:177), WADPI (SEQ ID NO:178), WGDAI (SEQ ID NO:179), WGDPA (SEQ ID NO:180), WDPI (SEQ ID NO:181), WGDI (SEQ ID NO:182), WGDP (SEQ ID NO:183) or FGDPI (SEQ ID NO:184) substituted for the WGDPI (SEQ ID NO:170) sequence at amino acids 16-20 of FGF19; and peptide sequences having less lean mass reducing activity as compared to FGF21.

More particularly, peptide sequences of the invention, including the FGF19 and FGF21 variants and subsequences and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), as well as subsequences, variants and modified forms of the sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively) include those with the following activities: peptide sequences that bind to fibroblast growth factor receptor-4 (FGFR4), or activate FGFR4, such as peptide sequences that bind to FGFR4 with an affinity comparable to or greater than FGF19 binding affinity for FGFR4; peptide sequences that activate FGFR4 to an extent or amount comparable to or greater than FGF19 activates FGFR4; peptide sequences that down-regulate or reduce aldo-keto reductase gene expression, for example, compared to FGF19; and peptide sequences that up-regulate or increase solute carrier family 1, member 2 (Slc1a2) gene expression as compared to FGF21.

Activities such as, for example, hepatocellular carcinoma (HCC) formation or tumorigenesis, glucose lowering activity, lipid increasing activity, or lean mass reducing activity can be ascertained in an animal, such as a db/db mouse. Measurement of binding to FGFR4 or activation of FGFR4 can be ascertained by assays disclosed herein (see, for example, Example 1) or known to the skilled artisan.

The term "bind," or "binding," when used in reference to a peptide sequence, means that the peptide sequence interacts at the molecular level. Thus, a peptide sequence that binds to FGFR4 binds to all or a part of the FGFR4 sequence. Specific and selective binding can be distinguished from non-specific binding using assays known in the art (e.g., competition binding, immunoprecipitation, ELISA, flow cytometry, Western blotting).

Peptides and peptidomimetics can be produced and isolated using methods known in the art. Peptides can be synthesized, in whole or in part, using chemical methods (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge *Science* 269:202 (1995); Merrifield, *Methods Enzymol.* 289:3 (1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994)). Peptide sequence variations, derivatives, substitutions and modifications can also be made using methods such as oligonucleotide-mediated (site-directed) mutagenesis, alanine scanning, and PCR based mutagenesis. Site-directed mutagenesis (Carter et al., *Nucl. Acids Res.,* 13:4331 (1986); Zoller et al., *Nucl. Acids Res.* 10:6487 (1987)), cassette mutagenesis (Wells et al., *Gene* 34:315 (1985)), restriction selection mutagenesis (Wells et al., *Philos. Trans. R. Soc. London SerA* 317:415 (1986)) and other techniques can be performed on cloned DNA to produce invention peptide sequences, variants, fusions and chimeras, and variations, derivatives, substitutions and modifications thereof.

A "synthesized" or "manufactured" peptide sequence is a peptide made by any method involving manipulation by the hand of man. Such methods include but are not limited to the aforementioned, such as chemical synthesis, recombinant DNA technology, biochemical or enzymatic fragmentation of larger molecules, and combinations of the foregoing.

Peptide sequences of the invention including subsequences, sequence variants and modified forms of the exemplified peptide sequences (e.g., sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), can also be modified to form a chimeric molecule. In accordance with the invention, there are provided peptide sequences that include a heterologous domain. Such domains can be added to the amino-terminus or at the carboxyl-terminus of the peptide sequence. Heterologous domains can also be positioned within the peptide sequence, and/or alternatively flanked by FGF19 and/or FGF21 derived amino acid sequences.

The term "peptide" also includes dimers or multimers (oligomers) of peptides. In accordance with the invention, there are also provided dimers or multimers (oligomers) of the exemplified peptide sequences as well as subsequences, variants and modified forms of the exemplified peptide sequences (e.g., sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)).

The invention further provides nucleic acid molecules encoding peptide sequences of the invention, including subsequences, sequence variants and modified forms of the sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), and vectors that include nucleic acid that encodes the peptide. Accordingly, "nucleic acids" include those that encode the exemplified peptide sequences disclosed herein, as well as those encoding functional subsequences, sequence variants and modified forms of the exemplified peptide sequences, so long as the foregoing retain at least detectable or measureable activity or function. For example, a subsequence, a variant or modified form of an exemplified peptide sequence disclosed herein (e.g., a sequence listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) that retains some ability to lower or reduce glucose, provide normal glucose homeostasis, or reduce the histopathological conditions associated with chronic or acute hyperglycemia in vivo, etc.

Nucleic acid, which can also be referred to herein as a gene, polynucleotide, nucleotide sequence, primer, oligonucleotide or probe refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA and cDNA. RNA nucleic acid can be spliced or unspliced mRNA, rRNA, tRNA or antisense. Nucleic acids include naturally occurring, synthetic, as well as nucleotide analogues and derivatives.

As a result of the degeneracy of the genetic code, nucleic acid molecules include sequences degenerate with respect to nucleic acid molecules encoding the peptide sequences of the invention. Thus, degenerate nucleic acid sequences encoding peptide sequences, including subsequences, variants and modified forms of the peptide sequences exemplified herein (e.g., sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), are provided. The term "complementary," when used in reference to a nucleic acid sequence, means the referenced regions are 100% complementary, i.e., exhibit 100% base pairing with no mismatches.

Nucleic acid can be produced using any of a variety of known standard cloning and chemical synthesis methods, and can be altered intentionally by site-directed mutagenesis or other recombinant techniques known to one skilled in the art. Purity of polynucleotides can be determined through sequencing, gel electrophoresis, UV spectrometry.

Nucleic acids may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically, expression control elements are juxtaposed at the 5' or the 3' ends of the genes but can also be intronic.

Expression control elements include elements that activate transcription constitutively, that are inducible (i.e., require an external signal or stimuli for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" typically means a minimal sequence element sufficient to direct transcription.

Nucleic acids may be inserted into a plasmid for transformation into a host cell and for subsequent expression and/or genetic manipulation. A plasmid is a nucleic acid that can be stably propagated in a host cell; plasmids may optionally contain expression control elements in order to drive expression of the nucleic acid. For purposes of this invention, a vector is synonymous with a plasmid. Plasmids and vectors generally contain at least an origin of replication for propagation in a cell and a promoter. Plasmids and vectors may also include an expression control element for expression in a host cell, and are therefore useful for expression and/or genetic manipulation of nucleic acids encoding peptide sequences, expressing peptide sequences in host cells and organisms (e.g., a subject in need of treatment), or producing peptide sequences, for example.

As used herein, the term "transgene" means a polynucleotide that has been introduced into a cell or organism by artifice. For example, a cell having a transgene, the transgene has been introduced by genetic manipulation or "transformation" of the cell. A cell or progeny thereof into which the transgene has been introduced is referred to as a "transformed cell" or "transformant." Typically, the transgene is included in progeny of the transformant or becomes a part of the organism that develops from the cell. Transgenes may be inserted into the chromosomal DNA or maintained as a self-replicating plasmid, YAC, minichromosome, or the like.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a peptide sequence in appropriate host cells.

As methods and uses of the invention include in vivo delivery, expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054), CMV vectors (U.S. Pat. No. 5,561,063) and parvovirus, rotavirus, Norwalk virus and lentiviral vectors (see, e.g., U.S. Pat. No. 6,013,516). Vectors include those that deliver genes to cells of the intestinal tract, including the stem cells (Croyle et al., *Gene Ther.* 5:645 (1998); S. J. Henning, *Adv. Drug Deliv. Rev.* 17:341 (1997), U.S. Pat. Nos. 5,821,235 and 6,110,456). Many of these vectors have been approved for human studies.

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. *Methods in Enzymology,* 153:516 (1987), eds. Wu & Grossman; Bitter *Methods in Enzymology,* 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is co-transfected into a host cell with a first vector containing a nucleic acid encoding a peptide sequence. Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes that can be employed in tk–, hgprt– or aprt– cells, respectively. Additionally, antimetabolite resistance can be used as the basis of selection for dhfr, which confers resistance to methotrexate (O'Hare et al., *Proc. Natl. Acad. Sci. USA* 78:1527 (1981)); the gpt gene, which confers resistance to mycophenolic acid (Mulligan et al., *Proc. Natl. Acad. Sci. USA* 78:2072 (1981)); neomycin gene, which confers resistance to aminoglycoside G-418 (Colberre-Garapin et al., *J. Mol. Biol.* 150:1 (1981)); puromycin; and hygromycin gene, which confers resistance to hygromycin (Santerre et al., *Gene* 30:147 (1984)). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

In accordance with the invention, there are provided transformed cell(s) (in vitro, ex vivo and in vivo) and host cells that produce a variant or fusion of FGF19 and/or FGF21 as set forth herein, where expression of the variant or fusion of FGF19 and/or FGF21 is conferred by a nucleic acid encoding the variant or fusion of FGF19 and/or FGF21. Transformed and host cells that express invention peptide sequences typically include a nucleic acid that encodes the invention peptide sequence. In one embodiment, a transformed or host cell is a prokaryotic cell. In another embodiment, a transformed or host cell is a eukaryotic cell. In various aspects, the eukaryotic cell is a yeast or mammalian (e.g., human, primate, etc.) cell.

As used herein, a "transformed" or "host" cell is a cell into which a nucleic acid is introduced that can be propagated and/or transcribed for expression of an encoded peptide sequence. The term also includes any progeny or subclones of the host cell.

Transformed and host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for transient or stable propagation or expression.

For gene therapy uses and methods, a transformed cell can be in a subject. A cell in a subject can be transformed with a nucleic acid that encodes an invention peptide sequence as set forth herein in vivo. Alternatively, a cell can be transformed in vitro with a transgene or polynucleotide, and then transplanted into a tissue of subject in order to effect treatment. Alternatively, a primary cell isolate or an established cell line can be transformed with a transgene or polynucleotide that encodes a variant of FGF19 and/or FGF21 or a fusion/chimeric sequence (or variant) thereof, such as a chimeric peptide sequence including all or a portion of FGF19, or including all or a portion of FGF21, and then optionally transplanted into a tissue of a subject.

Non-limiting target cells for expression of peptide sequences, particularly for expression in vivo, include pancreas cells (islet cells), muscle cells, mucosal cells and endocrine cells. Such endocrine cells can provide inducible production (secretion) of a variant of FGF19 and/or FGF21, or a fusion/chimeric sequence (or variant) thereof, such as a chimeric peptide sequence including all or a portion of FGF19, or including all or a portion of FGF21. Additional cells to transform include stem cells or other multipotent or pluripotent cells, for example, progenitor cells that differentiate into the various pancreas cells (islet cells), muscle cells, mucosal cells and endocrine cells. Targeting stem cells provides longer term expression of peptide sequences of the invention.

As used herein, the term "cultured," when used in reference to a cell, means that the cell is grown in vitro. A particular example of such a cell is a cell isolated from a subject, and grown or adapted for growth in tissue culture. Another example is a cell genetically manipulated in vitro, and transplanted back into the same or a different subject.

The term "isolated," when used in reference to a cell, means a cell that is separated from its naturally occurring in vivo environment. "Cultured" and "isolated" cells may be manipulated by the hand of man, such as genetically transformed. These terms include any progeny of the cells, including progeny cells that may not be identical to the parental cell due to mutations that occur during cell division. The terms do not include an entire human being.

Nucleic acids encoding invention peptide sequences can be introduced for stable expression into cells of a whole organism. Such organisms including non-human transgenic animals are useful for studying the effect of peptide expression in a whole animal and therapeutic benefit. For example, as disclosed herein, production of a variant of FGF19 and/or FGF21 or a fusion/chimeric sequence (or variant) thereof, such as a chimeric peptide sequence including all or a portion of FGF19, or including all or a portion of FGF21 as set forth herein, in mice lowered glucose and is anti-diabetic.

Mice strains that develop or are susceptible to developing a particular disease (e.g., diabetes, degenerative disorders, cancer, etc.) are also useful for introducing therapeutic proteins as described herein in order to study the effect of therapeutic protein expression in the disease susceptible mouse. Transgenic and genetic animal models that are susceptible to particular disease or physiological conditions, such as streptozotocin (STZ)-induced diabetic (STZ) mice, are appropriate targets for expressing variants of FGF19 and/or FGF21, fusions/chimeric sequences (or variant) thereof, such as a chimeric peptide sequence including all or a portion of FGF19, or including all or a portion of FGF21, as set forth herein. Thus, in accordance with the invention, there are provided non-human transgenic animals that produce a variant of FGF19 and/or FGF21, or a fusion/chimeric sequence (or variant) thereof, such as a chimeric peptide sequence including all or a portion of FGF19, or including all or a portion of FGF21, the production of which is not naturally occurring in the animal which is conferred by a transgene present in somatic or germ cells of the animal.

The term "transgenic animal" refers to an animal whose somatic or germ line cells bear genetic information received, directly or indirectly, by deliberate genetic manipulation at the subcellular level, such as by microinjection or infection with recombinant virus. The term "transgenic" further includes cells or tissues (i.e., "transgenic cell," "transgenic tissue") obtained from a transgenic animal genetically manipulated as described herein. In the present context, a "transgenic animal" does not encompass animals produced by classical crossbreeding or in vitro fertilization, but rather denotes animals in which one or more cells receive a nucleic acid molecule. Invention transgenic animals can be either heterozygous or homozygous with respect to the transgene. Methods for producing transgenic animals, including mice, sheep, pigs and frogs, are well known in the art (see, e.g., U.S. Pat. Nos. 5,721,367, 5,695,977, 5,650,298, and 5,614,396) and, as such, are additionally included.

Peptide sequences, nucleic acids encoding peptide sequences, vectors and transformed host cells expressing peptide sequences include isolated and purified forms. The term "isolated," when used as a modifier of an invention composition, means that the composition is separated, substantially completely or at least in part, from one or more components in an environment. Generally, compositions that exist in nature, when isolated, are substantially free of one or more materials with which they normally associate within nature, for example, one or more protein, nucleic acid, lipid, carbohydrate or cell membrane. The term "isolated" does not exclude alternative physical forms of the composition, such as variants, modifications or derivatized forms, fusions and chimeras, multimers/oligomers, etc., or forms expressed in host cells. The term "isolated" also does not exclude forms (e.g., pharmaceutical compositions, combination compositions, etc.) in which there are combinations therein, any one of which is produced by the hand of man.

An "isolated" composition can also be "purified" when free of some, a substantial number of, or most or all of one or more other materials, such as a contaminant or an undesired substance or material. Peptide sequences of the invention are generally not known or believed to exist in nature. However, for a composition that does exist in nature, an isolated composition will generally be free of some, a substantial number of, or most or all other materials with which it typically associates with in nature. Thus, an isolated peptide sequence that also occurs in nature does not include polypeptides or polynucleotides present among millions of other sequences, such as proteins of a protein library or nucleic acids in a genomic or cDNA library, for example. A "purified" composition includes combinations with one or more other inactive or active molecules. For example, a peptide sequence of the invention combined with another drug or agent, such as a glucose lowering drug or therapeutic agent, for example.

As used herein, the term "recombinant," when used as a modifier of peptide sequences, nucleic acids encoding peptide sequences, etc., means that the compositions have been manipulated (i.e., engineered) in a fashion that generally does not occur in nature (e.g., in vitro). A particular example of a recombinant peptide would be where a peptide sequence of the invention is expressed by a cell transfected with a nucleic acid encoding the peptide sequence. A particular example of a recombinant nucleic acid would be where a nucleic acid (e.g., genomic or cDNA) encoding a peptide sequence cloned into a plasmid, with or without 5', 3' or intron regions that the gene is normally contiguous with in the genome of the organism. Another example of a recombinant peptide or nucleic acid is a hybrid or fusion sequence, such as a chimeric peptide sequence comprising a portion of FGF19 and a portion of FGF21.

In accordance with the invention, there are provided compositions and mixtures of invention peptide sequences, including subsequences, variants and modified forms of the exemplified peptide sequences (including the FGF19 and FGF21 variants and subsequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)). In one embodiment, a mixture includes one or more peptide sequences and a pharmaceutically acceptable carrier or excipient. In another embodiment, a mixture includes one or more peptide sequences and an adjunct drug or therapeutic agent, such as an anti-diabetic, or glucose lowering, drug or therapeutic agent. Examples of drugs and therapeutic agents are set forth hereafter. Combinations, such as one or more peptide sequences in a pharmaceutically acceptable carrier or excipient, with one or more of an anti-diabetic, or glucose lowering drug or therapeutic agent are also provided. Such combinations of peptide sequence of the invention with another drug or agent, such as a glucose lowering drug or therapeutic agent, for example are useful in accordance with the invention methods and uses, for example, for treatment of a subject.

Combinations also include incorporation of peptide sequences or nucleic acids of the invention into particles or a polymeric substances, such as polyesters, carbohydrates, polyamine acids, hydrogel, polyvinyl pyrrolidone, ethylenevinylacetate, methylcellulose, carboxymethylcellulose, protamine sulfate, or lactide/glycolide copolymers, polylactide/glycolide copolymers, or ethylenevinylacetate copolymers; entrapment in microcapsules prepared by coacervation techniques or by interfacial polymerization, for example, by the use of hydroxymethylcellulose or gelatin-microcapsules, or poly (methylmethacrolate) microcapsules, respectively; incorporation in colloid drug delivery and dispersion systems such as macromolecule complexes, nano-capsules, microspheres, beads, and lipid-based systems (e.g., N-fatty acyl groups such as N-lauroyl, N-oleoyl, fatty amines such as dodecyl amine, oleoyl amine, etc., see U.S. Pat. No. 6,638,513), including oil-in-water emulsions, micelles, mixed micelles, and liposomes, for example.

Invention peptides including subsequences, variants and modified forms of the exemplified peptide sequences (including the FGF19 and FGF21 variants and subsequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) as set forth herein can be used to modulate glucose metabolism and facilitate transport of glucose from the blood to key metabolic organs such as muscle, liver and fat. Such peptide sequences can be produced in amounts sufficient or effective to restore glucose tolerance and/or to improve or provide normal glucose homeostasis.

As disclosed herein, administration of various FGF19 and/FGF21 variants and fusion peptide sequences to mice successfully reduced glucose levels. Furthermore, in contrast to FGF19, certain peptide sequences did not stimulate or induce HCC formation or tumorigenesis in mice. Thus, administration of invention peptides, including subsequences, variants and modified forms of the exemplified peptide sequences (including the FGF19 and FGF21 variants and subsequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), and the FGF19/FGF21 fusions and chimeras listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), into an animal, either by direct or indirect in vivo or by ex vivo methods (e.g., administering the variant or fusion peptide, a nucleic acid encoding the variant or fusion peptide, or a transformed cell or gene therapy vector expressing the variant or fusion peptide), can be used to treat various disorders.

Accordingly, the invention includes in vitro, ex vivo and in vivo (e.g., on or in a subject) methods and uses. Such methods and uses can be practiced with any of the peptide sequences of the invention set forth herein.

In accordance with the invention, there are provided methods of treating a subject having, or at risk of having, a disorder. In various embodiments, a method includes administering a peptide sequence, such as an FGF19 or FGF21 variant, fusion or chimera listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), or a subsequence, a variant or modified form of an FGF19 or FGF21 variant, fusion or chimera listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), to a subject in an amount effective for treating the disorder.

Exemplary disorders treatable, preventable, and the like with invention peptides, and methods and uses, include metabolic diseases and disorders. Non limiting examples of diseases and disorders include: 1. Glucose utilization disorders and the sequelae associated therewith, including diabetes mellitus (Type I and Type-2), gestational diabetes, hyperglycemia, insulin resistance, abnormal glucose metabolism, "pre-diabetes" (Impaired Fasting Glucose (IFG) or Impaired Glucose Tolerance (IGT)), and other physiological disorders associated with, or that result from, the hyperglycemic condition, including, for example, histopathological changes such as pancreatic β-cell destruction. For treatment, invention peptide sequences can be administered to subjects having a fasting plasma glucose (FPG) level greater than about 100 mg/dl. Peptide sequences of the invention may also be useful in other hyperglycemic-related disorders, including kidney damage (e.g., tubule damage or nephropathy), liver degeneration, eye damage (e.g., diabetic retinopathy or cataracts), and diabetic foot disorders; 2. Dyslipidemias and their sequelae such as, for example, atherosclerosis, coronary artery disease, cerebrovascular disorders and the like; 3. Other conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension, cardiovascular disease, stroke and heart failure; 4. Disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; 5. Disorders of cell cycle or cell differentiation processes such as adipose cell tumors, lipomatous carcinomas including, for example, liposarcomas, solid tumors, and neoplasms; 6. Neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; 7. Skin and dermatological disorders and/or disorders of wound healing processes, including erythematosquamous dermatoses; and 8. Other disorders such as syndrome X, osteoarthritis, and acute respiratory distress syndrome.

As used herein, the term "hyperglycemic" or "hyperglycemia," when used in reference to a condition of a subject means a transient or chronic abnormally high level of glucose present in the blood of a subject. The condition can be caused by a delay in glucose metabolism or absorption such that the subject exhibits glucose intolerance or a state of elevated glucose not typically found in normal subjects (e.g., in glucose-intolerant pre-diabetic subjects at risk of developing diabetes, or in diabetic subjects). Fasting plasma glucose (FPG) levels for normoglycemia are less than about 100 mg/dl, for impaired glucose metabolism, between about 100 and 126 mg/dl, and for diabetics greater than about 126 mg/dl.

As disclosed herein, the invention includes methods of preventing (e.g., in subjects predisposed to having a particular disorder(s)), delaying, slowing or inhibiting progression of, the onset of, or treating (e.g., ameliorating) obesity or an undesirable body mass (e.g., a greater than normal body mass index, or "BMI" relative to an appropriate matched subject of comparable age, gender, race, etc.). Thus, in various embodiments, a method of the invention for, for example, treating obesity or an undesirable body mass (including the co-morbid conditions of obesity, e.g., obstructive sleep apnea, arthritis, cancer (e.g., breast, endometrial, and colon), gallstones or hyperglycemia, includes contacting or administering a peptide of the invention as set forth herein (e.g., a variant or fusion of FGF19 and/or FGF21 as set forth in Tables 1-8 or SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), for example) in an amount effective to treat obesity or an undesirable body mass. In particular aspects, a subject has a body mass index greater than 25, for example, 25-30, 30-35, 35-40, or greater than 40.

Moreover, the invention includes methods of preventing (e.g., in subjects predisposed to having a particular disorder(s)), slowing or inhibiting the progression of, delaying the onset of, or treating undesirable levels or abnormally elevated serum/plasma LDL, VLDL, triglycerides or cholesterol, all of which, alone or in combination, can lead to, for example, plaque formation, narrowing or blockage of blood vessels, and increased risk of hypertension, stroke and coronary artery disease. Such disorders can be due to, for example, genetic predisposition or diet, for example.

The term "subject" refers to an animal. Typically, the animal is a mammal that would benefit from treatment with a peptide sequence of the invention. Particular examples include primates (e.g., humans), dogs, cats, horses, cows, pigs, and sheep.

Subjects include those having a disorder, e.g., a hyperglycemic disorder, such as diabetes, or subjects that do not have a disorder but may be at risk of developing the disorder, e.g., pre-diabetic subjects having FPG levels greater than 100 mg/dl, for example, between about 100 and 126 mg/dl. Subjects at risk of developing a disorder include, for example, those whose diet may contribute to development of acute or chronic hyperglycemia (e.g., diabetes), undesirable body mass or obesity, as well as those which may have a family history or genetic predisposition towards development of acute or chronic hyperglycemia, or undesirable body mass or obesity.

As disclosed herein, treatment methods include contacting or administering a peptide of the invention as set forth herein (e.g., a variant or fusion of FGF19 and or FGF21 as set forth in Tables 1-8 or SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively), for example) in an amount effective to achieve a desired outcome or result in a subject. A treatment that results in a desired outcome or result includes decreasing, reducing or preventing severity or frequency of one or more symptoms of the condition in the subject, e.g., an improvement in the subject's condition or a "beneficial effect" or "therapeutic effect." Therefore, treatment can decrease or reduce or prevent the severity or frequency of one or more symptoms of the disorder, stabilize or inhibit progression or worsening of the disorder, and in some instances, reverse the disorder, transiently (e.g., for 1-6, 6-12, or 12-24 hours), for medium term (e.g., 1-6, 6-12, 12-24 or 24-48 days) or long term (e.g., for 1-6, 6-12, 12-24, 24-48 weeks, or greater than 24-48 weeks). Thus, in the case of a hyperglycemic disorder, for example, treatment can lower or reduce blood glucose, improve glucose tolerance, improve glucose metabolism, provide normal glucose homeostasis, lower or reduce insulin resistance, lower or reduce insulin levels, or decrease, prevent, improve, or reverse metabolic syndrome, or a histopathological change associated with or that results from the hyperglycemic disorder, such as diabetes.

For example, a peptide sequence, method or use can lower or reduce glucose in one or more subjects having FPG levels greater than 100 mg/dl, for example, between about 100 and 125 mg/dl, or greater than 125 mg/dl, by 5-10%, 10-20%, 20-30%, or 30-50%, or more, or for example from greater than 200 mg/dl to less than 200 mg/dl, for greater than 150 mg/dl to less than 150 mg/dl, from greater than 125 mg/dl to less than 125 mg/dl, etc. In addition, a peptide sequence, method or use can lower or reduce glucose, for example, for pre-diabetes or for diabetes (e.g., Type 2) subjects with baseline HbAIc levels greater than about 5%, 6%, 7%, 8%, 9% or 10%, in particular 5%, 6%, or 7%.

Non-limiting examples of an improvement of a histopathological change associated with a hyperglycemic condition include, for example, decreasing, inhibiting, reducing or arresting: the destruction or degeneration of pancreas cells (e.g., β-cells), kidney damage such as tubule calcification or nephropathy, degeneration of liver, eye damage (e.g., diabetic retinopathy, cataracts), diabetic foot, ulcerations in mucosa such as mouth and gums, periodontitis, excess bleeding, slow or delayed healing of injuries or wounds (e.g., that lead to diabetic carbuncles), skin infections and other cutaneous disorders, cardiovascular and coronary heart disease, peripheral vascular disease, stroke, dyslipidemia, hypertension, obesity, or the risk of developing any of the foregoing. Improvement in undesirable body mass or obesity can include, for example, a reduction of body mass (as reflected by BMI or the like) or an improvement in an associated disorder, such as a decrease in triglyceride, cholesterol, LDL or VLDL levels, a decrease in blood pressure, a decrease in intimal thickening of the blood vessel, a decreased or reduced risk of cardiovascular disease, or stroke, decrease in resting heart rate, etc.

An "effective amount" or a "sufficient amount" for use and/or for treating a subject refer to an amount that provides, in single or multiple doses, alone, or in combination with one or more other compositions (therapeutic agents such as a drug or treatment for hyperglycemia), treatments, protocols, or therapeutic regimens agents, a detectable response of any duration of time (transient, medium or long term), a desired outcome in or an objective or subjective benefit to a subject of any measurable or detectable degree or for any duration of time (e.g., for hours, days, months, years, or cured). Such amounts typically are effective to ameliorate a disorder, or one, multiple or all adverse symptoms, consequences or complications of the disorder, to a measurable extent, although reducing or inhibiting a progression or worsening of the disorder, is considered a satisfactory outcome.

As used herein, the term "ameliorate" means an improvement in the subject's disorder, a reduction in the severity of the disorder, or an inhibition of progression or worsening of the disorder (e.g., stabilizing the disorder). In the case of a hyperglycemic disorder (e.g., diabetes, insulin resistance, glucose intolerance, metabolic syndrome, etc.), for example, an improvement can be a lowering or a reduction in blood glucose, a reduction in insulin resistance, a reduction in glucagon, an improvement in glucose tolerance, or glucose metabolism or homeostasis. An improvement in a hyperglycemic disorder also can include improved pancreatic function (e.g., inhibit or prevent β-cell/islet destruction or enhance β-cell number and/or function), a decrease in a pathology associated with or resulting from the disorder, such as an improvement in histopathology of an affected tissue or organ, as set forth herein. In the case of undesirable body mass or obesity, for example, an improvement can be a decrease in weight gain, a reduction of body mass (as reflected in reduced BMI, for example) or an improvement in a condition associated with undesirable body mass obesity, for example, as set forth herein (e.g., a lowering or a reduction of blood glucose, triglyceride, cholesterol, LDL or VLDL levels, a decrease in blood pressure, a decrease in intimal thickening of the blood vessel, etc.).

A therapeutic benefit or improvement therefore need not be complete ablation of any one, most or all symptoms, complications, consequences or underlying causes associated with the disorder or disease. Thus, a satisfactory endpoint is achieved when there is a transient, medium or long term, incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of the disorder or disease, over a duration of time (hours, days, weeks, months, etc.).

Thus, in the case of a disorder treatable by a peptide sequence of the invention, the amount of peptide sufficient to ameliorate a disorder will depend on the type, severity and extent, or duration of the disorder, the therapeutic effect or outcome desired, and can be readily ascertained by the skilled artisan. Appropriate amounts will also depend upon the individual subject (e.g., the bioavailability within the subject, gender, age, etc.). For example, a transient, or partial, restoration of normal glucose homeostasis in a subject can reduce the dosage amount or frequency of insulin injection, even though complete freedom from insulin has not resulted.

An effective amount can be ascertained, for example, by measuring one or more relevant physiological effects. In a particular non-limiting example in the case of a hyperglycemic condition, a lowering or reduction of blood glucose or an improvement in glucose tolerance test can be used to determine whether the amount of invention peptide sequence, including subsequences, sequence variants and modified forms of the exemplified peptide sequences (e.g., sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) is effective to treat a hyperglycemic condition. In another particular non-limiting example, an effective amount is an amount sufficient to reduce or decrease any level (e.g., a baseline level) of FPG, wherein, for example, an amount sufficient to reduce a FPG level greater than 200 mg/dl to less than 200 mg/dl, an amount sufficient to reduce a FPG level between 175 mg/dl and 200 mg/dl to less than the pre-administration level, an amount sufficient to reduce a FPG level between 150 mg/dl and 175 mg/dl to less than the pre-administration level, an amount sufficient to reduce a FPG level between 125 mg/dl and 150 mg/dl to less than the pre-administration level, and so on (e.g., reducing FPG levels to less than 125 mg/dl, to less than 120 mg/dl, to less than 115 mg/dl, to less than 110 mg/dl, etc.). In the case of HbAlc levels, an effective amount includes an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbAlc levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is an effective amount in accordance with the invention. In yet another particular non-limiting example in the case of undesirable body mass or obesity, an effective amount is an amount sufficient to decrease or reduce the body mass index (BMI) of a subject, a decrease or reduction of glucose, a decrease or reduction in serum/plasma levels of triglyceride, lipid, cholesterol, fatty acids, LDL and/or VLDL. In yet further particular non-limiting examples, an amount is an amount sufficient to decrease or reduce any of the aforementioned parameters by, for example, about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more.

Methods and uses of the invention for treating a subject are applicable for prophylaxis to prevent a disorder in a subject, such as a hyperglycemic disorder, or development of undesirable body mass or obesity. Alternatively, methods and uses can be practiced during or following treatment of a subject. For example, prior to, during or following treatment of a subject to lower glucose using insulin or another glucose lowering drug or therapeutic agent, for example, a method or use of the invention can, for example, a peptide sequence of the invention can be administered to the subject. In addition, a composition such as a peptide sequence of the invention can be combined with another drug or agent, such as a glucose lowering drug or therapeutic agent, for example.

Accordingly, methods and uses of the invention for treating a subject can be practiced prior to, substantially contemporaneously with or following another treatment, and can be supplemented with other forms of therapy. Supplementary therapies include other glucose lowering treatments, such as insulin, an insulin sensitivity enhancer and other drug treatments, a change in diet (low sugar, fats, etc.), weight loss surgery—(reducing stomach volume by gastric bypass, gastrectomy), gastric banding, gastric balloon, gastric sleeve, etc. For example, a method or use of the invention for treating a hyperglycemic or insulin resistance disorder can be used in combination with drugs or other pharmaceutical compositions that lower glucose or increase insulin sensitivity in a subject. Drugs for treating diabetes include, for example, biguanides and sulphonylureas (e.g., tolbutamide, chlorpropamide, acetohexamide, tolazamide, glibenclamide and glipizide), thiazolidinediones (rosiglitazone, pioglitazone), GLP-1 analogues, Dipeptidyl peptidase-4 (DPP-4) inhibitors, bromocriptine formulations (e.g. and bile acid sequestrants (e.g., colesevelam), and insulin (bolus and basal analogs), metformin (e.g., metformin hydrochloride) with or without a thiazolidinedione (TZD), and SGLT-2 inhibitors. Appetite suppression drugs are also well known and can be used in combination with the methods of the invention. Supplementary therapies can be administered prior to, contemporaneously with or following invention methods and uses.

Peptide sequences of the invention including subsequences, sequence variants and modified forms of the exemplified peptide sequences (sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), may be formulated in a unit dose or unit dosage form. In a particular embodiment, a peptide sequence is in an amount effective to treat a subject in need of treatment, e.g., due to hyperglycemia. Exemplary unit doses range from about 25-250, 250-500, 500-1000, 1000-2500 or 2500-5000, 5000-25,000, 25,000-50,000 ng; from about 25-250, 250-500, 500-1000, 1000-2500 or 2500-5000, 5000-25,000, 25,000-50,000 µg; and from about 25-250, 250-500, 500-1000, 1000-2500 or 2500-5000, 5000-25,000, 25,000-50,000 mg.

Peptide sequences of the invention including subsequences, sequence variants and modified forms of the exemplified peptide sequences (sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) can be administered to provide the intended effect as a single dose or multiple dosages, for example, in an effective or sufficient amount. Exemplary doses range from about 25-250, 250-500, 500-1000, 1000-2500 or 2500-5000, 5000-25,000, 25,000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 25,000-50,000 µg/kg. Single or multiple doses can be administered, for example, multiple times per day, on consecutive days, alternating days, weekly or intermittently (e.g., twice per week, once every 1, 2, 3, 4, 5, 6, 7 or 8 weeks, or once every 2, 3, 4, 5 or 6 months).

Peptide sequences of the invention including subsequences, variants and modified forms of the exemplified peptide sequences (sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) can be administered and methods may be practiced via systemic, regional or local administration, by any route. For example, a peptide sequence can be administered parenterally (e.g., subcutaneously, intravenously, intramuscularly, or intraperitoneally), orally (e.g., ingestion, buccal, or sublingual), inhalation, intradermally, intracavity, intracranially, transdermally (topical), transmucosally or rectally. Peptide sequences of the invention including subsequences, variants and modified forms of the exemplified peptide sequences (sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) and methods of the invention including pharmaceutical compositions can be administered via a (micro)encapsulated delivery system or packaged into an implant for administration.

The invention further provides "pharmaceutical compositions," which include a peptide sequence (or sequences) of the invention, including subsequences, variants and modified forms of the exemplified peptide sequences (sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)), and one or more pharmaceutically acceptable or physiologically acceptable diluent, carrier or excipient. In particular embodiments, a peptide sequence or sequences are present in a therapeutically acceptable amount. The pharmaceutical compositions may be used in accordance with the invention methods and uses. Thus, for example, the pharmaceutical compositions can be administered ex vivo or in vivo to a subject in order to practice treatment methods and uses of the invention.

Pharmaceutical compositions of the invention can be formulated to be compatible with the intended method or route of administration; exemplary routes of administration are set forth herein. In addition, the pharmaceutical compositions may further comprise other therapeutically active agents or compounds disclosed herein (e.g., glucose lowering agents) or known to the skilled artisan which can be used in the treatment or prevention of various diseases and disorders as set forth herein.

Pharmaceutical compositions typically comprise a therapeutically effective amount of at least one of the peptide sequences of the invention, including subsequences, variants and modified forms of the exemplified peptide sequences (sequences listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)) and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms used in the invention. Typical buffers include, but are not limited to pharmaceutically acceptable weak acids, weak bases, or mixtures thereof. Buffer components also include water soluble materials such as phosphoric acid, tartaric acids, lactic acid, succinic acid, citric acid, acetic acid, ascorbic acid, aspartic acid, glutamic acid, and salts thereof.

A primary solvent in a vehicle may be either aqueous or non-aqueous in nature. In addition, the vehicle may contain other pharmaceutically acceptable excipients for modifying or maintaining the pH, osmolarity, viscosity, sterility or stability of the pharmaceutical composition. In certain embodiments, the pharmaceutically acceptable vehicle is an aqueous buffer. In other embodiments, a vehicle comprises, for example, sodium chloride and/or sodium citrate.

Pharmaceutical compositions of the invention may contain still other pharmaceutically-acceptable formulation agents for modifying or maintaining the rate of release of an invention peptide. Such formulation agents include those substances known to artisans skilled in preparing sustained release formulations. For further reference pertaining to pharmaceutically and physiologically acceptable formulation agents, see, for example, *Remington's Pharmaceutical Sciences*, 18th Ed. (1990, Mack Publishing Co., Easton, Pa. 18042) pages 1435-1712, *The Merck Index*, 12th Ed. (1996, Merck Publishing Group, Whitehouse, N.J.); and *Pharmaceutical Principles of Solid Dosage Forms* (1993, Technonic Publishing Co., Inc., Lancaster, Pa.). Additional pharmaceutical compositions appropriate for administration are known in the art and are applicable in the methods and compositions of the invention.

A pharmaceutical composition may be stored in a sterile vial as a solution, suspension, gel, emulsion, solid, or dehydrated or lyophilized powder. Such compositions may be stored either in a ready to use form, a lyophilized form requiring reconstitution prior to use, a liquid form requiring dilution prior to use, or other acceptable form. In some embodiments, a pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver invention peptides, including implants (e.g., implantable pumps) and catheter systems, both of which are known to the skilled artisan. Depot injections, which are generally administered subcutaneously or intramuscularly, may also be utilized to release invention peptides over a defined period of time. Depot injections are usually either solid- or oil-based and generally comprise at least one of the formulation components set forth herein. The skilled artisan is familiar with possible formulations and uses of depot injections.

A pharmaceutical composition can be formulated to be compatible with its intended route of administration. Thus, pharmaceutical compositions include carriers, diluents, or excipients suitable for administration by routes including parenteral (e.g., subcutaneous (s.c.), intravenous, intramuscular, or intraperitoneal), intradermal, oral (e.g., ingestion), inhalation, intracavity, intracranial, and transdermal (topical).

Pharmaceutical compositions may be in the form of a sterile injectable aqueous or oleagenous suspension. This suspension may be formulated using suitable dispersing or wetting agents and suspending agents disclosed herein or known to the skilled artisan. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

Pharmaceutical compositions may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions. Such compositions may contain one or more agents such as sweetening agents, flavoring agents, coloring agents and preserving agents in order to provide pharmaceutically elegant and palatable preparations. Tablets containing an invention peptide may be in admixture with non-toxic pharmaceutically acceptable excipients suitable for the manufacture of tablets. These excipients include, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

Tablets, capsules and the like suitable for oral administration may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for preparation of such formulations are known to those skilled in the art and are commercially available.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by addition of water provide the active ingredient in admixture with a dispersing or wetting agent, suspending agent and one or more preservatives. Suitable dispersing or wetting agents and suspending agents are exemplified herein.

Pharmaceutical compositions of the invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Pharmaceutical compositions can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed. Prolonged absorption of injectable pharmaceutical compositions can be achieved by including an agent that delays absorption, for example, aluminum monostearate or gelatin. Prevention of the action of microorganisms can be achieved by various antibacterial and antifungal agents, for example, parabens, chlorobutanol, phenol, ascorbic acid, thimerosal, and the like.

The invention also includes invention peptides in the form of suppositories for rectal administration. The suppositories can be prepared by mixing an invention peptide with a suitable non-irritating excipient which is solid at ordinary temperatures but liquid at the rectal temperature and will therefore melt in the rectum to release the drug. Such materials include, but are not limited to, cocoa butter and polyethylene glycols.

In accordance with the invention, there are provided methods of identifying a peptide (or a subsequence, variant or modified form as set forth herein) having glucose lowering activity without substantial hepatocellular carcinoma (HCC) activity. In one embodiment, a method includes: screening (e.g., assaying or measuring) a peptide sequence (or a subsequence, variant or modified form as set forth herein) for glucose lowering activity; and screening (e.g., assaying or measuring) a peptide sequence (or a subsequence, variant or modified form as set forth herein) for HCC activity, or expression of a marker correlating with HCC activity. A peptide having glucose lowering activity and reduced or absent HCC activity thereby identifies the peptide. In particular aspects, the marker correlating with HCC activity comprises lipid profile—a peptide that has less lipid increasing activity compared to FGF19 indicates the peptide has reduced or absent HCC activity; or the marker correlating with HCC activity comprises aldo-keto reductase gene expression—a peptide that down-regulates or decreases aldo-keto reductase gene expression compared to FGF19 indicates that the peptide has reduced or absent HCC activity; or the marker indicative of HCC activity comprises Slc1a2 gene expression—a peptide that up-regulates or increases Slc1a2 gene expression compared to FGF19 indicates that the peptide has reduced or absent HCC activity.

The terms "assaying" and "measuring" and grammatical variations thereof are used interchangeably herein and refer to either qualitative or quantitative determinations, or both qualitative and quantitative determinations. When the terms are used in reference to detection, any means of assessing the relative amount is contemplated, including the various methods set forth herein and known in the art. For example, gene expression can be assayed or measured by a Northern blot, Western blot, immunoprecipitation assay, or by measuring activity, function or amount of the expressed protein (e.g., aldo-keto reductase or Slc1a2).

Risk factors for HCC, the most common type of liver cancer, include type 2 diabetes (probably exacerbated by obesity). The risk of HCC in type 2 diabetics is greater (from ~2.5 to ~7 times the non-diabetic risk) depending on the duration of diabetes and treatment protocol.

Various methodologies can be used in the screening and diagnosis of HCC and are well known to the skilled artisan. Indicators for HCC include detection of a tumor maker such as elevated alpha-fetoprotein (AFP) or des-gamma carboxyprothrombin (DCP) levels. A number of different scanning and imaging techniques are also helpful, including ultrasound, CT scans and MRI. In relation to the invention, evaluation of whether a peptide (e.g., a candidate peptide) exhibits evidence of inducing HCC may be determined in vivo by, for example, quantifying HCC nodule formation in an animal model, such as db/db mice, administered a peptide, compared to HCC nodule formation by wild type FGF19. Macroscopically, liver cancer may be nodular, where the tumor nodules (which are round-to-oval, grey or green, well circumscribed but not encapsulated) appear as either one large mass or multiple smaller masses. Alternatively, HCC may be present as an infiltrative tumor which is diffuse and poorly circumscribed and frequently infiltrates the portal veins.

Pathological assessment of hepatic tissue samples is generally performed after the results of one or more of the aforementioned techniques indicate the likely presence of HCC. Thus, methods of the invention may further include assessing a hepatic tissue sample from an in vivo animal model (e.g., a db/db mouse) useful in HCC studies in order to determine whether a peptide sequence exhibits evidence of inducing HCC. By microscopic assessment, a pathologist can determine whether one of the four general architectural and cytological types (patterns) of HCC are present (i.e., fibrolamellar, pseudoglandular (adenoid), pleomorphic (giant cell) and clear cell).

The invention also includes the generation and use of antibodies, and fragments thereof, that bind the peptide sequences of the invention, including subsequences, sequence variants and modified forms of the exemplified peptide sequences (including the peptides listed in Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)).

As used herein, the terms "antibodies" (Abs) and "immunoglobulins" (Igs) refer to glycoproteins having the same structural characteristics. While antibodies exhibit binding specificity to an antigen, immunoglobulins include both antibodies and other antibody-like molecules which may lack antigen specificity.

The term "antibody" includes intact monoclonal antibodies, polyclonal antibodies, multispecific antibodies (e.g., bispecific antibodies) formed from at least two intact antibodies, and antibody binding fragments including Fab and F(ab')$_2$, provided that they exhibit the desired biological activity. The basic antibody structural unit comprises a tetramer, and each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. In contrast, the carboxy-terminal portion of each chain defines a constant region primarily responsible for effector function. Human light chains are classified as kappa and lambda light chains, whereas human heavy chains are classified as mu, delta, gamma, alpha, or epsilon, and define the antibody's isotype as IgM, IgD, IgA, and IgE, respectively. Binding fragments are produced by recombinant DNA techniques, or by enzymatic or chemical cleavage of intact antibodies. Binding fragments include Fab, Fab', F(ab')$_2$, Fv, and single-chain antibodies.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Within light and heavy chains, the variable and constant regions are joined by a "J" region of about 12 or more amino acids, with the heavy chain also including a "D" region of about 10 more amino acids. The antibody chains all exhibit the same general structure of relatively conserved framework regions (FR) joined by three hyper-variable regions, also called complementarity-determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

An intact antibody has two binding sites and, except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab' fragments.

As used herein, the term "monoclonal antibody" refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. In contrast to polyclonal antibody preparations which include different antibodies directed against different determinants (epitopes), each monoclonal antibody is directed against a single determinant on the antigen.

A "neutralizing antibody" is an antibody molecule that is able to eliminate or significantly reduce an effector function of a target antigen to which it binds.

Antibody binding fragments may be produced by enzymatic or chemical cleavage of intact antibodies. Digestion of antibodies with the enzyme papain results in two identical antigen-binding fragments, also known as "Fab" fragments, and an "Fc" fragment which has no antigen-binding activity. Digestion of antibodies with the enzyme pepsin results in a F(ab')$_2$ fragment in which the two arms of the antibody molecule remain linked and comprise two-antigen binding sites. The F(ab')$_2$ fragment has the ability to crosslink antigen.

The term "Fab" refers to a fragment of an antibody that comprises the constant domain of the light chain and the CH1 domain of the heavy chain. The term "Fv" when used herein refers to the minimum fragment of an antibody that retains both antigen-recognition and antigen-binding sites. In a two-chain Fv species, this region consists of a dimer of one heavy-chain and one light-chain variable domain in non-covalent association. In a single-chain Fv species, one heavy-chain and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. While the six CDRs, collectively, confer antigen-binding specificity to the antibody, even a single variable domain (or half of an Fv comprising only three CDRs specific for an antigen) has the ability to recognize and bind antigen.

The term "complementarity determining regions" or "CDRs" refers to parts of immunological receptors that make contact with a specific ligand and determine its specificity. The term "hypervariable region" refers to the amino acid residues of an antibody which are responsible for antigen-binding. The hypervariable region generally comprises amino acid residues from a "complementarity determining region" or "CDR" and/or those residues from a "hypervariable loop".

As used herein, the term "epitope" refers to binding sites for antibodies on protein antigens. Epitopic determinants usually consist of chemically active surface groupings of molecules such as amino acids or sugar side chains, as well as specific three dimensional structural and charge characteristics. An antibody is said to bind an antigen when the dissociation constant is ≤1 µM, preferably ≤100 nM, and most preferably ≤10 nM. An increased equilibrium constant ("$K_D$") means that there is less affinity between the epitope and the antibody, whereas a decreased equilibrium constant means that there is a higher affinity between the epitope and the antibody. An antibody with a $K_D$ of "no more than" a certain amount means that the antibody will bind to the epitope with the given $K_D$ or more strongly. Whereas $K_D$ describes the binding characteristics of an epitope and an antibody, "potency" describes the effectiveness of the antibody itself for a function of the antibody. There is not necessarily a correlation between an equilibrium constant and potency; thus, for example, a relatively low $K_D$ does not automatically mean a high potency.

The term "selectively binds" in reference to an antibody does not mean that the antibody only binds to a single substance, but rather that the $K_D$ of the antibody to a first substance is less than the $K_D$ of the antibody to a second substance. An antibody that exclusively binds to an epitope only binds to that single epitope.

When administered to humans, antibodies that contain rodent (murine or rat) variable and/or constant regions are sometimes associated with, for example, rapid clearance from the body or the generation of an immune response by the body against the antibody. In order to avoid the utilization of rodent-derived antibodies, fully human antibodies can be generated through the introduction of human antibody function into a rodent so that the rodent produces fully human antibodies. Unless specifically identified herein, "human" and "fully human" antibodies can be used interchangeably herein. The term "fully human" can be useful when distinguishing antibodies that are only partially human from those that are completely, or fully human. The skilled artisan is aware of various methods of generating fully human antibodies.

In order to address possible human anti-mouse antibody responses, chimeric or otherwise humanized antibodies can be utilized. Chimeric antibodies have a human constant region and a murine variable region, and, as such, human anti-chimeric antibody responses may be observed in some patients. Therefore, it is advantageous to provide fully human antibodies against multimeric enzymes in order to avoid possible human anti-mouse antibody or human anti-chimeric antibody responses.

Fully human monoclonal antibodies can be prepared, for example, by the generation of hybridoma cell lines by techniques known to the skilled artisan. Other preparation methods involve the use of sequences encoding particular antibodies for transformation of a suitable mammalian host cell, such as a CHO cell. Transformation can be by any known method for introducing polynucleotides into a host cell, including, for example, packaging the polynucleotide in a virus (or into a viral vector) and transducing a host cell with the virus (or vector) or by transfection procedures known in the art. Methods for introducing heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Mammalian cell lines available as hosts for expression are well known in the art and include, but are not limited to CHO cells, HeLa cells, and human hepatocellular carcinoma cells.

Antibodies can be used diagnostically and/or therapeutically. For example, the antibodies can be used as a diagnostic by detecting the level of one or more peptides of the invention in a subject, and either comparing the detected level to standard control level or to a baseline level in a subject determined previously (e.g., prior to any illness). The antibodies can be used as a therapeutic to modulate the activity of one or more peptides of the invention, thereby having an effect on a condition or disorder.

The invention provides kits including, but not limited to, peptide sequences of the invention, optionally in combination with one or more therapeutic agents, compositions and pharmaceutical compositions thereof, packaged into suitable packaging material. A kit optionally includes a label or packaging insert including a description of the components or instructions for use in vitro, in vivo, or ex vivo, of the components therein. Exemplary instructions include instructions for reducing or lowering blood glucose, treatment of hyperglycemia, treatment of diabetes, etc.

A kit can contain a collection of such components, e.g., two or more peptide sequences alone, or a combination of a peptide sequence with another therapeutically useful composition (e.g., an anti-diabetic drug, such as a gastrin compound).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, separate or affixed to a component, a kit or packing material (e.g., a box), or attached to, for example, an ampule, tube or vial containing a kit component. Labels or inserts can additionally include a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include instructions for treatment or use of a peptide sequence as set forth herein. Kits of the invention therefore can additionally include labels or instructions for practicing any of the methods and uses of the invention described herein including treatment methods and uses.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain peptide sequences of the invention, or that contain nucleic acids encoding peptide sequences. The cells in the kit can be maintained under appropriate storage conditions until ready to use.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, GenBank citations and ATCC citations cited herein are incorporated by reference in their entirety. In case of conflict, the specification, including definitions, will control. As used herein, the singular forms "a", "and," and "the" include plural referents unless the context clearly indicates otherwise. Thus, for example, reference to "a peptide sequence" or a "treatment," includes a plurality of such sequences, treatments, and so forth.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1000, 1000-2500 or 2500-5000, 5000-25,000, 5000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |

| | | |
|---|---|---|
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

The following is a description of various methods and materials used in the studies herein.

Animals.

db/db mice were purchased from The Jackson Laboratory (Bar Harbor, Me.), Mice were kept in accordance with welfare guidelines under controlled light (12 hr light and 12 hr dark cycle, dark 6:30 pm-6:30 am), temperature (22±4° C.) and humidity (50%±20%) conditions. They had free access to water (autoclaved distilled water) and were fed ad libitum on a commercial diet (Harlan Laboratories, Indianapolis, Ind., Irradiated 2018 Teklad Global 18% Protein Rodent Diet) containing 17 kcal % fat, 23 kcal % protein and 60 kcal % carbohydrate. For diet-induced obesity, C57BL6/J mice (Jackson Laboratory) were maintained on a high-fat diet (D12492, Research Diet, New Brunswick, N.J. USA) containing 60 kcal % fat, 20 kcal % protein and 20 kcal % carbohydrate for 16-20 weeks. All animal studies were approved by the NGM Institutional Animal Care and Use Committee.

DNA and Amino Acid Sequences.

cDNA of ORF encoding human FGF19 (*Homo sapiens* FGF19, GenBank Accession No. NM_005117.2) variants Protein sequence encoded by the cDNA (GenBank Accession No. NP_005108.1)

PCR.

FGF19 ORF was amplified with polymerase chain reaction (PCR) using recombinant DNA (cDNA) prepared from human small intestinal tissue. PCR reagents kits with Phusion high-fidelity DNA polymerase were purchased from New England BioLabs (F-530L, Ipswich, Mass.). The following primers were used: forward PCR primer: 5' CCGACTAGTCACCatgcggagcgggtgtgtgg and reverse PCR primer: 5' ATAAGAATGCGGCCGCTTACTTCTCAAAGCTGGGACTCCTC.

Amplified DNA fragment was digested with restriction enzymes Spe I and Not I (the restriction sites were included in the 5' or 3' PCR primers, respectively) and was then ligated with AAV transgene vectors that had been digested with the same restriction enzymes. The vector used for expression contained a selectable marker and an expression cassette composed of a strong eukaryotic promoter 5' of a site for insertion of the cloned coding sequence, followed by a 3' untranslated region and bovine growth hormone polyadenylation tail. The expression construct is also flanked by internal terminal repeats at the 5' and 3' ends.

Production and Purification of AAV.

AAV293 cells (obtained from Agilent Technologies, Santa Clara, Calif.) were cultured in Dulbeco's Modification of Eagle's Medium (DMEM, Mediatech, Inc. Manassas, Va.) supplemented with 10% fetal bovine serum and 1× antibiotic-antimycotic solution (Mediatech, Inc. Manassas, Va.). The cells were plated at 50% density on day 1 in 150 mm cell culture plates and transfected on day 2, using calcium phosphate precipitation method with the following 3 plasmids (20 µg/plate of each): AAV transgene plasmid, pHelper plasmids (Agilent Technologies) and AAV2/9 plasmid (Gao et al., *J. Virol.* 78:6381 (2004)). 48 hours after transfection, the cells were scraped off the plates, pelleted by centrifugation at 3000×g and resuspended in buffer containing 20 mM Tris pH 8.5, 100 mM NaCl and 1 mM $MgCl_2$. The suspension was frozen in an alcohol dry ice bath and was then thawed in 37° C. water bath. The freeze and thaw cycles were repeated three times; Benzonase® (Sigma-aldrich, St. Louis, Mo.) was added to 50 units/ml; deoxycholate was added to a final concentration of 0.25%. After an incubation at 37° C. for 30 min, cell debris was pelleted by centrifugation at 5000×g for 20 min. Viral particles in the supernatant were purified using a discontinued iodixanal (Sigma-aldrich, St. Louis, Mo.) gradient as previously described (Zolotukhin S. et al (1999) *Gene Ther.* 6:973). The viral stock was concentrated using Vivaspin® 20 (MW cutoff 100,000 Dalton, Sartorius Stedim Biotech, Aubagne, France) and re-suspended in phosphate-buffered saline (PBS) with 10% glycerol and stored at −80° C. To determine the viral genome copy number, 2 µl of viral stock were incubated in 6 µl of solution containing 50 units/ml Benzonase®, 50 mM Tris-HCl pH 7.5, 10 mM $MgCl_2$ and 10 mM $CaCl_2$ at 37° C. for 30 minutes.

Afterwards, 15 µl of the solution containing 2 mg/ml of Proteinase K, 0.5% SDS and 25 mM EDTA were added and the mixture was incubated for additional 20 min at 55° C. to release viral DNA. Viral DNA was cleaned with mini DNeasy® Kit (Qiagen, Valencia, Calif.) and eluted with 40 µl of water. Viral genome copy (GC) was determined by using quantitative PCR.

Viral stock was diluted with PBS to desirable GC/ml. Viral working solution (200 µl) was delivered into mice via tail vein injection.

Blood Glucose Assay.

Blood glucose in mouse tail snip was measured using ACCU-CHEK Active test strips read by ACCU-CHEK Active meter (Roche Diagnostics, Indianapolis, Ind.) following manufacturer's instruction.

Lipid Profile Assay.

Whole blood from mouse tail snips was collected into plain capillary tubes (BD Clay Adams SurePrep™, Becton Dickenson and Co. Sparks, Md.). Serum and blood cells were separated by spinning the tubes in an Autocrit™ Ultra 3 (Becton Dickinson and Co. Sparks, Md.). Serum samples were assayed for lipid profile (triglyceride, total cholesterol, HDL, and non-HDL) using Integra™ 400 Clinical Analyzer (Roche Diagnostics, Indianapolis, Ind.) following the manufacturer's instructions.

Serum FGF19/FGF21/Variants Exposure Level Assay.

Whole blood (about 50 µl/mouse) from mouse tail snips was collected into plain capillary tubes (BD Clay Adams SurePrep, Becton Dickenson and Co. Sparks, Md.). Serum and blood cells were separated by spinning the tubes in an Autocrit™ Ultra 3 (Becton Dickinson and Co. Sparks, Md.). FGF19, FGF21, and variant exposure levels in serum were determined using EIA kits (Biovendor) by following the manufacturer's instructions.

Hepatocellular Carcinoma (HCC) Assay.

Liver specimen was harvested from db/db mice 6 months after AAV injection. HCC score is recorded as the number of HCC nodules on the surface of the entire liver from variants-injected mice divided by the number of HCC nodules from wildtype FGF19-injected mice.

Liver Gene Expression Assay.

Liver specimen was harvested and homogenized in TRIzol® reagent (Invitrogen). Total RNA was extracted following manufacturer's instruction. RNA was treated with DNase (Ambion) followed by quantitative RT-PCR analysis using TaqMan® primers and reagents from Applied Biosystems. Relative mRNA levels of aldo-keto reductase and slc1a2 in the liver was calculated using ΔΔCt method.

FGFR4 Binding and Activity Assays.

Solid phase ELISA (binding) and ERK phosphorylation assay were performed using purified recombinant proteins. FGFR binding assay was conducted using solid phase ELISA. Briefly, 96 well plate was coated with 2 ug/ml anti-hFc antibody and incubated with 1 ug/ml FGFR1-hFc or FGFR4-hFc. Binding to FGF19 variants in the presence of 1 ug/ml soluble b-klotho and 20 ug/ml heparin were detected by biotinylated anti-FGF19 antibodies (0.2 ug/mL), followed by streptavidin-HRP incubation (100 ng/mL). For FGFR4 activation assay, Hep3B cells were stimulated with FGF19 variants for 10 minutes at 37 C, then immediately lysed and assayed for ERK phosphorylation using a commercially available kit from Cis-Bio.

Example 2

The following is a description of studies showing the glucose lowering activity of various sequence variants of FGF19 and FGF21, and FGF19/FGF21 fusion constructs.

FIG. 1 illustrates exemplary FGF19/FGF21 fusion constructs, and the segments from each of FGF19 and FGF21 present in the fusion peptides. These peptides were analyzed for glucose lowering activity and statistically significant lipid elevating or increasing activity (Tables 1-8 and SEQ ID NOs: 1, 2, 3, 5, 48, 49, 50, 51, 52, 53, 69, 70, 71, 72 and 73 (M1, M2, M3, M5, M48, M49, M50, M51, M52, M53, M69, M70, M71, M72 and M73, respectively)).

Mice (db/db) were injected with viral vector expressing FGF19, FGF21 or variants, and analyzed after injection. Glucose-lowering activity of each sequence is represented by a "+" symbol (a "−" symbol means no glucose lowering activity, a "+/−" symbol means variants retain minimal glucose-lowering activity); lipid elevating activity is represented by a "+" symbol (a "−" symbol means no lipid elevating activity, a "+/−" symbol means variants retain minimal lipid-elevating activity, FIG. 1).

Figure 2B:
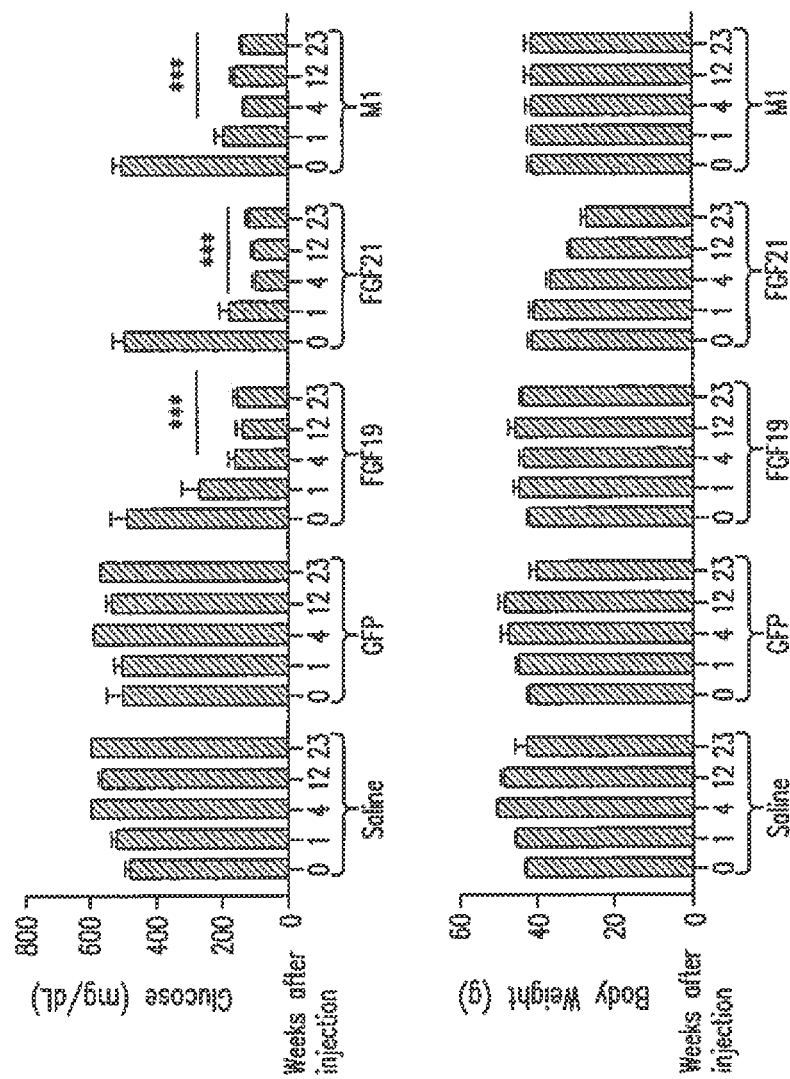
Figure 2C:
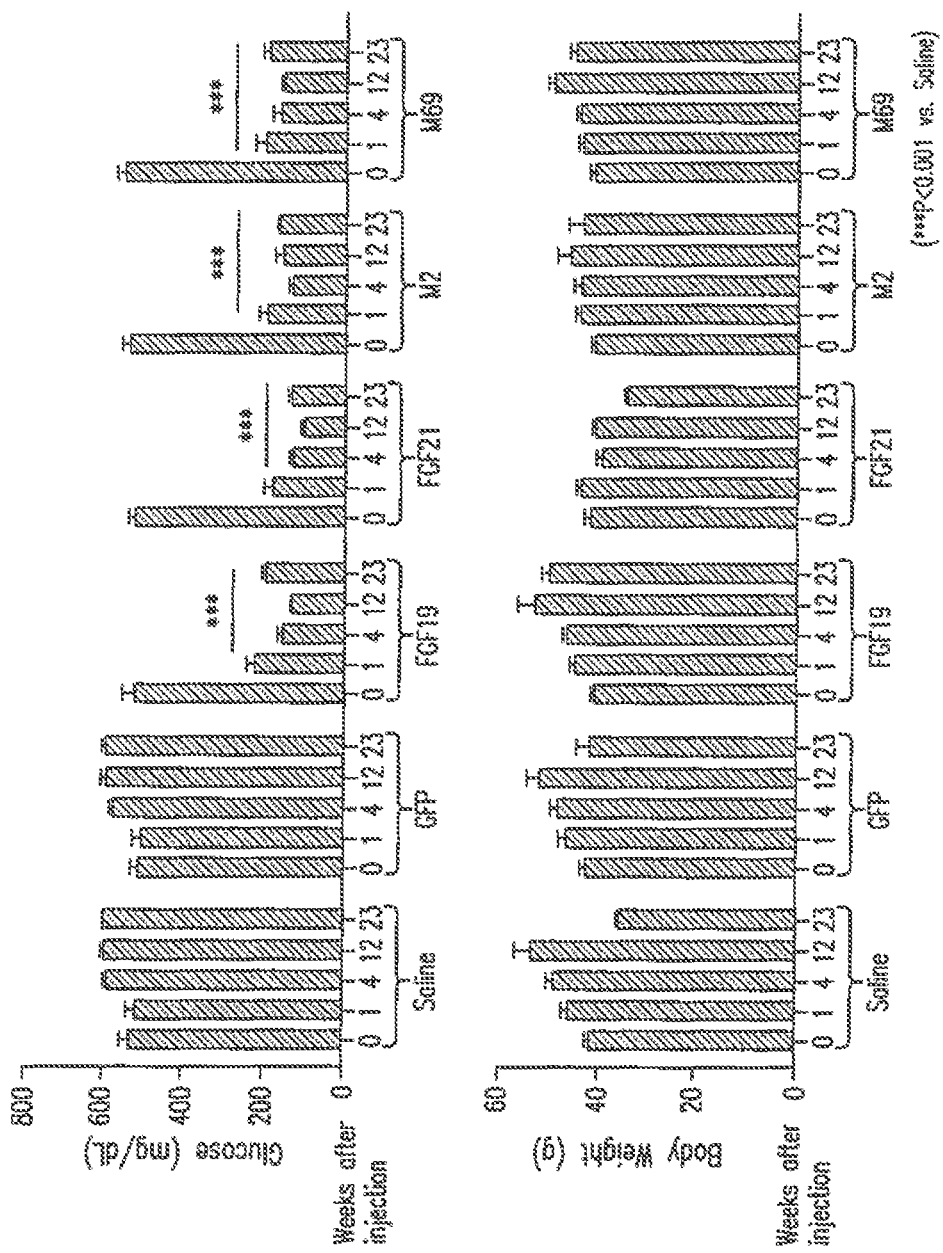
Figure 2D:
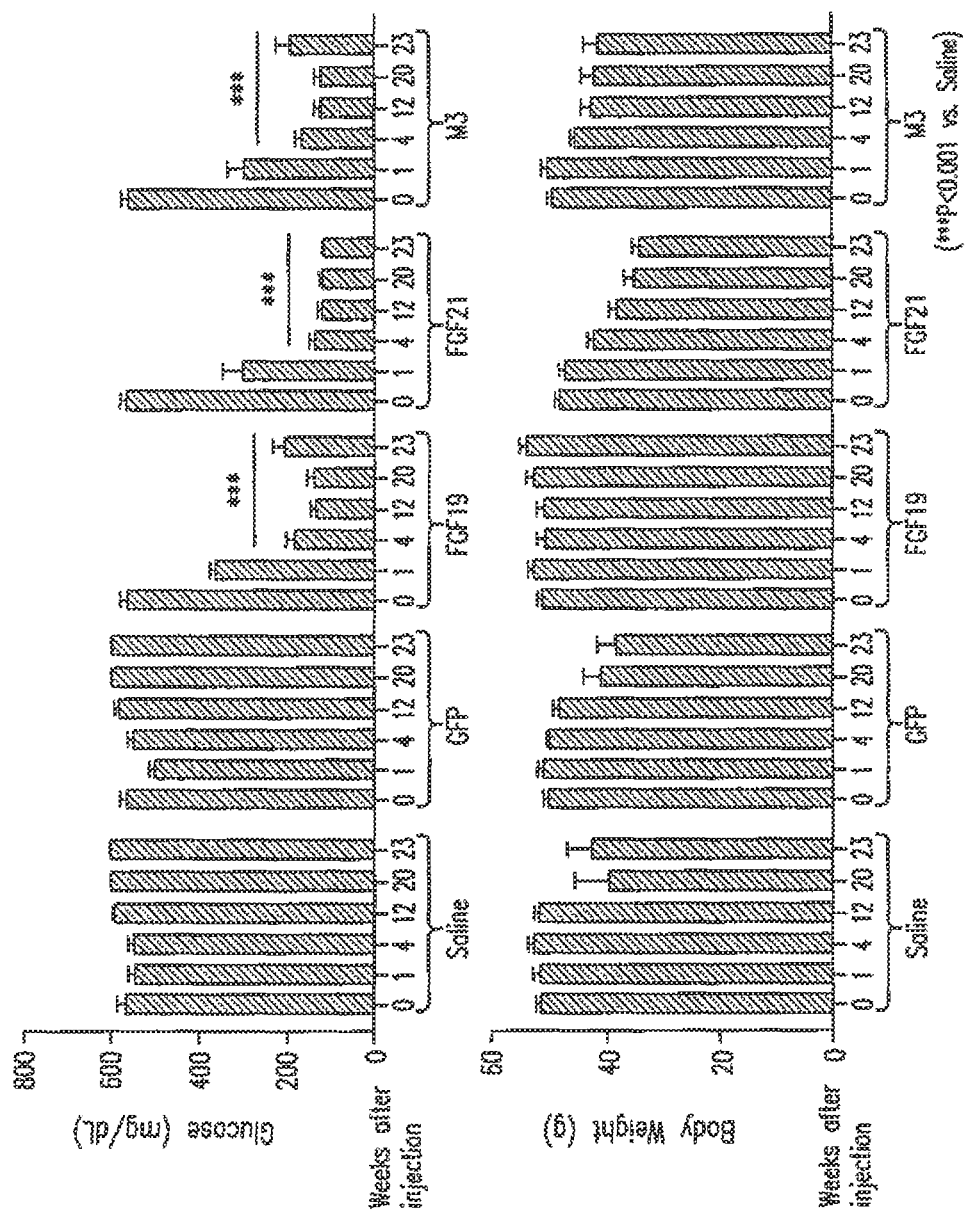
Figure 2E:
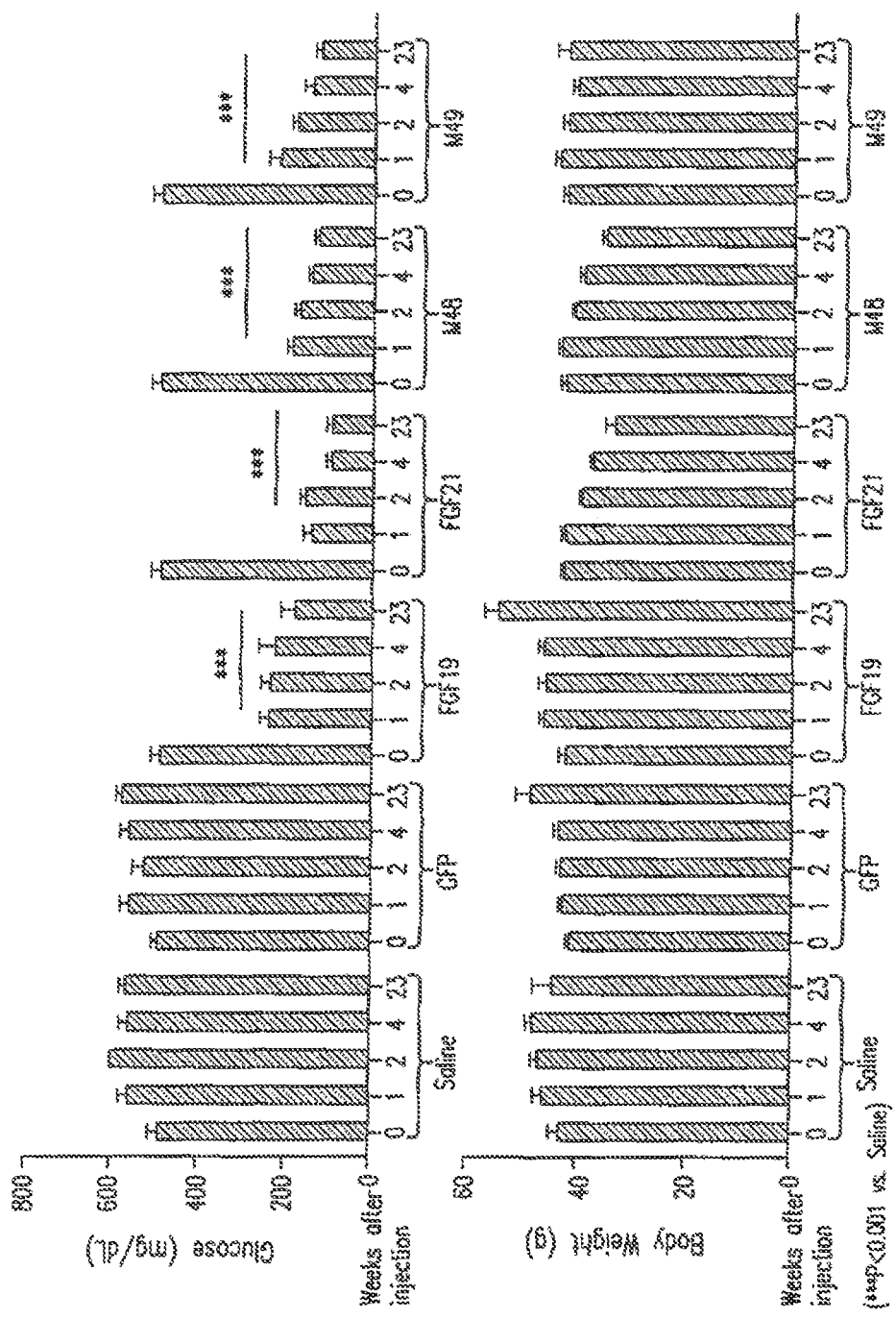
Figure 2F:
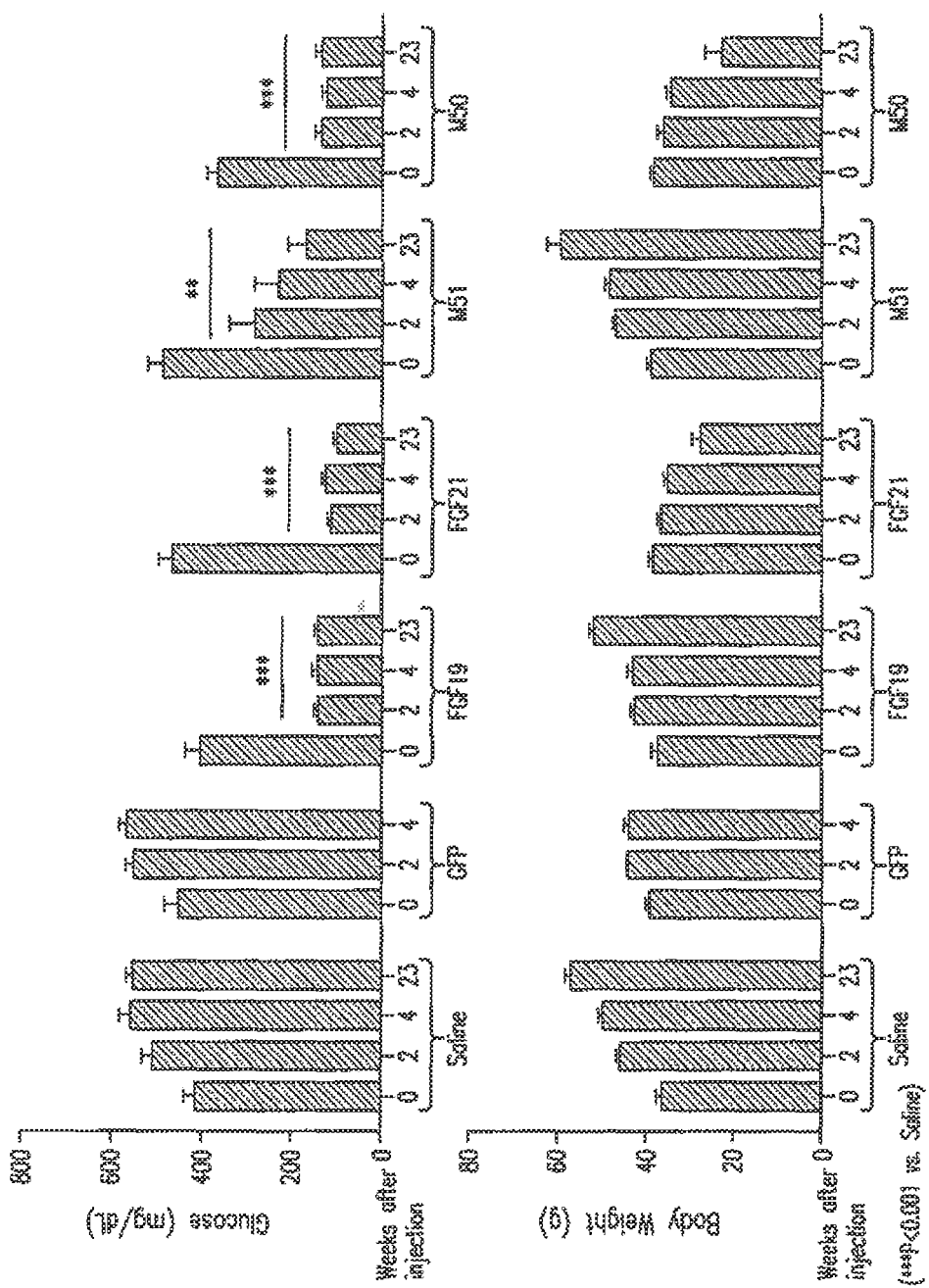
Figure 2G:
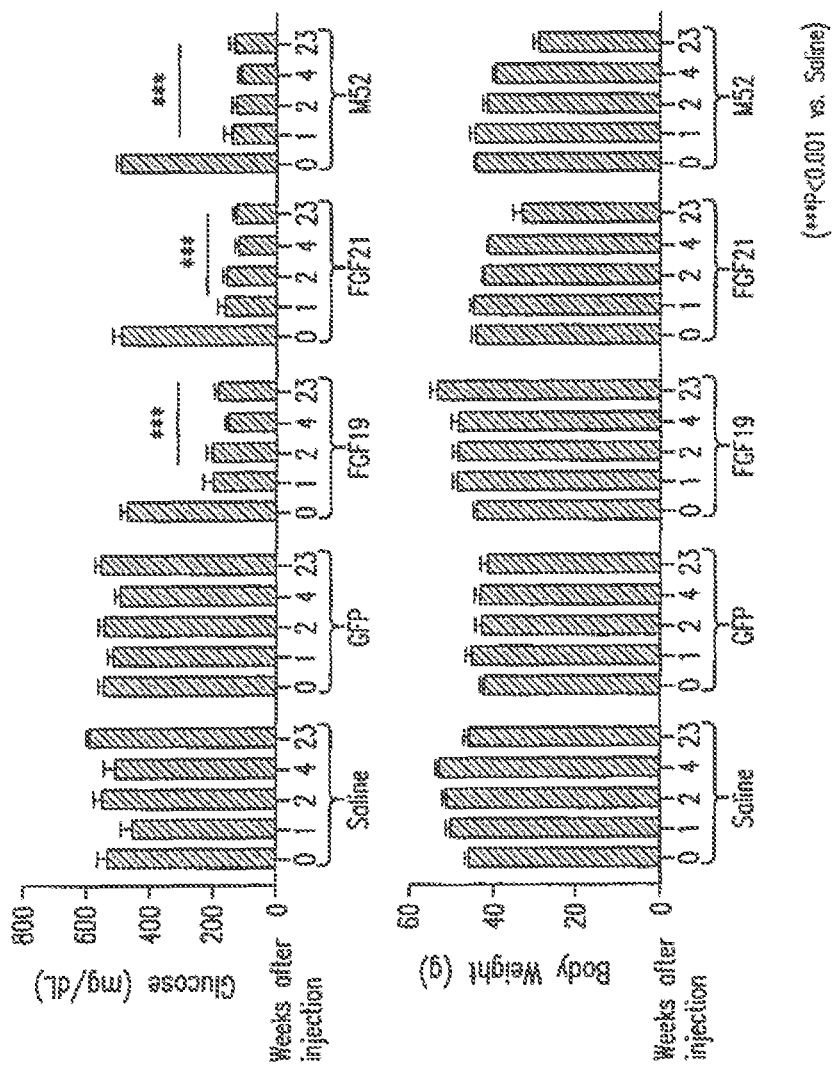
Figure 2H:
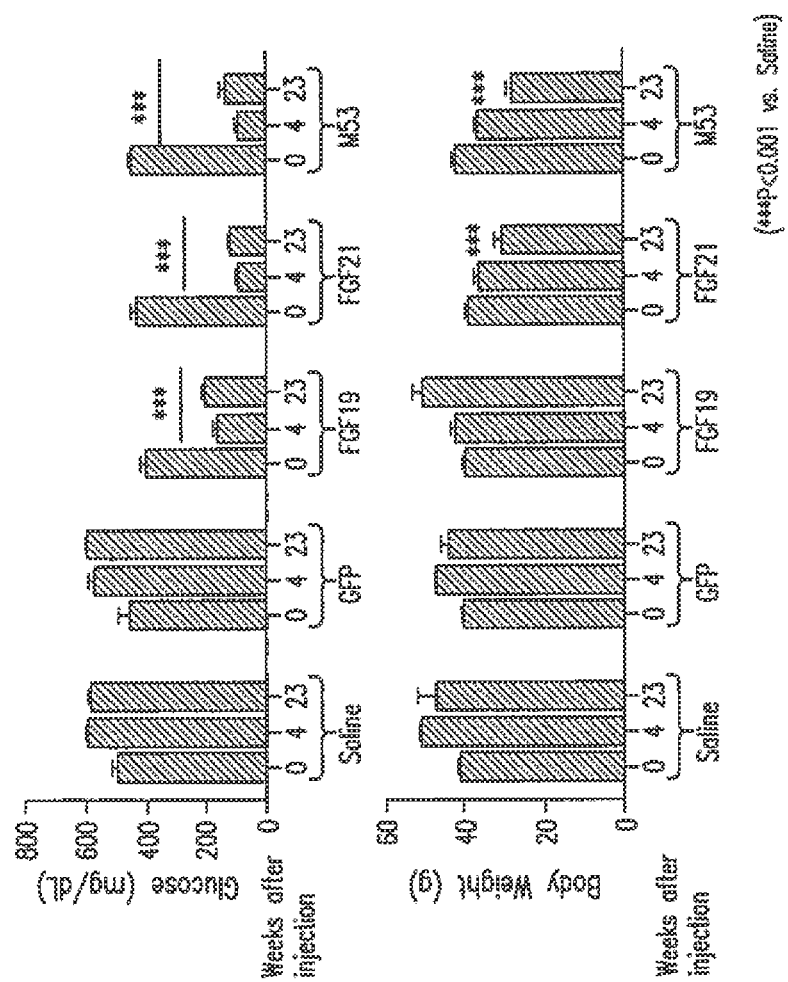
Figure 21:
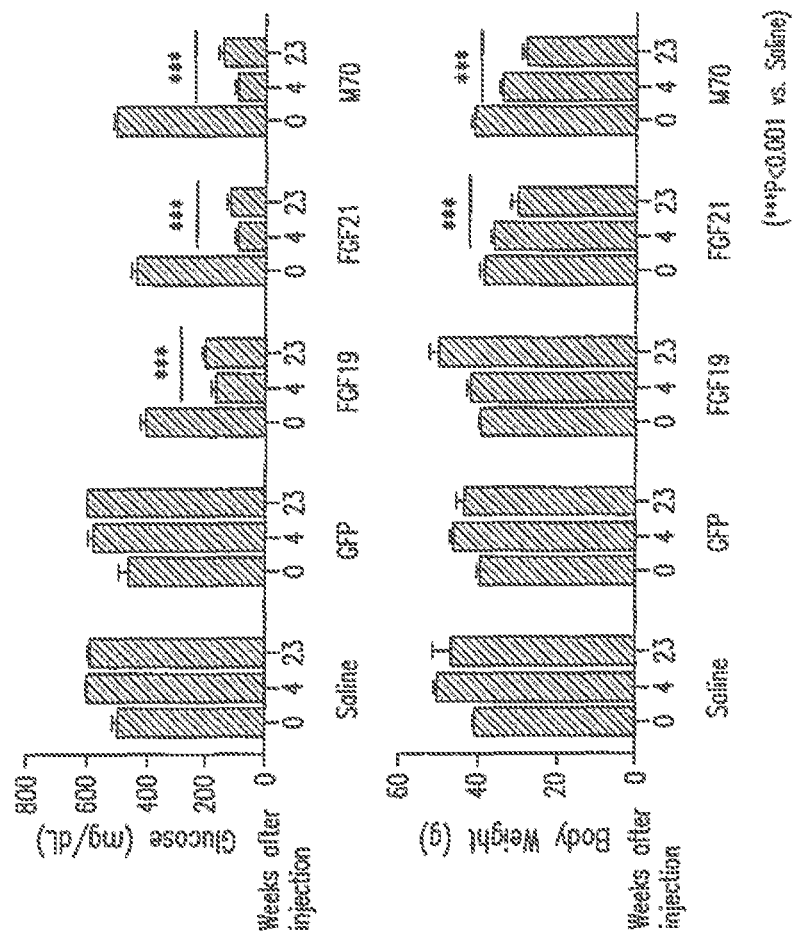
Figure 3A:
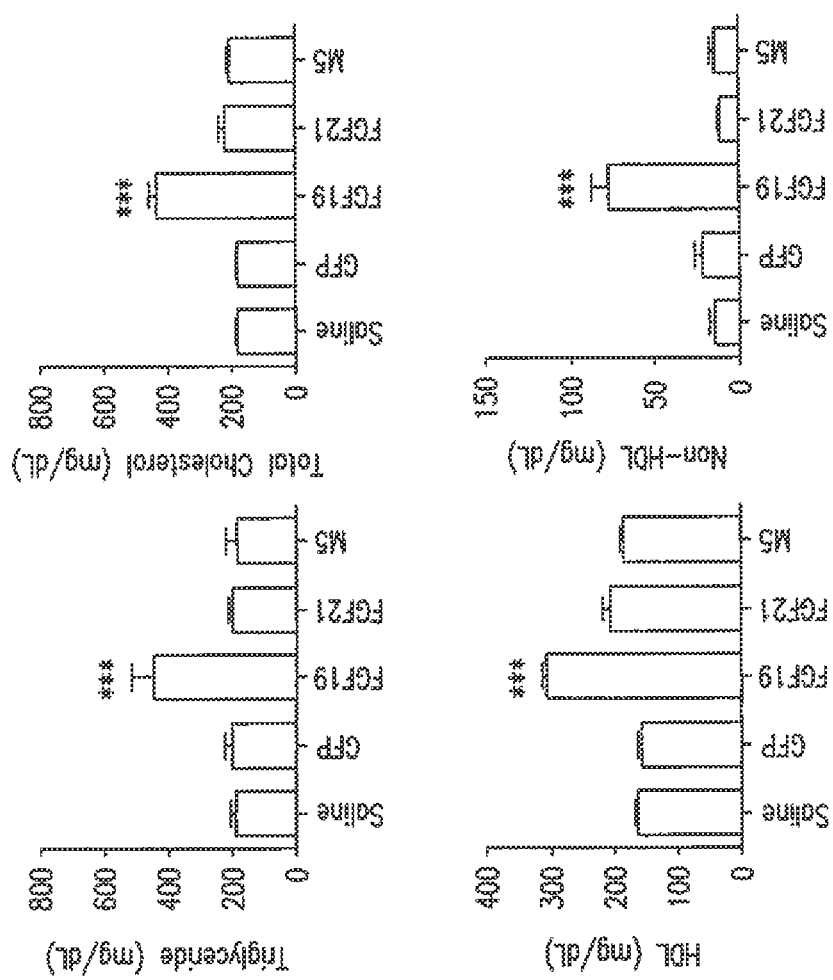
Figure 3B:
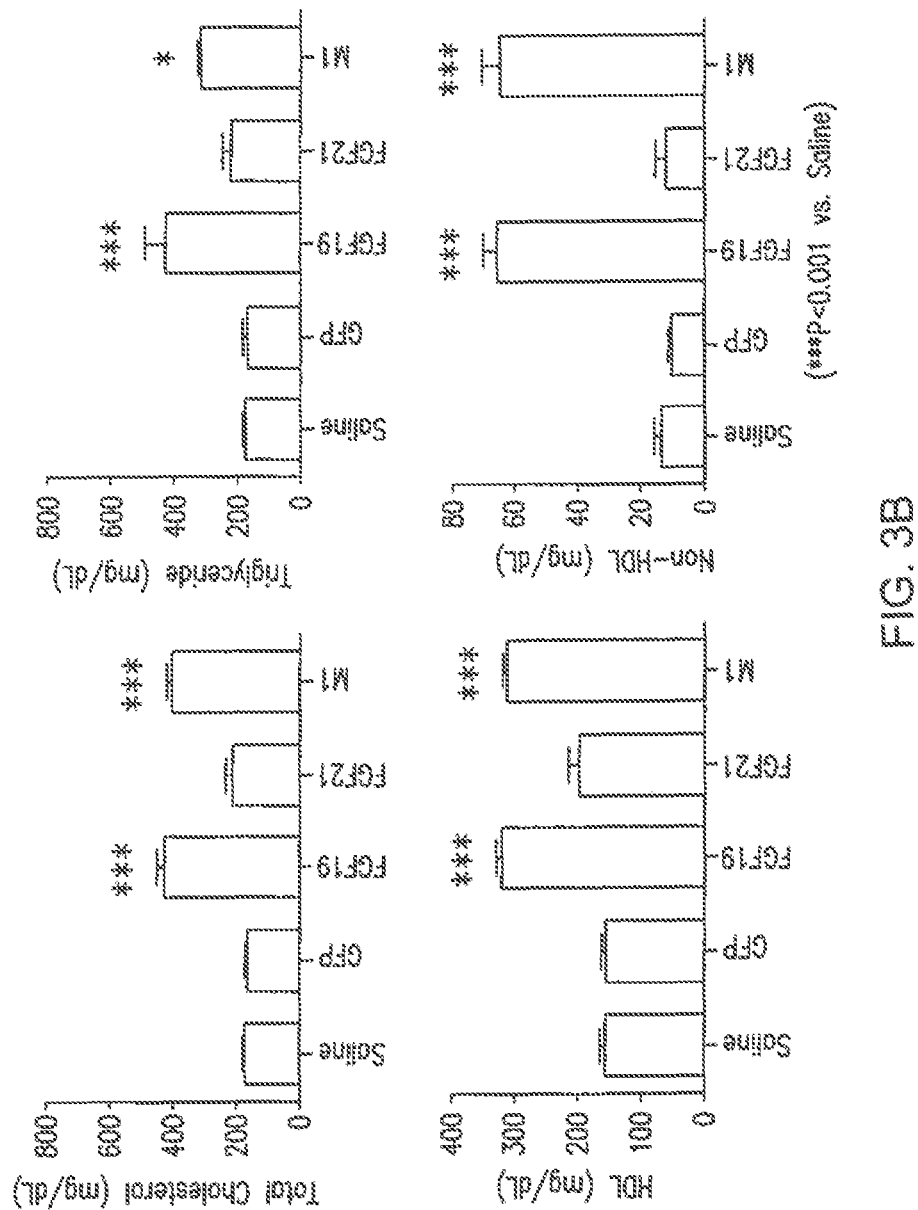
Figure 3C:
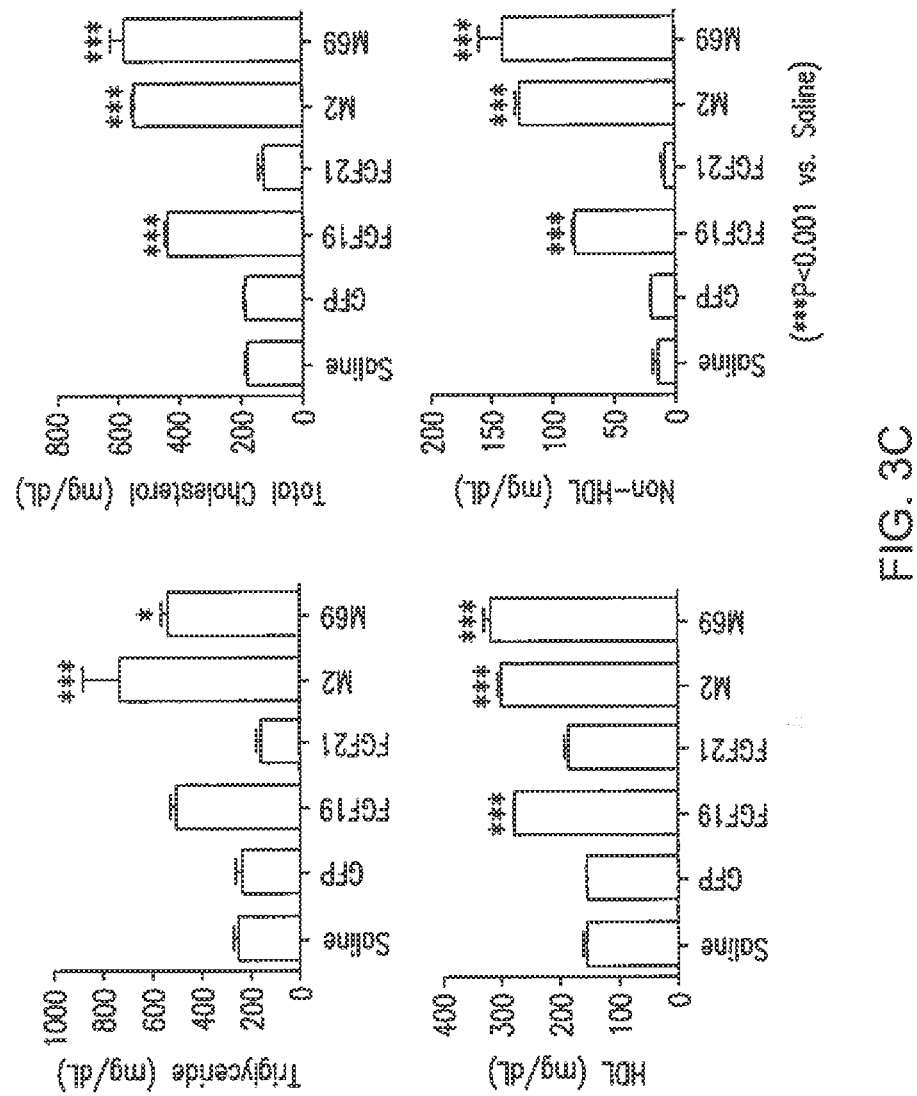
Figure 3D:
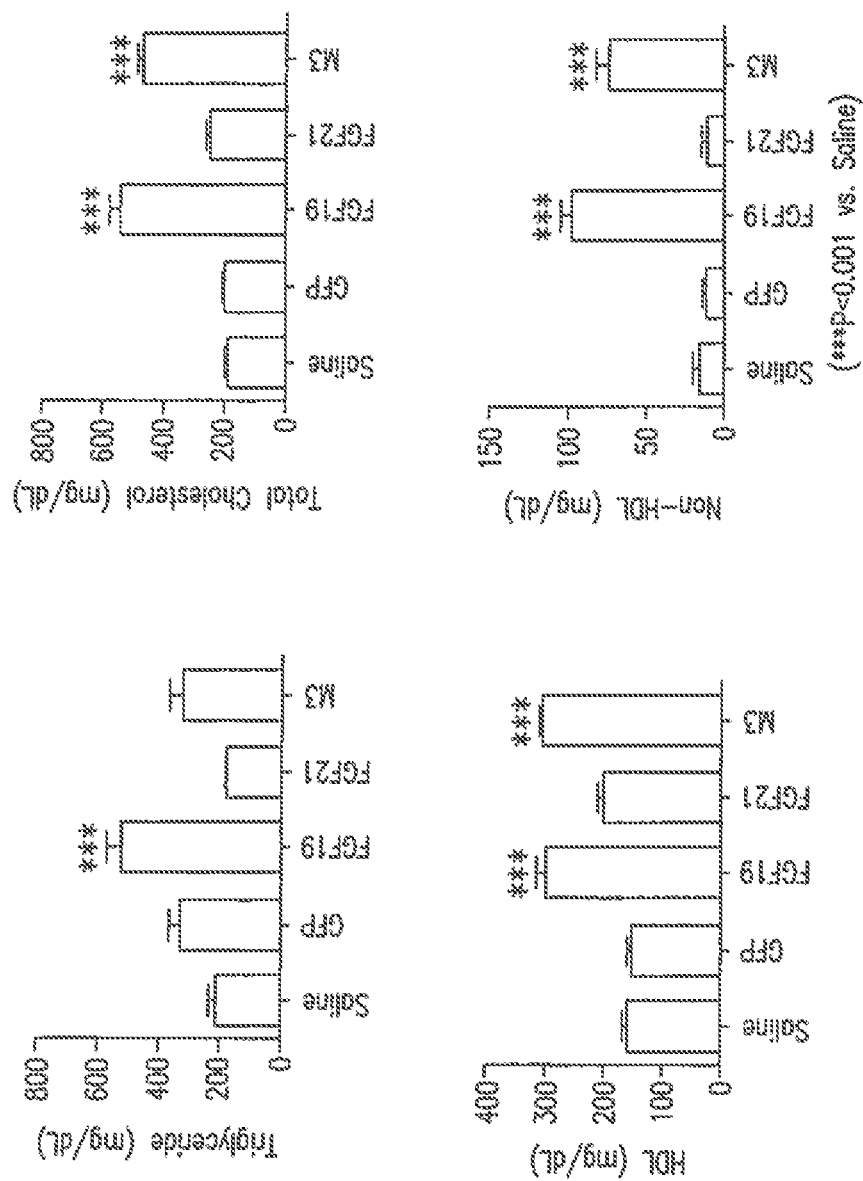
Figure 3E:
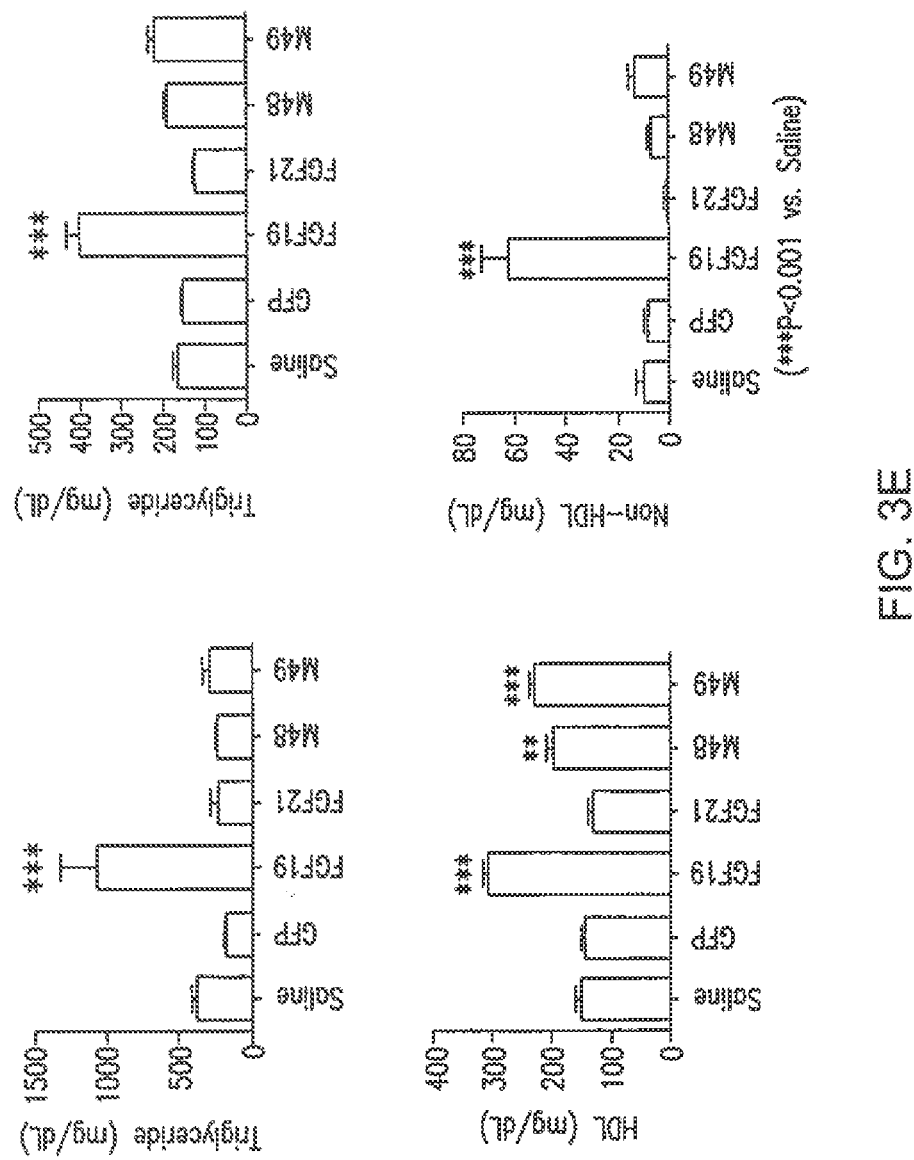
Figure 3F:
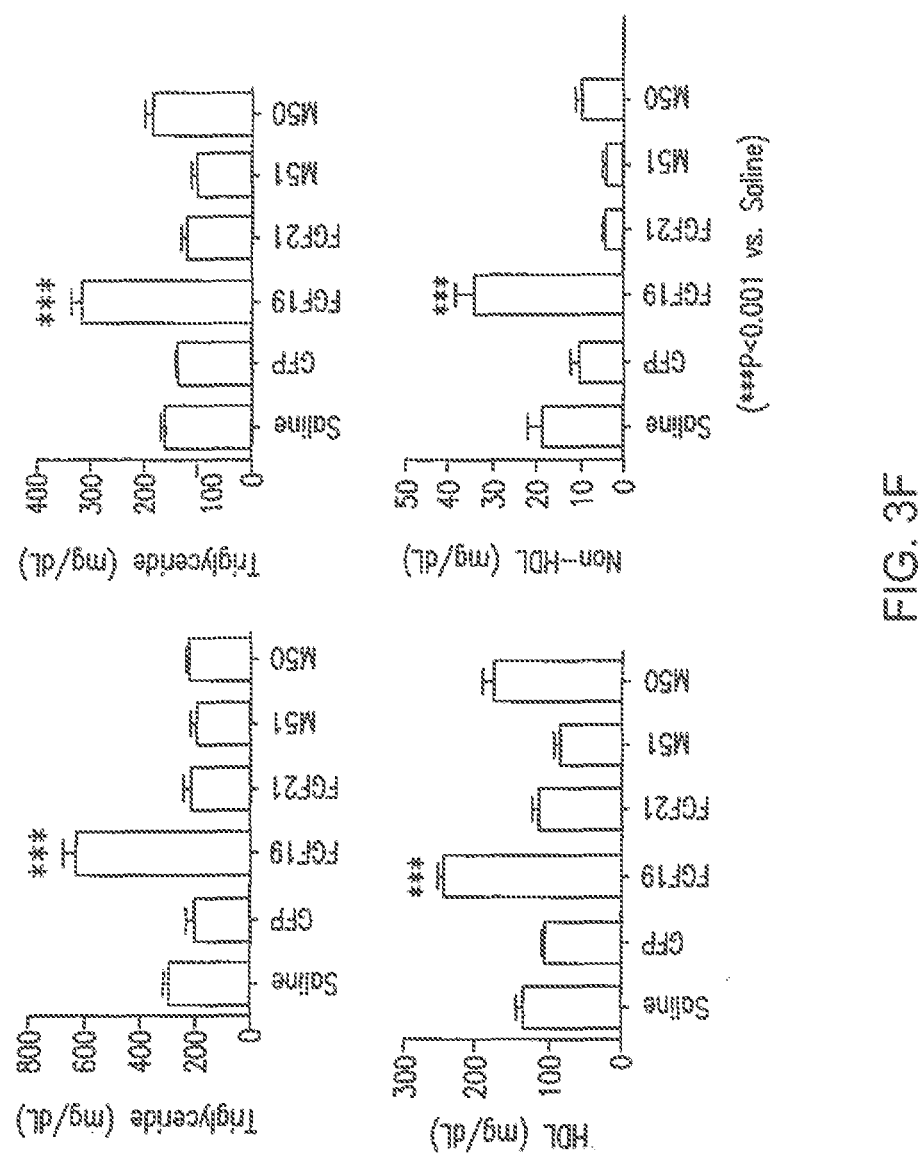
Figure 3G:
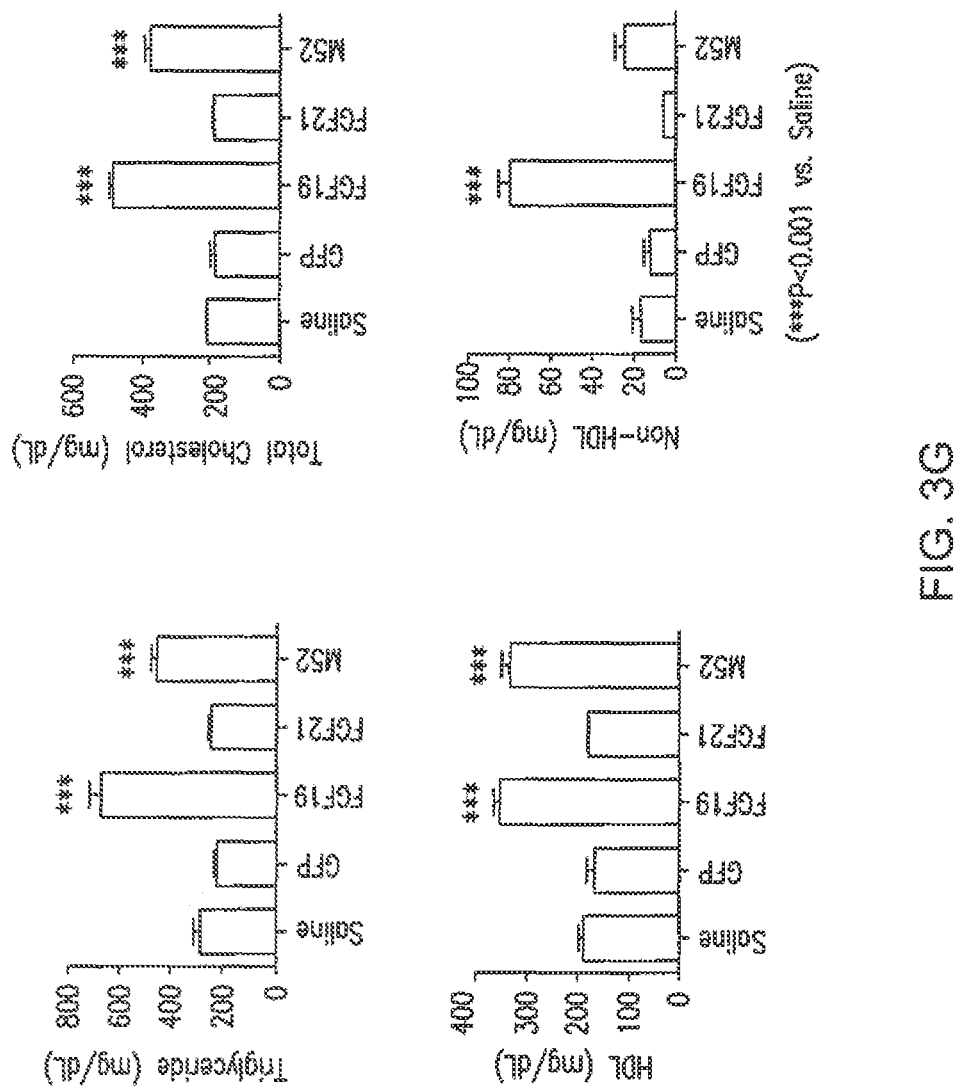
Figure 3H:
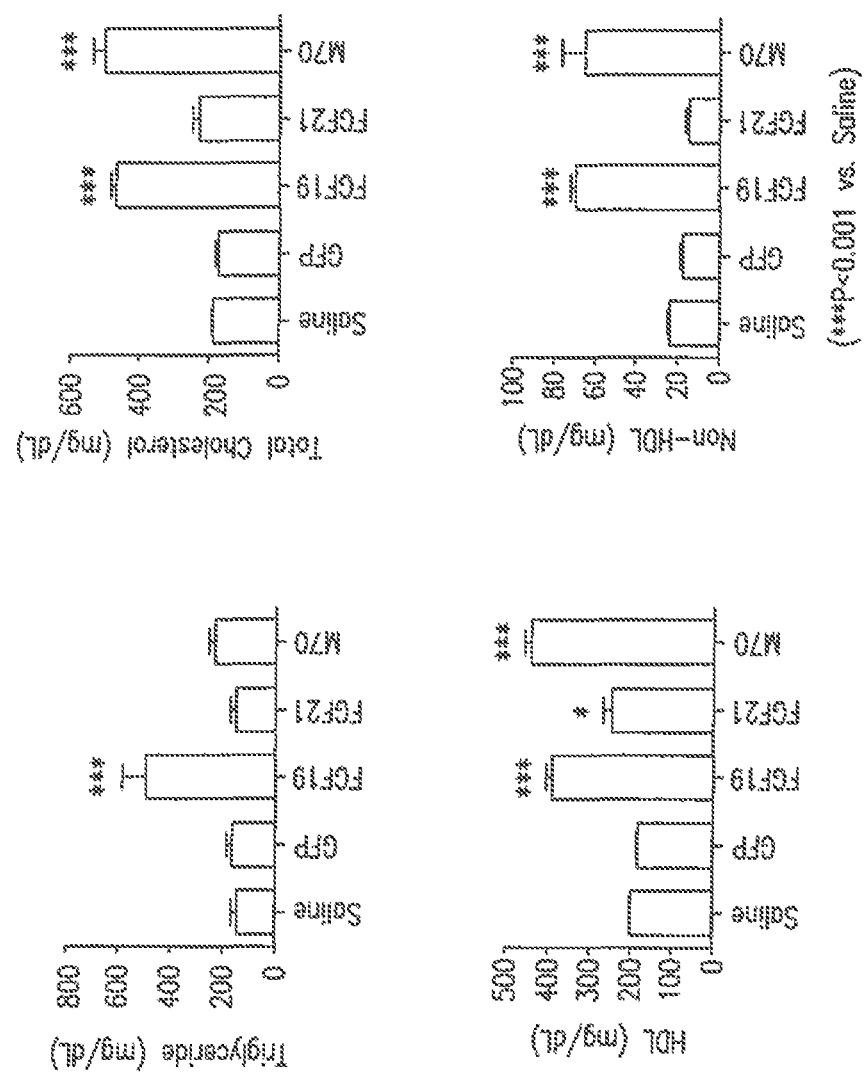
Figure 31:
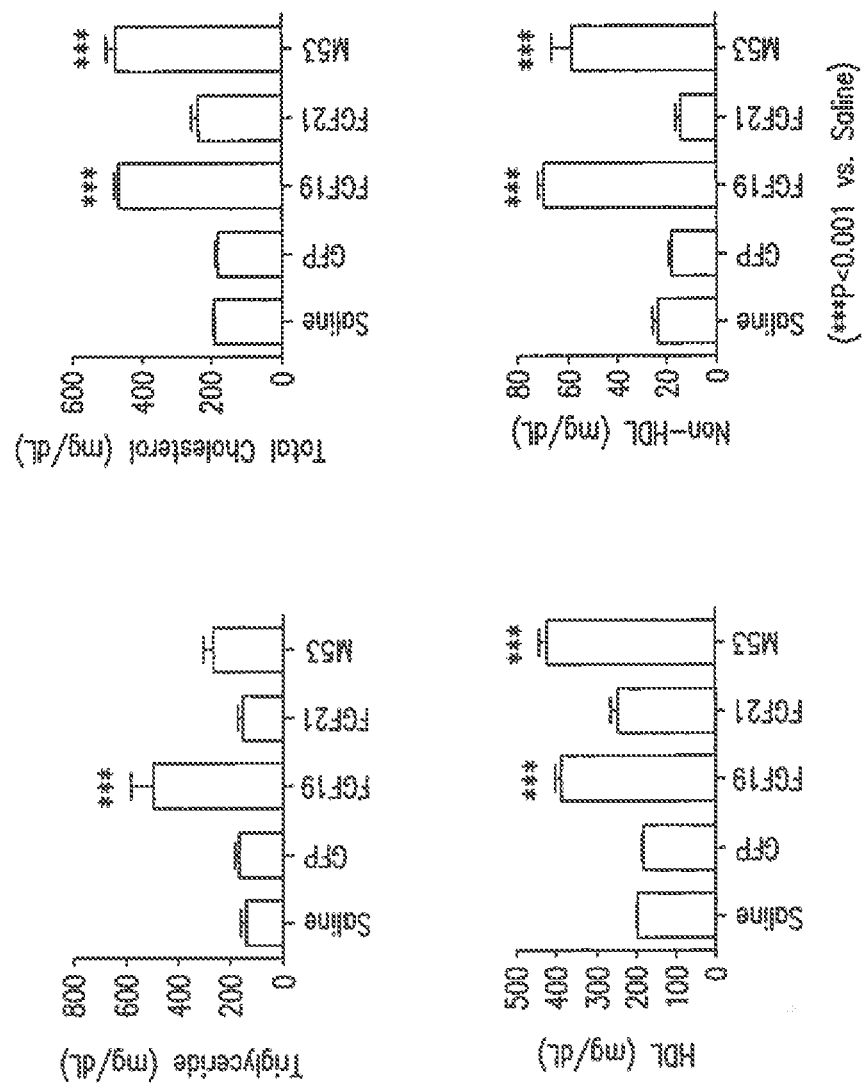

Two fusions of FGF21 and FGF19, denoted variant M5 and variant 45 (M45), exhibited glucose lowering activity and an absence of statistically significant lipid elevating or increasing activity. Variants denoted M1, M2 and M69, respectively (SEQ ID NOs:1, 2 and 69, respectively), also exhibited glucose lowering activity (FIGS. 2B and 2C, Table 5). Data comparing M5, M1, M2 and M69 glucose lowering activity and lipid elevating or increasing activity to FGF19 and FGF21 are illustrated in FIGS. 2A-2C and 3A-3C.

Example 3

The following is a description of studies showing that variants M5, M1, M2 and M69 are not tumorigenic, as determined by hepatocellular carcinoma (HCC) formation, and that variants M5, M2 and M69 also do not reduce lean muscle and fat mass.

Figure 4A:
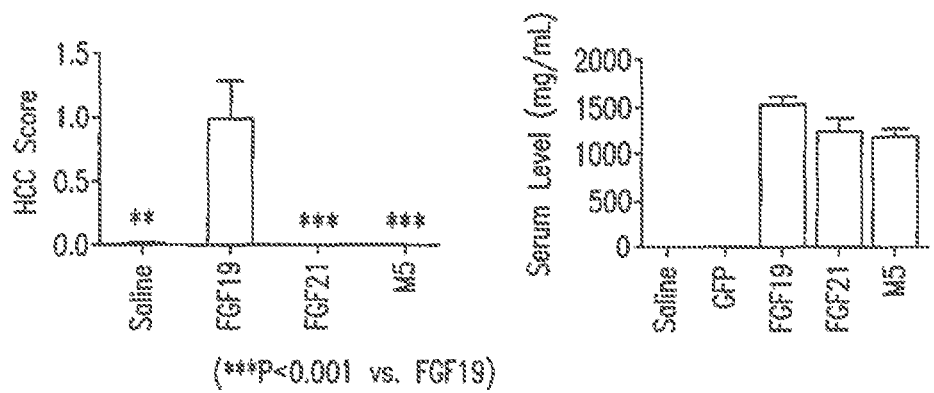
FIGS. 4A-4I show hepatocellular carcinoma (HCC)-related data for A) variant M5; B) variant M1; C) variant M2 and variant M69; D) variant M3; E) variant M48 and variant M49; F) variant M51 and variant M50; G) variant M52; H) variant M53 peptide; and I) variant M70 peptide sequences. All variants did not significantly increase or induce hepatocellular carcinoma (HCC) formation or HCC tumorigenesis, in contrast to FGF19. HCC score is recorded as the number of HCC nodules on the surface of the entire liver from variants-injected mice divided by the number of HCC nodules from wild type FGF19-injected mice.
Figure 4B:
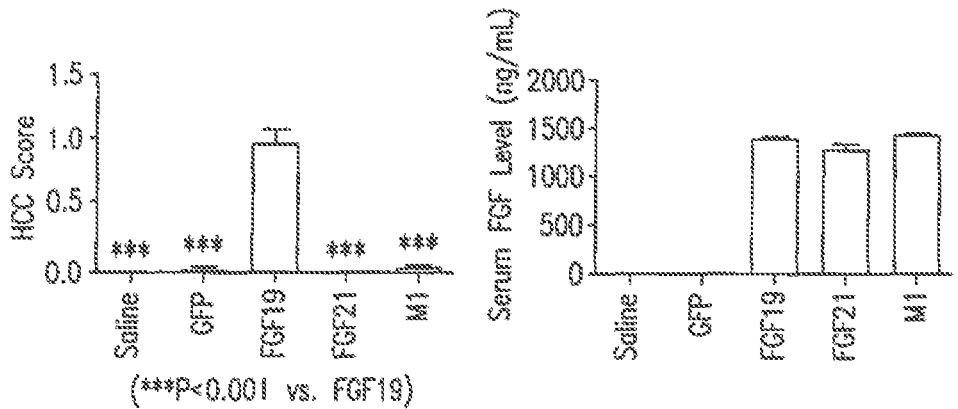
Figure 4C:
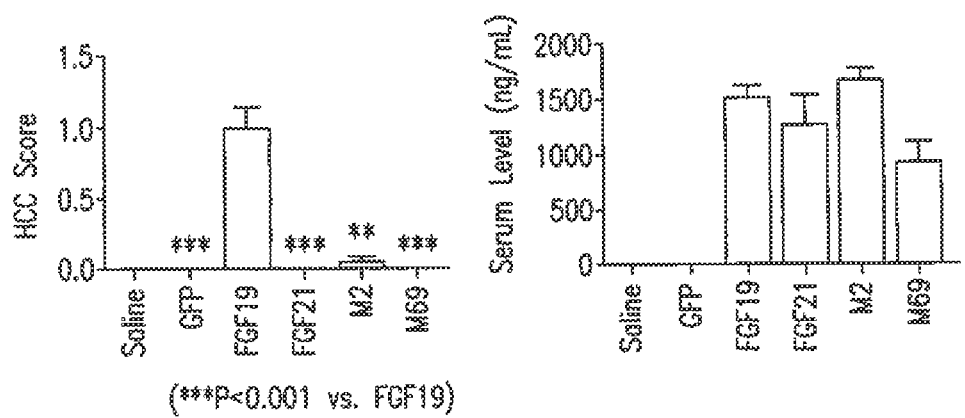
Figure 4D:
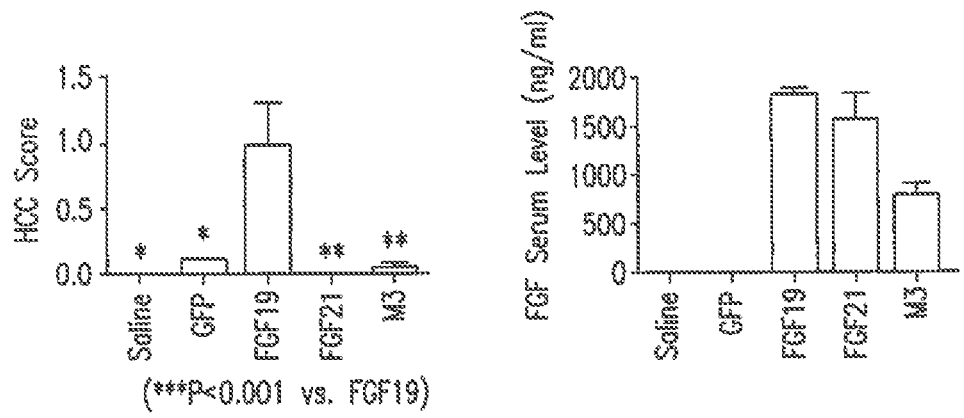
Figure 4E:
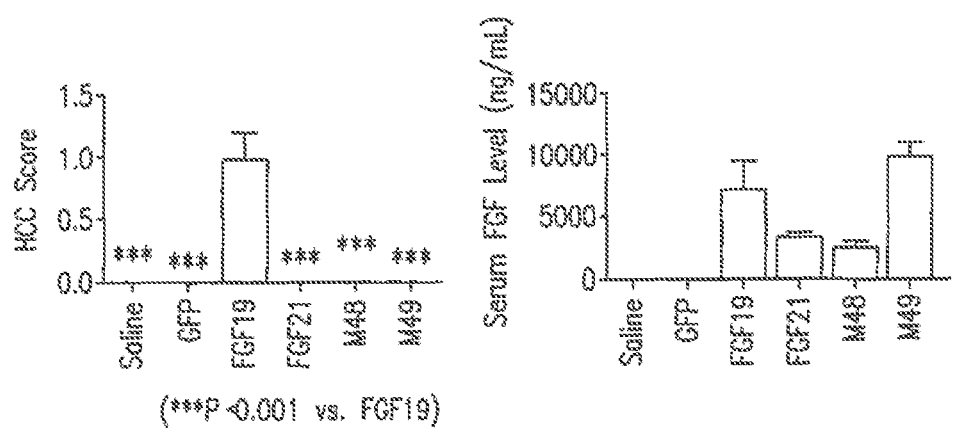
Figure 4F:
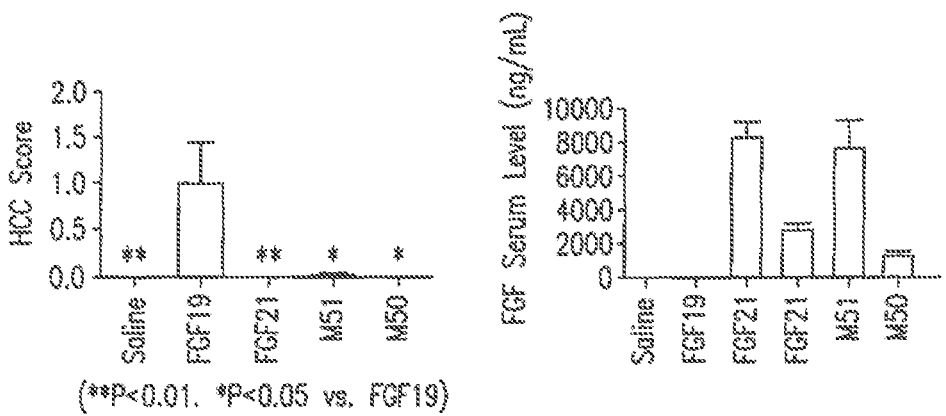
Figure 4G:
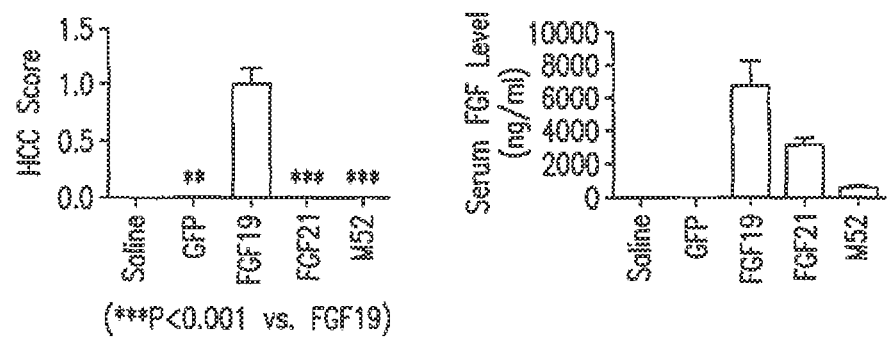
Figure 4H:
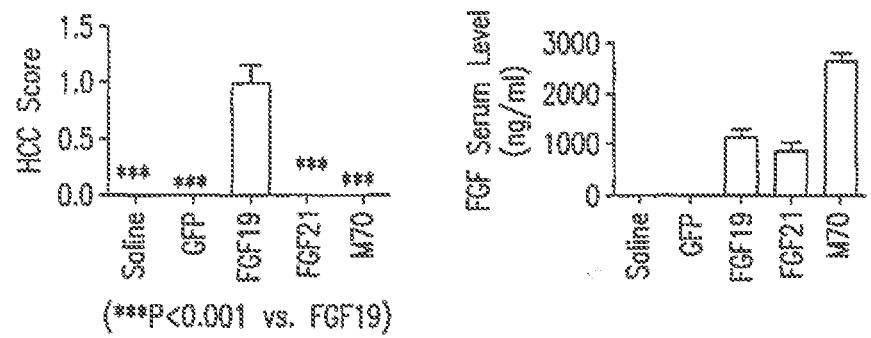
Figure 4I:
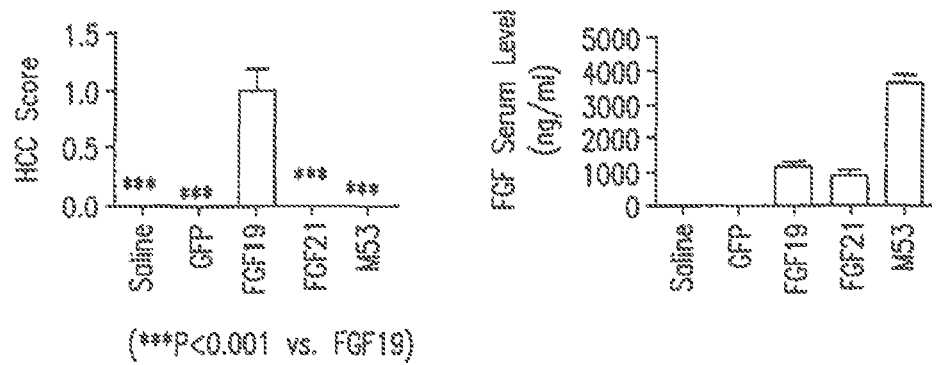

Animals (db/db) were injected with AAV vectors expressing FGF19, FGF21, M5, M1, M2, or M69, or injected with saline, and analyzed 6 months after injection. The data indicate that variants M5, M1, M2, and M69 did not induce (HCC) formation significantly (FIGS. 4A-4C).

Figure 5A:
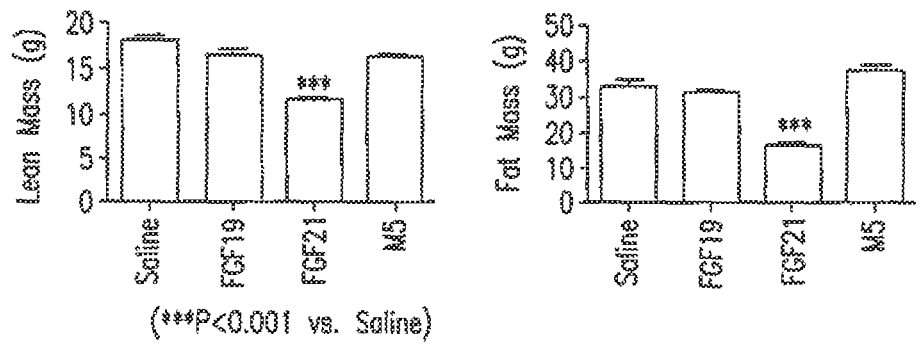
FIGS. 5A-5I show lean mass or fat mass data for A) variant M5; B) variant M1; C) variant M2 and variant M69; D) variant M3; E) variant M48 and variant M49; F) variant M51 and variant M50; G) variant M52; H) variant M53 peptide; and I) variant M70 peptide sequences. Except for M2, M5 and M69, the variant peptide sequences reduce lean mass or fat mass, in contrast to FGF21.
Figure 5B:
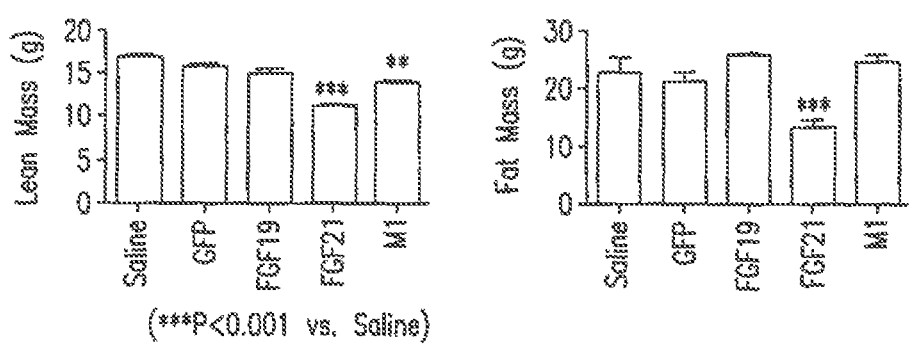
Figure 5C:
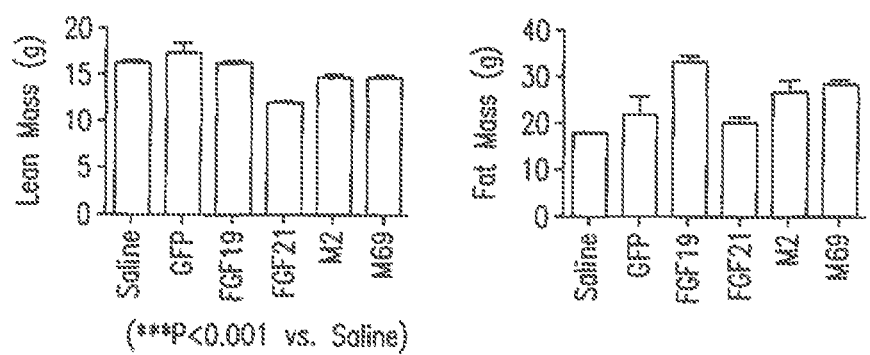
Figure 5D:
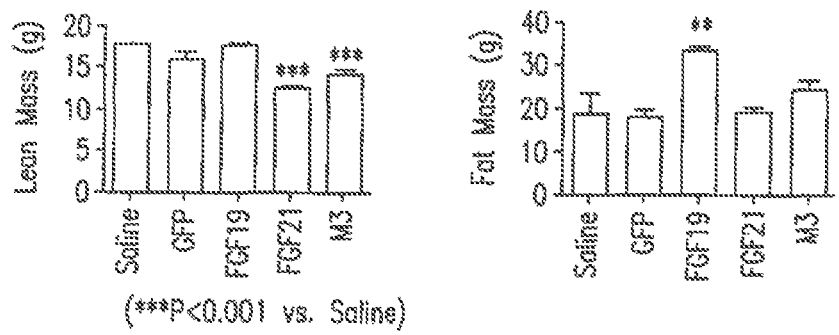
Figure 5E:
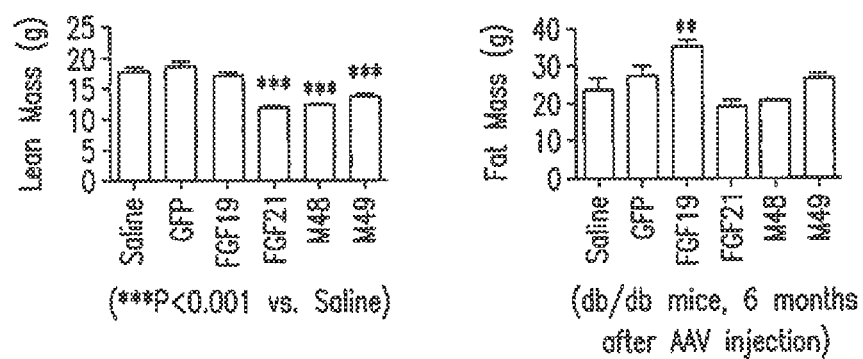
Figure 5F:
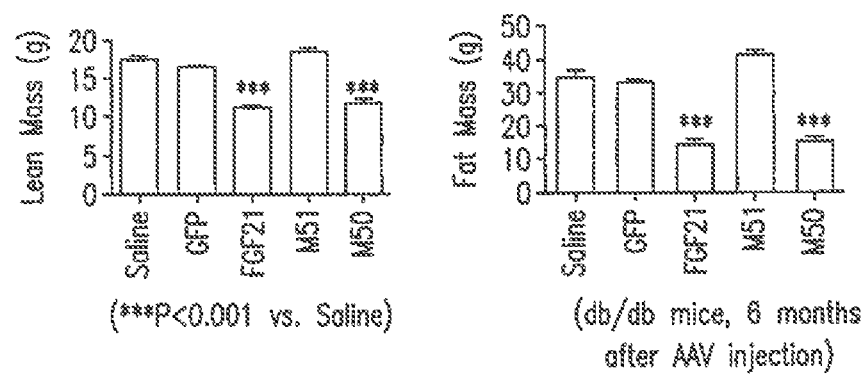
Figure 5G:
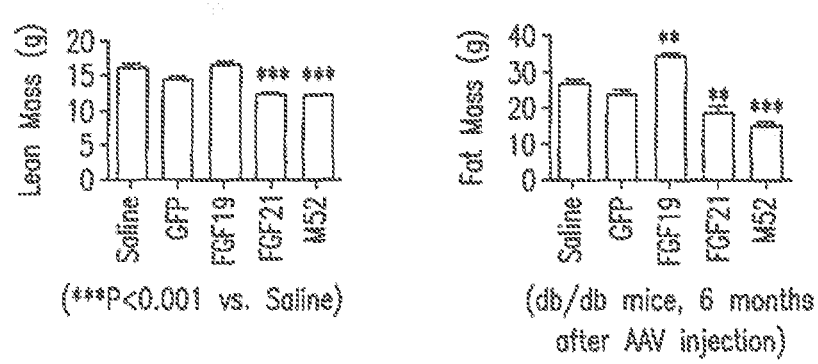
Figure 5H:
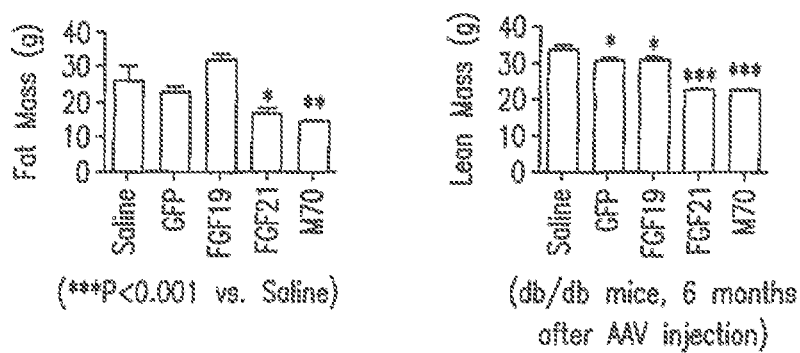
Figure 5I:
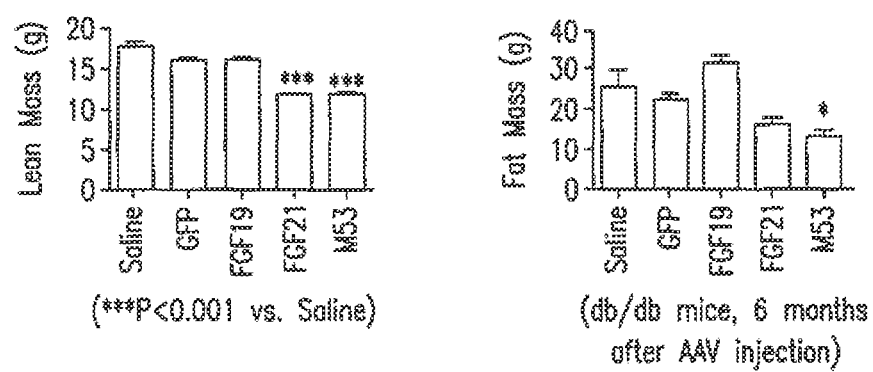

Animals (db/db mice) were also injected with viral vector expressing FGF19, FGF21, M5, M1, M2 or M69, or injected with saline, and analyzed 6 months after injection for the effect of on lean mass and fat mass. The data indicate that M5, M2 and M69 peptides did not cause a statistically significant reduction in lean mass or fat mass, in contrast to FGF21, and that M1 peptide reduces lean mass (FIGS. 5A-5C).

Example 4

The following is a data summary of 25 additional variant peptides analyzed for lipid elevating activity and tumorigenesis. The data clearly show a positive correlation between lipid elevation and tumorigenesis, as determined by hepatocellular carcinoma (HCC) formation in db/db mice.

Tables 1 to 3 summarize data for 26 different variant peptides. Such exemplified variant peptides have FGF19 C-terminal sequence: PHGLSSCFLRIRADGVVDCAR-GQSAHSLLEIKAVALRTVAIKGVHSVRYLCMGADGK-MQGLLQYSEEDCAFEEEIRPDGYNVYRSEKHRLPVS-LSSAKQRQLYKNRGFLPLSHFLPMLPMVPEEPEDLR-GHLESDMFSSPLETDSMDPFGLVTGLEAVRSPSFEK (SEQ ID NO:188) at the C-terminal portion, e.g., following the "TSG" amino acid residues. Notably, variant peptides (7 total, including M5) that did not cause a statistically significant elevation of lipids did not induce hepatocellular carcinoma (HCC) formation. In contrast, all variant peptides (17 total) that caused a statistically significant elevation of lipids also caused hepatocellular carcinoma (HCC) formation in mice. This data indicates that there is a strong positive correlation between lipid elevating activity and hepatocellular carcinoma (HCC) formation. Accordingly, lipid elevating activity can be used as an indicator and/or predictor of hepatocellular carcinoma (HCC) formation in animals.

TABLE 1

Elevated Triglyceride and Cholesterol in db/db Mice Appears to Positively Correlate With HCC Formation.

| | N-terminal Domain | SEQ ID NO: | Core | SEQ ID NO: | Lipid Elevation | HCC Formation |
|---|---|---|---|---|---|---|
| FGF19 | RPLAFS------------------DAGPHVHYGWGDPI | 99 (aa 1-20) | RLRHLYTSG | 185 | + | + |
| FGF21 | HPIPDSSPLLQ--FGGQV | 100 (aa 1-16) | RQRYLYTDD | 186 | − | − |

TABLE 1-continued

Elevated Triglyceride and Cholesterol in db/db Mice Appears to Positively Correlate With HCC Formation.

| | N-terminal Domain | SEQ ID NO: | Core | SEQ ID NO: | Lipid Elevation | HCC Formation |
|---|---|---|---|---|---|---|
| M5 | R-HPIPDSSPLLQ--FGGQV | 5 (aa 1-17) | RLRHLYTSG | 185 | − | − |
| M74 | R---------------DAGPHVHYGWGDPI | 74 (aa 1-15) | RLRHLYTSG | 185 | + | + |
| M75 | R------------------------VHYGWGDPI | 75 (aa 1-10) | RLRHLYTSG | 185 | − | − |
| M76 | R----------------------------------GDPI | 76 (11 1-5) | RLRHLYTSG | 185 | − | − |
| M77 | R----------------------------------------- | 77 (aa 1) | RLRHLYTSG | 185 | − | − |
| M78 | R----------------AGPHVHYGWGDPI | 78 (aa 1-14) | RLRHLYTSG | 185 | + | + |
| M79 | R--------------------GPHVHYGWGDPI | 79 (aa 1-13) | RLRHLYTSG | 185 | + | + |
| M80 | R----------------------PHVHYGWGDPI | 80 (aa 1-12) | RLRHLYTSG | 185 | − | − |
| M81 | R-----------------------HVHYGWGDPI | 81 ) (aa 1-11 | RLRHLYTSG | 185 | − | − |

TABLE 2

Elevated Triglyceride and Cholesterol in db/db Mice Appears to Positively Correlate with HCC Formation

| | N-terminal Domain | SEQ ID NO: | Core | SEQ ID NO: | Lipid Elevation | HCC Formation |
|---|---|---|---|---|---|---|
| FGF19 | RPLAFSDAGPHVHYGWGDPI | 99 (aa 1-20) | RLRHLYTSG | 185 | + | + |
| FGF21 | HPIPDSSPLLQ--FGGQV | 100 (1-16) | RQRYLYTDD | 186 | − | − |
| M82 | RPLAFSAAGPHVHYGWGDPI | 82 (aa 1-20) | RLRHLYTSG | 185 | + | + |
| M83 | RPLAFSDAAPHVHYGWGDPI | 83 (aa 1-20) | RLRHLYTSG | 185 | +/− | +/− |
| M84 | RPLAFSDAGAHVHYGWGDPI | 84 (aa 1-20) | RLRHLYTSG | 185 | +/− | +/− |
| M85 | RPLAFSDAGPHVHYGAGDPI | 85 (aa 1-20) | RLRHLYTSG | 185 | − | − |
| M86 | RPLAFSDAGPHVHYGWGAPI | 86 (aa 1-20) | RLRHLYTSG | 185 | + | + |
| M87 | RPLAFSDAGPHVHYGWGDAI | 87 (aa 1-20) | RLRHLYTSG | 185 | + | + |

TABLE 3

Elevated Triglyceride and Cholesterol in db/db Mice Appears to Positively Correlate with HCC Formation

| | N-terminal Domain | Core | SEQ ID NO | Lipid Elevation | HCC Formation |
|---|---|---|---|---|---|
| FGF19 | RPLAFSDAGPHVHYGWGDPI | RLRHLYTSG | 99 (aa 1-29) | + | + |
| FGF21 | HPIPDSSPLLQ--FGGQV | RQRYLYTDD | 100 (aa 1-25) | − | − |
| H31A/S141A(M89) | | FGF19 | | + | + |
| H31A/H142A(M89) | | FGF19 | | + | + |
| K127A/R129A(M90) | | FGF19 | | + | + |
| K127A/S141A(M91) | | FGF19 | | + | + |
| K127A/H142A(M92) | | FGF19 | | + | + |
| R129A/S141A(M93) | | FGF19 | | + | + |
| S141A/H142A(M94) | | FGF19 | | + | + |
| K127A/H142A(M95) | | FGF19 | | + | + |
| K127A/R129A/S141A(M96) | | FGF19 | | + | + |
| K127A/R129A/H142A(M97) | | FGF19 | | + | + |
| K127A/R129A/S141A/H142A(M98) | | FGF19 | | + | + |

Example 5

The following is a data summary of additional FGF19 variant peptides analyzed for glucose lowering activity and lipid elevating activity.

Table 4 illustrates the peptide "core sequences" of 35 additional FGF19 variants, denoted M5 to M40. Such exemplified variant peptides have FGF19 C-terminal sequence, PHGLSSCFLRIRADGVVDCARGQSAHSLLEIKAVAL-RTVAIKGVHSVRYLCMGADGKMQGLLQYSEEDCAF-EEEIRPDGYNVYRSEKHRLPVSLSSAKQRQLYKNRG-FLPLSHFLPMLPMVPEEPEDLRGHLESDMFSS-PLETDSMDPFGLVTGLEAVRSPSFEK (SEQ ID NO:188) at the C-terminal portion, e.g., following the "TSG" amino acid residues of the core sequence. The data clearly show that variants M6, M7, M8, mM38 and M39 have the desired characteristics of glucose lowering activity and not statistically significant lipid elevating activity in db/db mice.

TABLE 4

Additional Variants and Fine Mapping of the N-terminal Domain

| | N-terminal Domain | SEQ ID NO: | Core | SEQ ID NO: | Glucose Lowering | Lipid Elevation |
|---|---|---|---|---|---|---|
| FGF19 | RPLAFSDAGPHVHYGWGDPI | 99 (aa 1-20) | RLRHLYTSG | 185 | + | + |
| FGF21 | HPIPDSSPLLQ--FGGQV | 100 (aa 1-16) | RQRYLYTDD | 186 | + | − |
| M5 | R-HPIPDSSPLLQ--FGGQV | 5 (aa 1-17) | RLRHLYTSG | 185 | + | − |
| M6 | R-------DSSPLLQ--FGGQV | 6 (aa 1-18) | RLRHLYTSG | 185 | + | − |
| M7 | RPLAFSDSSPLLQ--FGGQV | 7 (aa 1-18) | RLRHLYTSG | 185 | + | − |
| M8 | R-HPIPDSSPLLQ--WGDPI | 8 (aa 1-17) | RLRHLYTSG | 185 | + | − |
| M9 | R-HPIPDSSPLLQFGWGDPI | 9 (aa 1-19) | RLRHLYTSG | 185 | + | + |
| M10 | R-HPIPDSSPHVHYGWGDPI | 10 (aa 1-19) | RLRHLYTSG | 185 | − | + |
| M11 | RPLAFSDAGPLLQ--WGDPI | 11 (aa 1-18) | RLRHLYTSG | 185 | N/D | N/D |
| M12 | RPLAFSDAGPLLQFGWGDPI | 12 (aa 1-20) | RLRHLYTSG | 185 | − | + |
| M13 | RPLAFSDAGPLLQ--FGGQV | 13 (aa 1-18) | RLRHLYTSG | 185 | − | − |
| M14 | R-HPIPDSSPHVHYG--GQV | 14 (aa 1-17) | RLRHLYTSG | 185 | − | − |
| M15 | RPLAFSDAGPHVHYG--GQV | 15 (aa 1-18) | RLRHLYTSG | 185 | + | + |
| M16 | RPLAFSDAGPHVH--WGDPI | 16 (aa 1-18) | RLRHLYTSG | 185 | N/D | N/D |
| M17 | RPLAFSDAGPHV--GWGDPI | 17 (aa 1-18) | RLRHLYTSG | 185 | N/D | N/D |
| M18 | RPLAFSDAGPH--YGWGDPI | 18 (aa 1-18) | RLRHLYTSG | 185 | N/D | N/D |
| M19 | RPLAFSDAGP-V-YGWGDPI | 19 (aa 1-18) | RLRHLYTSG | 185 | N/D | N/D |
| M20 | RPLAFSDAGP-VH-GWGDPI | 20 (aa 1-18) | RLRHLYTSG | 185 | N/D | N/D |
| M21 | RPLAFSDAGP-VHY-WGDPI | 21 (aa 1-18) | RLRHLYTSG | 185 | N/D | N/D |
| M22 | RPLAFSDAGPHV-GWGDPI | 22 (aa 1-18) | RLRHLYTSG | 185 | N/D | N/D |
| M23 | RPLAFSDAGPH-H-GWGDPI | 23 (aa 1-18) | RLRHLYTSG | 185 | N/D | N/D |
| M24 | RPLAFSDAGPH-HY-WGDPI | 24 (aa 1-18) | RLRHLYTSG | 185 | N/D | N/D |
| M25 | RPLAFSDAGPHV-Y-WGDPI | 25 (aa 1-18) | RLRHLYTSG | 185 | N/D | N/D |
| M26 | RPLAFSDSSPLVH--WGDPI | 26 (aa 1-18) | RLRHLYTSG | 185 | N/D | N/D |
| M27 | RPLAFSDSSPHVH--WGDPI | 27 (aa 1-18) | RLRHLYTSG | 185 | N/D | N/D |
| M28 | RPLAFSDAPHV---WGDPI | 28 (aa 1-16) | RLRHLYTSG | 185 | N/D | N/D |
| M29 | RPLAFSDAGPHVHY-WGDPI | 29 (aa 1-19) | RLRHLYTSG | 185 | N/D | N/D |
| M30 | RPLAFSDAGPHVHYAWGDPI | 30 (aa 1-20) | RLRHLYTSG | 185 | N/D | N/D |
| M31 | R-HPIPDSSPLLQ--FGAQV | 31 (aa 1-17) | RLRHLYTSG | 185 | +/− | − |
| M32 | R-HPIPDSSPLLQ--FGIYQV | 32 (aa 1-18) | RLRHLYTSG | 185 | − | − |
| M33 | R-HPIPDSSPLLQ--FGGQV | 33 (aa 1-17) | RLRHLYTSG | 185 | − | − |
| M34 | R-HPIPDSSPLLQ--FGGAV | 34 (aa 1-17) | RLRHLYTSG | 185 | +/− | − |

TABLE 4 -continued

Additional Variants and Fine Mapping of the N-terminal Domain

| | N-terminal Domain | SEQ ID NO: | Core | SEQ ID NO: | Glucose Lowering | Lipid Elevation |
|---|---|---|---|---|---|---|
| M35 | R-HPIPDSSPLLQ--FGGEV | 35 (aa 1-17) | RLRHLYTSG | 185 | +/- | +/ |
| M36 | R-HPIPDSSPLLQ--FGGQV | 36 (aa 1-17) | RLRHLYTSG | 185 | +/- | - |
| M37 | R-HPIPDSSPLLQ--FGGQA | 37 (aa 1-17) | RLRHLYTSG | 185 | - | - |
| M38 | R-HPIPDSSPLLQ--FGGQI | 38 (aa 1-17) | RLRHLYTSG | 185 | + | - |
| M39 | R-HPIPDSSPLLQ--FGGQT | 39 (aa 1-17) | RLRHLYTSG | 185 | + | - |
| M40 | R-HPIPDSSPLLQFGWGQPV | 40 (aa 1-19) | RLRHLYTSG | 185 | - | + |

TABLE 4a

| | N-terminal Domain | Core | SEQ ID NO. | Glucose Lowering | Lipid Elevation | HCC Formation |
|---|---|---|---|---|---|---|
| FGF19 | RPLAFSDAGPHVHYGWGDPI | RLRHLYTSG | 99 (aa 1-29) | + | + | + |
| FGF21 | HPIPDSSPLLQ--FGGQV | RQRYLYTDD | 100 (aa 1-25) | + | - | - |
| M5 | R-HPIPDSSPLLQ--FGGQV | RLRHLYTSG | 5 (aa 1-26) | + | - | - |
| M9 | R-HPIPDSSPLLQFGWGDPI | RLRHLYTSG | 9 (aa 1-28) | + | + | + |
| M8 | R-HPIPDSSPLLQ--WGDPI | RLRHLYTSG | 8 (aa 1-26) | + | + | + |
| M12 | RPLAFSDAGPLLQFGWGDPI | RLRHLYTSG | 12 (aa 1-29) | - | + | + |
| M10 | R-HPIPDSSPHVHYGWGDPI | RLRHLYTSG | 10 (aa 1-28) | - | + | + |
| M13 | RPLAFSDAGPLLQ--FGGQV | RLRHLYTSG | 13 (aa 1-27) | - | + | + |
| M15 | RPLAFSDAGPHVHYG--GQV | RLRHLYTSG | 15 (aa 1-27) | - | - | +/- |
| M14 | R-HPIPDSSPHVHYG--GQV | RLRHLYTSG | 14 (aa 1-26) | - | - | +/- |
| M43 | RPLAFSDAGPHVHYG-GD-I | RLRHLYTSG | 43 (aa 1-27) | + | - | +/- |
| M6 | R-----DSSPLLQ--FGGQV | RLRHLYTSG | 6 (aa 1-22) | + | - | - |
| M7 | RPLAFSDSSPLLQ--FGGQV | RLRHLYTSG | 7 (aa 1-27) | - | - | - |

TABLE 4b

| | N-terminal Domain | Core | SEQ ID NO. | Glucose Lowering | Lipid Elevation | HCC Formation |
|---|---|---|---|---|---|---|
| FGF19 | RPLAFSDAGPHVHYGWGDPI | RLRHLYTSG | 99 (aa 1-29) | + | + | + |
| FGF21 | HPIPDSSPLLQ--FGGQV | RQRYLTDD | 100 (aa 1-25) | + | - | - |
| M5 | R-HPIPDSSPLLQ--FGGQV | RLRHLYTSG | 5 (aa 1-26) | + | - | - |
| M31 | R-HPIPDSSPLLQ--FGAQV | RLRHLYTSG | 31 (aa 1-26) | + | - | + |
| M32 | R-HPIPDSSPLLQ--FGDQV | RLRHLYTSG | 32 (aa 1-26) | + | - | - |
| M33 | R-HPIPDSSPLLQ--FGPQV | RLRHLYTSG | 33 (aa 1-26) | - | - | + |
| M34 | R-HPIPDSSPLLQ--FGGAV | RLRHLYTSG | 34 (aa 1-26) | - | - | + |
| M35 | R-HPIPDSSPLLQ--FGGEV | RLRHLYTSG | 35 (aa 1-26) | - | - | + |
| M36 | R-HPIPDSSPLLQ--FGGNV | RLRHLYTSG | 36 (aa 1-26) | + | - | +/- |
| M37 | R-HPIPDSSPLLQ--FGGQA | RLRHLYTSG | 37 (aa 1-26) | - | - | + |
| M38 | R-HPIPDSSPLLQ--FGGQI | RLRHLYTSG | 38 (aa 1-26) | - | - | + |
| M39 | R-HPIPDSSPLLQ--FGGQT | RLRHLYTSG | 39 (aa 1-26) | - | - | + |
| M40 | R-HPIPDSSPLLQFGWGQPV | RLRHLYTSG | 40 (aa 1-28) | - | + | + |

TABLE 4c

| | N-terminal Domain | Core | SEQ ID NO. | Glucose Lowering | Lipid Elevation | HCC Formation |
|---|---|---|---|---|---|---|
| FGF19 | RPLAFSDAGPHVHYGWGDPI | RLRHLYTSG | 99 (aa 1-29) | + | + | + |
| FGF21 | HPIPDSSPLLQ--FGGQV | RQRYLYTDD | 100 (aa 1-25) | + | - | - |
| M5 | R-HPIPDSSPLLQ--FGGQV | RLRHLYTSG | 5 (aa 1-26) | + | - | - |
| M52 | R-----DSSPLLQ--WGDPI | RLRHLYTSG | 52 (aa 1-22) | + | + | - |
| M54 | RPLAFSDAGPLLQ--WGDPI | RLRHLYTSG | 54 (aa 1-27) | - | + | + |
| M55 | RPLAFSDAGPH--YGWGDPI | RLRHLYTSG | 55 (aa 1-27) | - | + | + |
| M56 | RPLAFSDAGP-V-YGWGDPI | RLRHLYTSG | 56 (aa 1-27) | - | + | + |
| M57 | RPLAFSDAGP-VT-GWGDPI | RLRHLYTSG | 57 (aa 1-27) | - | + | + |
| M58 | RPLAFSDAGP-VHY-WGDPI | RLRHLYTSG | 58 (aa 1-27) | - | + | + |
| M59 | RPLAFSDAGPH-H-GWGDPI | RLRHLYTSG | 59 (aa 1-27) | - | + | + |

TABLE 4c-continued

| | N-terminal Domain | Core | SEQ ID NO. | Glucose Lowering | Lipid Elevation | HCC Formation |
|---|---|---|---|---|---|---|
| M60 | RPLAFSDAGPH-HY-WGDPI | RLRHLYTSG | 60 (aa 1-27) | − | + | + |
| M61 | RPLAFSDAGPHV--GWGDPI | RLRHLYTSG | 61 (aa 1-27) | − | + | + |
| M62 | RPLAFSDAGPHV-Y-WGDPI | RLRHLYTSG | 62 (aa 1-27) | − | + | + |
| M63 | RPLAFSDAGPHVH--WGDPI | RLRHLYTSG | 63 (aa 1-27) | + | + | + |
| M64 | RPLAFSDSSPLVH--WGDPI | RLRHLYTSG | 64 (aa 1-27) | + | + | + |
| M65 | RPLAFSDSSPHVH--WGDPI | RLRHLYTSG | 65 (aa 1-27) | − | + | + |
| M66 | RPLAFSDAGPHLQ--WGDPI | RLRHLYTSG | 66 (aa 1-27) | + | + | + |
| M67 | RPLAFSDAGPHV---WGDPI | RLRHLYTSG | 67 (aa 1-26) | − | − | +/− |
| M68 | RPLAFSDAGPHVHY-WGDPI | RLRHLYTSG | 68 (aa 1-28) | − | + | − |
| M4  | RPLAFSDAGPHVHYAWGDPI | RLRHLYTSG | 4 (aa 1-29) | + | + | + |
| M69 | R-----DSSPLVHYGWGDPI | RLRHLYTSG | 69 (aa 1-24) | + | + | − |
| M70 | MR----DSSPLVHYGWGDPI | RLRHLYTSG | 70 (aa 1-25) | + | + | − |
| M53 | M-----DSSPLLQ--WGDPI | RLRHLYTSG | 192 (aa 1-22) | + | + | − |

Table 5 illustrates the peptide sequences of 3 additional FGF19 variants, denoted M1, M2 and M69. The data clearly show that these three variants have the desired characteristics of glucose lowering activity in db/db mice (FIGS. 2B and 2C). These three variants appear to elevate lipids in db/db mice FIGS. 3B and 3C).

TABLE 5

Additional Variants

M1: RPLAFSDASPHVHYGWGDPIRLRHLYTSGPHGLSSCFLRIRADGVV
DCARGQSAHSLLEIKAVALRTVAIKGVHSVRYLCMGADGKMQGLLQYSEE
DCAFEEEIRPDGYNVYRSEKHRLPVSLSSAKQRQLYKNRGFLPLSHFLPM
LPMVPEEPEDLRGHLESDMFSSPLETDSMDPFGLVTGLEAVRSPSFEK
(SEQ ID NO: 1)

M2: RPLAFSDSSPLVHYGWGDPIRLRHLYTSGPHGLSSCFLRIRADGVV
DCARGQSAHSLLEIKAVALRTVAIKGVHSVRYLCMGADGKMQGLLQYSEE
DCAFEEEIRPDGYNVYRSEKHRLPVSLSSAKQRQLYKNRGFLPLSHFLPM
LPMVPEEPEDLRGHLESDMFSSPLETDSMDPFGLVTGLEAVRSPSFEK
(SEQ ID NO: 2)

TABLE 5 -continued

Additional Variants

M69: RDSSPLVHYGWGDPIRLRHLYTSGPHGLSSCFLRIRADGVVDCAR
GQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMV
PEEPEDLRGHLESDMFSSPLETDSMDPFGLVTGLEAVRSPSFEK
(SEQ ID NO: 69)

Example 6

The following is a data summary showing that FGF19 reduces body weight in diet-induced obese mice and in ob/ob mice, and liver tumor formation activity and body weight in db/db mice.

Mice were injected with FGF19 or FGF21 in AAV vector. Body weight was recorded 4 weeks after injection.

TABLE 6

FGF19 reduces body weight in diet-induced obese mice and in ob/ob mice

| | N-terminal Domain | core | SEQ ID NO. | Body Weight-Lowering in DIO | Body Weight-Lowering in ob/ob |
|---|---|---|---|---|---|
| FGF19 | RPLAFSDAGPHVHYGWGDPI | RLRHLYTSG | 99 (aa 1-29) | Increased | |
| FGF21 | HPIPDSSPLLQ--FGGQV | RQRYLYTDD | 100 (aa 1-25) | Decreased | |

TABLE 7

Correlation of body weight and liver tumor formation of FGF19, FGF21 and selected variants in db/db mice

| | N-terminal Domain | Core | SEQ ID NO | Liver Tumor Nodule | Body Weight |
|---|---|---|---|---|---|
| FGF19 | RPLAFSDAGPHVHYGWGDPI | RLRHLYTSG | 99 (aa 1-29) | + | Increased |
| FGF21 | HPIPDSSPLLQ--FGGQV   | RQRYLYTDD | 100 (aa 1-25) | − | Decreased |
| M5    | R-HPIPDSSPLLQ--FGGQV | RLRHLYTSG | 5 (aa 1-26) | − | Increased |
| M6    | R-----DSSPLLQ--FGGQV | RLRHLYTSG | 6 (aa 1-22) | − | Decreased |
| M32   | R-HPIPDSSPLLQ--FGDQV | RLRHLYTSG | 32 (aa 1-26) | − | Decreased |
| M52   | R-----DSSPLLQ--WGDPI | RLRHLYTSG | 52 (aa 1-22) | − | Decreased |
| M69   | R-----DSSPLVHYGWGDPI | RLRHLYTSG | 69 (aa 1-24) | − | Increased |

Example 7

The following is a study showing that variant M5 and variant M69 peptides reduce blood glucose.

Figure 6A:
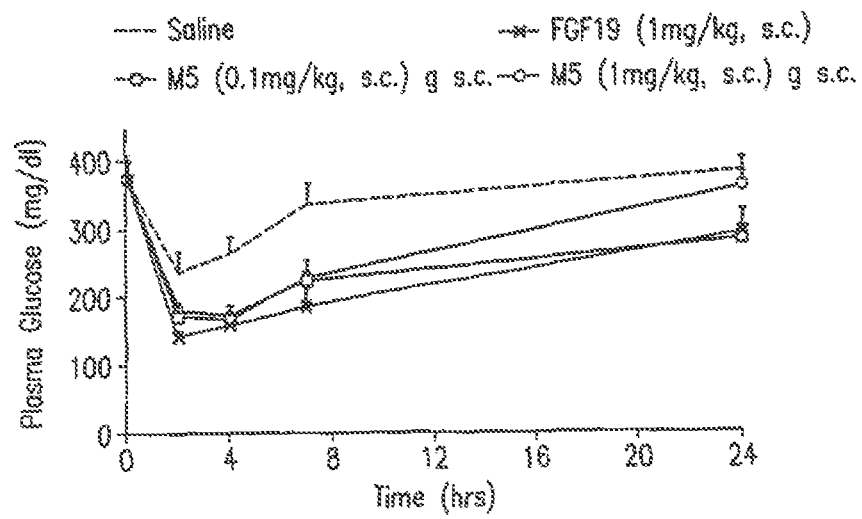
FIGS. 6A-6B show graphical data demonstrating that injection of the recombinant A) variant M5; and B) variant M69 polypeptides reduce blood glucose in ob/ob mice.
Figure 6B:
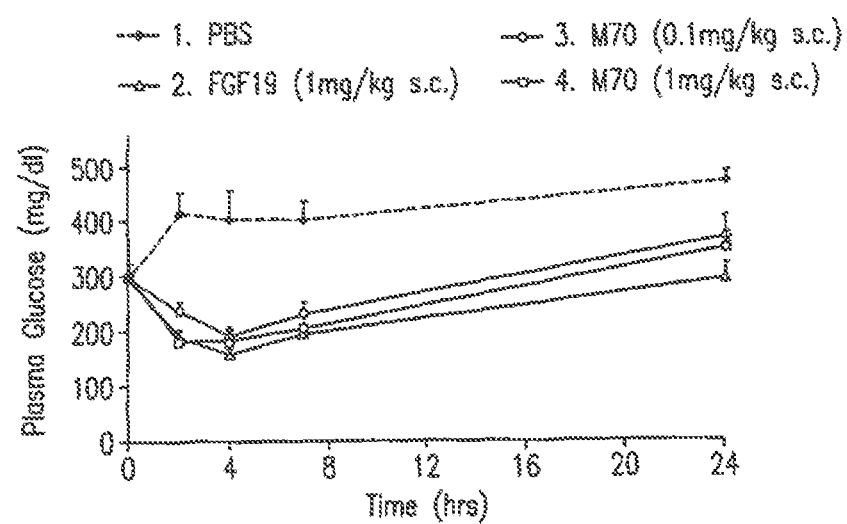

Mice (ob/ob) were injected (subcutaneously) with M5 (0.1 and 1 mg/kg, s.c.) or FGF19 (1 mg/kg, s.c.), or variant M69 (0.1 and 1 mg/kg, s.c.) or FGF19 (1 mg/kg, s.c.). Plasma glucose levels were measured at 2, 4, 7, and 24 hours after injection, and the results are shown in FIG. 6. M5 (FIG. 6A) and variant M69 (FIG. 6B) showed similar glucose lowering effects as wild type FGF19.

Example 8

This example describes a study showing that liver expression of aldo-keto reductase family 1, member C18 (Akr1C18) and solute carrier family 1, member 2 (slc1a2) appears to correlate with HCC activity.

Figure 7:
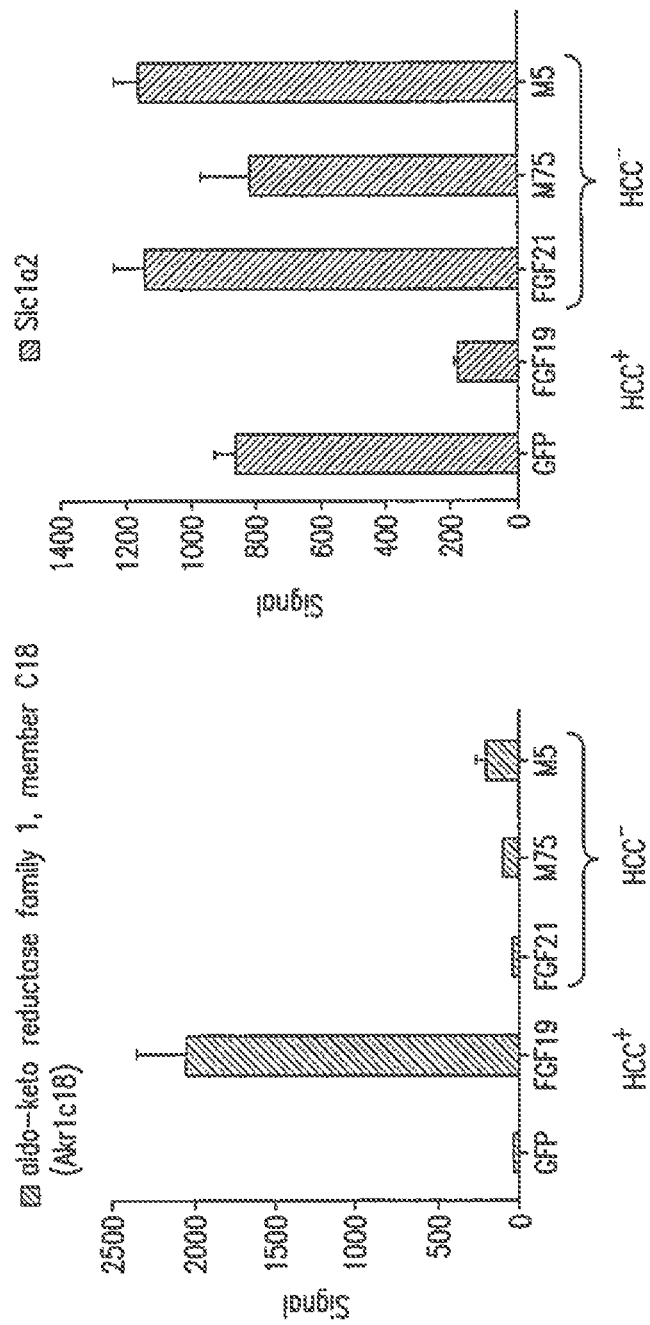
FIG. 7 shows data indicating that liver expression of aldo-keto reductase family 1, member C18 (Akr1C18) and solute carrier family 1, member 2 (slc1a2) appears to correlate with HCC activity.

Mice (db/db) were injected with viral vector expressing FGF19 (HCC+), FGF21 (HCC−), dN2 (HCC−) or M5 (HCC−), or injected with GFP. Liver samples were harvested and analyzed by quantitative RT-PCR 2 weeks after injection. The data, shown in FIG. 7, shows that liver expression of Akr1C18 and slc1a2 appears to correlate with HCC activity.

TABLE 8

Summary of FGF19 Variants in 3T3L1 Adipocyte Signaling Assay

| P-Erk assay in 3T3L1 adipocytes | FGF19 | FGF21 | M5 | M2 | M63 | M64 | M1 | M8 |
|---|---|---|---|---|---|---|---|---|
| Experiment#1: | | | | | | | | |
| Emax | 3.67 | 4.33 | 3.52 | 4.19 | 3.21 | 3.67 | 4.24 | 4.16 |
| EC50 (nM) | 0.05 | 0.65 | 0.03 | 0.05 | 0.92 | 0.02 | 0.03 | 0.03 |
| Experiment#2: | | | | | | | | |
| Emax | 4.52 | 4.83 | 4.01 | 5.56 | 4.17 | 4.85 | 5.30 | 5.34 |
| EC50 (nM) | 0.33 | 1.48 | 0.14 | 0.15 | 0.66 | 0.12 | 0.09 | 0.09 |
| Experiment#3: | | | | | | | | |
| Emax | 4.09 | 4.14 | 3.74 | 4.24 | 3.15 | 4.15 | 4.77 | 4.16 |
| EC50 (nM) | 0.16 | 1.50 | 0.24 | 0.14 | 0.28 | 0.14 | 0.07 | 0.14 |

Sequence Listing

The present specification is being filed with a computer readable form (CRF) copy of the Sequence Listing. The CRF entitled 13370-048-999_SEQLIST.txt, which was created on Dec. 24, 2015 and is 234,866 bytes in size, is incorporated herein by reference in its entirety.

What is claimed is:

1. A method of reducing glucose levels in a subject in need thereof, comprising administering to the subject an effective amount of a peptide having an amino acid sequence comprising or consisting of (SEQ ID NO: 69)
RDSSPLVHYGWGDPIRLRHLYTSGPHGLSSCFLRIRADGVVDCARGQSAH

SLLEIKAVALRTVAIKGVHSVRYLCMGADGKMQGLLQYSEEDCAFEEEIR

PDGYNVYRSEKHRLPVSLSSAKQRQLYKNRGFLPLSHFLPMLPMVPEEPE

DLRGHLESDMFSSPLETDSMDPFGLVTGLEAVRSPSFEK.

2. The method of claim 1, wherein the peptide has an amino acid sequence comprising SEQ ID NO:69.

3. The method of claim 2, wherein the peptide is fused with an immunoglobulin Fc region.

4. The method of claim 3, wherein the peptide is formulated as a pharmaceutical composition, wherein the pharmaceutical composition further comprises a pharmaceutically acceptable carrier.

5. The method of claim 3, wherein the method further comprises administration of a supplemental therapy.

6. The method of claim 5, wherein said supplemental therapy is a weight loss surgery, gastric bypass, gastrectomy, gastric banding, gastric balloon, or gastric sleeve.

7. The method of claim 5, wherein said supplemental therapy is a glucose lowering agent, insulin, GLP1 analogue, biguanide, sulphonylurea, thiazolidinedione, a DPP-4 inhibitor, a bromocriptine formulation, a bile acid sequestrant, metformin, a TZD, a SGLT-2 inhibitor, or any combination thereof.

8. The method of claim 7, wherein said biguanide or sulphonylurea is selected from the group consisting of tolbutamide, chlorpropamide, acetohexamide, tolazamide, glibenclamide, glipizide or any combination thereof.

9. The method of claim 7, wherein said thiazolidinedione is rosiglitazone or pioglitazone, or combination thereof.

10. The method of claim 7, wherein said bile acid sequestrant is colesevelam.

11. The method of claim 7, wherein said insulin is bolus insulin, basal insulin, or an analogue thereof.

12. The method of claim 5, wherein said supplemental therapy is administered prior to said method.

13. The method of claim 5, wherein said supplemental therapy is administered contemporaneously with said method.

14. The method of claim 5, wherein said supplemental therapy is administered following said method.

15. The method of claim 3, wherein the glucose levels are blood glucose levels.

16. The method of claim 3, wherein the subject has a metabolic disorder.

17. The method of claim 3, wherein the subject has an insulin resistance disorder.

18. The method of claim 3, wherein the subject has hyperinsulinemia.

19. The method of claim 3, wherein the subject has glucose intolerance.

20. The method of claim 3, wherein the subject has a hyperglycemic disorder or is at risk of developing a hyperglycemic disorder.

21. The method of claim 3, wherein the subject has diabetes.

22. The method of claim 3, wherein the subject has insulin-dependent (type I) diabetes.

23. The method of claim 3, wherein the subject has type II diabetes.

24. The method of claim 3, wherein the subject has gestational diabetes.

25. The method of claim 3, wherein the subject is obese.

26. The method of claim 3, wherein the subject has a FPG level of greater than 100 mg/dl.

27. The method of claim 3, wherein the subject has an FPG level of 125 mg/dl or greater.

28. The method of claim 3, wherein the subject has an FPG level between 100 and 125 mg/dl.

29. The method of claim 3, wherein the glucose levels are reduced by at least 5%.

30. The method of claim 3, wherein the subject has a HbA1c level above 6%.

31. The method of claim 2, wherein the peptide is formulated as a pharmaceutical composition, wherein the pharmaceutical composition further comprises a pharmaceutically acceptable carrier.

32. The method of claim 2, wherein the method further comprises administration of a supplemental therapy.

33. The method of claim 32, wherein said supplemental therapy is a weight loss surgery, gastric bypass, gastrectomy, gastric banding, gastric balloon, or gastric sleeve.

34. The method of claim 32, wherein said supplemental therapy is a glucose lowering agent, insulin, GLP1 analogue, biguanide, sulphonylurea, thiazolidinedione, a dipeptidyl peptidase-4 (DPP-4) inhibitor, a bromocriptine formulation, a bile acid sequestrant, metformin, a thiazolidinedione (TZD), a SGLT-2 inhibitor, or any combination thereof.

35. The method of claim 34, wherein said biguanide or sulphonylurea is selected from the group consisting of tolbutamide, chlorpropamide, acetohexamide, tolazamide, glibenclamide, glipizide or any combination thereof.

36. The method of claim 34, wherein said thiazolidinedione is rosiglitazone or pioglitazone, or combination thereof.

37. The method of claim 34, wherein said bile acid sequestrant is colesevelam.

38. The method of claim 34, wherein said insulin is bolus insulin, basal insulin, or an analogue thereof.

39. The method of claim 32, wherein said supplemental therapy is administered prior to said method.

40. The method of claim 32, wherein said supplemental therapy is administered contemporaneously with said method.

41. The method of claim 32, wherein said supplemental therapy is administered following said method.

42. The method of claim 2, wherein the glucose levels are blood glucose levels.

43. The method of claim 2, wherein the subject has a metabolic disorder.

44. The method of claim 2, wherein the subject has an insulin resistance disorder.

45. The method of claim 2, wherein the subject has hyperinsulinemia.

46. The method of claim 2, wherein the subject has glucose intolerance.

47. The method of claim 2, wherein the subject has a hyperglycemic disorder or is at risk of developing a hyperglycemic disorder.

48. The method of claim 2, wherein the subject has diabetes.

49. The method of claim 2, wherein the subject has insulin-dependent (type I) diabetes.

50. The method of claim 2, wherein the subject has type II diabetes.

51. The method of claim 2, wherein the subject has gestational diabetes.

52. The method of claim 2, wherein the subject is obese.

53. The method of claim 2, wherein the subject has a fasting plasma glucose (FPG) level of greater than 100 mg/dl.

54. The method of claim 2, wherein the subject has an FPG level of 125 mg/dl or greater.

55. The method of claim 2, wherein the subject has an FPG level between 100 and 125 mg/dl.

56. The method of claim 2, wherein the glucose levels are reduced by at least 5%.

57. The method of claim 2, wherein the subject has a hemoglobin A1c (HbA1c) level above 6%.

58. The method of claim 1, wherein the peptide has an amino acid sequence consisting of SEQ ID NO:69.

59. The method of claim 58, wherein the peptide is fused with an immunoglobulin Fc region.

60. The method of claim 59, wherein the peptide is formulated as a pharmaceutical composition, wherein the pharmaceutical composition further comprises a pharmaceutically acceptable carrier.

61. The method of claim 59, wherein the method further comprises administration of a supplemental therapy.

62. The method of claim 61, wherein said supplemental therapy is a weight loss surgery, gastric bypass, gastrectomy, gastric banding, gastric balloon, or gastric sleeve.

63. The method of claim 61, wherein said supplemental therapy is a glucose lowering agent, insulin, GLP1 analogue, biguanide, sulphonylurea, thiazolidinedione, a DPP-4 inhibitor, a bromocriptine formulation, a bile acid sequestrant, metformin, a TZD, a SGLT-2 inhibitor, or any combination thereof.

64. The method of claim 63, wherein said biguanide or sulphonylurea is selected from the group consisting of tolbutamide, chlorpropamide, acetohexamide, tolazamide, glibenclamide, glipizide or any combination thereof.

65. The method of claim 63, wherein said thiazolidinedione is rosiglitazone or pioglitazone, or combination thereof.

66. The method of claim 63, wherein said bile acid sequestrant is colesevelam.

67. The method of claim 63, wherein said insulin is bolus insulin, basal insulin, or an analogue thereof.

68. The method of claim 61, wherein said supplemental therapy is administered prior to said method.

69. The method of claim 61, wherein said supplemental therapy is administered contemporaneously with said method.

70. The method of claim 61, wherein said supplemental therapy is administered following said method.

71. The method of claim 59, wherein the glucose levels are blood glucose levels.

72. The method of claim 59, wherein the subject has a metabolic disorder.

73. The method of claim 59, wherein the subject has an insulin resistance disorder.

74. The method of claim 59, wherein the subject has hyperinsulinemia.

75. The method of claim 59, wherein the subject has glucose intolerance.

76. The method of claim 59, wherein the subject has a hyperglycemic disorder or is at risk of developing a hyperglycemic disorder.

77. The method of claim 59, wherein the subject has diabetes.

78. The method of claim 59, wherein the subject has insulin-dependent (type I) diabetes.

79. The method of claim 59, wherein the subject has type II diabetes.

80. The method of claim 59, wherein the subject has gestational diabetes.

81. The method of claim 59, wherein the subject is obese.

82. The method of claim 59, wherein the subject has a FPG level of greater than 100 mg/dl.

83. The method of claim 59, wherein the subject has an FPG level of 125 mg/dl or greater.

84. The method of claim 59, wherein the subject has an FPG level between 100 and 125 mg/dl.

85. The method of claim 59, wherein the glucose levels are reduced by at least 5%.

86. The method of claim 59, wherein the subject has a HbA1c level above 6%.

87. The method of claim 58, wherein the peptide is formulated as a pharmaceutical composition, wherein the pharmaceutical composition further comprises a pharmaceutically acceptable carrier.

88. The method of claim 58, wherein the method further comprises administration of a supplemental therapy.

89. The method of claim 88, wherein said supplemental therapy is a weight loss surgery, gastric bypass, gastrectomy, gastric banding, gastric balloon, or gastric sleeve.

90. The method of claim 88, wherein said supplemental therapy is a glucose lowering agent, insulin, GLP1 analogue, biguanide, sulphonylurea, thiazolidinedione, a DPP-4 inhibitor, a bromocriptine formulation, a bile acid sequestrant, metformin, a TZD, a SGLT-2 inhibitor, or any combination thereof.

91. The method of claim 90, wherein said biguanide or sulphonylurea is selected from the group consisting of tolbutamide, chlorpropamide, acetohexamide, tolazamide, glibenclamide, glipizide or any combination thereof.

92. The method of claim 90, wherein said thiazolidinedione is rosiglitazone or pioglitazone, or combination thereof.

93. The method of claim 90, wherein said bile acid sequestrant is colesevelam.

94. The method of claim 90, wherein said insulin is bolus insulin, basal insulin, or an analogue thereof.

95. The method of claim 90, wherein said supplemental therapy is administered prior to said method.

96. The method of claim 90, wherein said supplemental therapy is administered contemporaneously with said method.

97. The method of claim 90, wherein said supplemental therapy is administered following said method.

98. The method of claim 58, wherein the glucose levels are blood glucose levels.

99. The method of claim 58, wherein the subject has a metabolic disorder.

100. The method of claim 58, wherein the subject has an insulin resistance disorder.

101. The method of claim 58, wherein the subject has hyperinsulinemia.

102. The method of claim 58, wherein the subject has glucose intolerance.

103. The method of claim 58, wherein the subject has a hyperglycemic disorder or is at risk of developing a hyperglycemic disorder.

104. The method of claim 58, wherein the subject has diabetes.

105. The method of claim 58, wherein the subject has insulin-dependent (type I) diabetes.

106. The method of claim 58, wherein the subject has type II diabetes.

107. The method of claim 58, wherein the subject has gestational diabetes.

108. The method of claim 58, wherein the subject is obese.

109. The method of claim 58, wherein the subject has a FPG level of greater than 100 mg/dl.

110. The method of claim 58, wherein the subject has an FPG level of 125 mg/dl or greater.

111. The method of claim 58, wherein the subject has an FPG level between 100 and 125 mg/dl.

112. The method of claim 58, wherein the glucose levels are reduced by at least 5%.

113. The method of claim 58, wherein the subject has a HbA1c level above 6%.

\* \* \* \* \*